(12) United States Patent
Freeman et al.

(10) Patent No.: US 9,820,684 B2
(45) Date of Patent: Nov. 21, 2017

(54) METHOD AND APPARATUS FOR A FLUID SAMPLING DEVICE

(75) Inventors: Dominique Freeman, La Honda, CA (US); Thomas Schulte, Redmond, CA (US); Michael Cane, Cambridge (GB); Don Alden, Sunnyvale, CA (US); Matt Schumann, Cambridge (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1690 days.

(21) Appl. No.: 12/088,370

(22) PCT Filed: Jun. 3, 2005

(86) PCT No.: PCT/US2005/019445
§ 371 (c)(1),
(2), (4) Date: Jul. 10, 2009

(87) PCT Pub. No.: WO2005/120365
PCT Pub. Date: Dec. 22, 2005

(65) Prior Publication Data
US 2010/0286560 A1 Nov. 11, 2010

Related U.S. Application Data

(60) Provisional application No. 60/577,376, filed on Jun. 3, 2004, provisional application No. 60/577,412, filed on Jun. 3, 2004.

(51) Int. Cl.
*A61B 5/00* (2006.01)
*A61B 5/157* (2006.01)
(Continued)

(52) U.S. Cl.
CPC ........ *A61B 5/157* (2013.01); *A61B 5/150022* (2013.01); *A61B 5/15113* (2013.01);
(Continued)

(58) Field of Classification Search
CPC .............. A61B 5/1411; A61B 5/15146; A61B 5/150534; A61B 5/150572;
(Continued)

(56) References Cited

U.S. PATENT DOCUMENTS

| 2,061 | A | 4/1841 | Osdel ............................ 606/182 |
| 55,620 | A | 6/1866 | Capewell ....................... 606/181 |

(Continued)

FOREIGN PATENT DOCUMENTS

| CN | 1946340 A | 4/2007 | |
| DE | 2206674 | 8/1972 | ............. C07D 39/10 |

(Continued)

OTHER PUBLICATIONS

G. Jarzabek, Z. Borkowska, On the Real Surface Area of Smooth Solid Electrodes, 1997, Electrochimica Acta, vol. 42, No. 19, pp. 2915-2918.

(Continued)

*Primary Examiner* — Devin Henson
(74) *Attorney, Agent, or Firm* — Paul Davis; Beyer Law Group LLP

(57) ABSTRACT

Methods and apparatus are provided for manufacturing an analyte detecting device. In one embodiment, the apparatus comprises a housing; a penetrating member driver; a cartridge containing a plurality of penetrating members; a display on the cartridge; a linear slider on the housing, the slider coupled to a rod; and the rod moving with the slider, the rod having at least one roller. The device uses the linear motion of the slider to rotate the cartridge, punch open a new cavity and load a new penetrating member.

17 Claims, 29 Drawing Sheets

(51) Int. Cl.
  *A61B 5/151* (2006.01)
  *A61B 5/15* (2006.01)
(52) U.S. Cl.
  CPC ...... *A61B 5/15117* (2013.01); *A61B 5/15123*
    (2013.01); *A61B 5/15146* (2013.01); *A61B 5/15151* (2013.01); *A61B 5/150152* (2013.01);
    *A61B 5/15161* (2013.01); *A61B 5/150167*
    (2013.01); *A61B 5/150175* (2013.01); *A61B 5/150358* (2013.01); *A61B 5/150427*
    (2013.01); *A61B 5/150503* (2013.01); *A61B 5/150572* (2013.01); *A61B 5/1518* (2013.01);
    *A61B 5/15149* (2013.01); *A61B 5/15153*
    (2013.01); *A61B 5/15155* (2013.01); *A61B 5/15159* (2013.01); *A61B 5/15176* (2013.01);
    *A61B 5/15178* (2013.01); *A61B 5/150259*
    (2013.01); *A61B 5/150312* (2013.01); *A61B 5/150534* (2013.01); *A61B 5/150541* (2013.01)
(58) Field of Classification Search
  CPC ........ A61B 5/150541; A61B 5/150259; A61B 5/150312; A61B 5/15149; A61B 5/15176; A61B 5/15178; A61B 5/1518; A61B 5/15151; A61B 5/15153; A61B 5/15155; A61B 5/15159; A61B 5/15161
  USPC .................. 600/583, 575, 341, 573; 606/181
  See application file for complete search history.

(56) References Cited

U.S. PATENT DOCUMENTS

| | | | | |
|---|---|---|---|---|
| 1,135,465 | A | 4/1915 | Pollock | 606/181 |
| 1,733,847 | A | 10/1929 | Wilmot | 292/332 |
| 2,258,857 | A | 10/1941 | McCann | 601/81 |
| 2,628,319 | A | 2/1953 | Vang | 310/15 |
| 2,714,890 | A | 8/1955 | Alfred | 606/169 |
| 2,763,935 | A | 9/1956 | Whaley | 33/511 |
| 2,801,633 | A | 8/1957 | Ehrlich | 606/181 |
| 2,880,876 | A | 4/1959 | Dujardin | 210/523 |
| 3,046,987 | A | 7/1962 | Ehrlich | 128/314 |
| 3,030,959 | A | 9/1962 | Grunert | 128/329 |
| 3,063,451 | A | 11/1962 | Kowalk | 600/576 |
| 3,086,288 | A | 4/1963 | Balamuth | 30/277.4 |
| 3,090,384 | A | 5/1963 | Baldwin et al. | 604/272 |
| 3,208,452 | A | 9/1965 | Stern | 606/182 |
| 3,358,689 | A | 12/1967 | Higgins | 128/329 |
| 3,412,729 | A | 11/1968 | Smith, Jr. | 128/2.05 |
| 3,424,154 | A | 1/1969 | Kinsley | 604/70 |
| 3,448,307 | A | 6/1969 | Rudolph | 310/23 |
| 3,494,358 | A | 2/1970 | Grossenbacher | 128/218 |
| 3,607,097 | A | 9/1971 | Auphan et al. | 422/66 |
| 3,620,209 | A | 11/1971 | Kravitz | 601/79 |
| 3,626,929 | A | 12/1971 | Sanz | 128/2 R |
| 3,628,026 | A | 12/1971 | Cronin | 250/214.1 |
| 3,665,672 | A | 5/1972 | Speelman | 53/435 |
| 3,673,475 | A | 6/1972 | Britton | 318/122 |
| 3,712,292 | A | 1/1973 | Mielke, Jr. | 128/2 G |
| 3,712,293 | A | 1/1973 | Mielke, Jr. | 128/2 |
| 3,734,812 | A | 5/1973 | Yazawa | 428/107 |
| 3,742,954 | A | 7/1973 | Strickland | 128/302 |
| 3,780,960 | A | 12/1973 | Tokuno | 242/555.2 |
| 3,832,776 | A | 9/1974 | Sawyer | 30/272 |
| 3,836,148 | A | 9/1974 | Manning | 273/368 |
| 3,851,543 | A | 12/1974 | Krom | 74/493 |
| 3,853,010 | A | 12/1974 | Christen | 73/864.24 |
| 3,924,818 | A | 12/1975 | Pfeifle | 242/364.7 |
| 3,938,526 | A | 2/1976 | Anderson | 128/303.1 |
| 3,953,172 | A | 4/1976 | Shapiro | 23/230 |
| 3,971,365 | A | 7/1976 | Smith | 128/2.17 |
| 4,057,394 | A | 11/1977 | Genshaw | 23/230 |
| 4,077,406 | A | 3/1978 | Sandhage | 604/61 |
| 4,109,655 | A | 8/1978 | Chaconac | 128/253 |
| 4,139,011 | A | 2/1979 | Benoit | 606/182 |
| 4,154,228 | A | 5/1979 | Feldstein | 606/169 |
| 4,168,130 | A | 9/1979 | Barth | 404/99 |
| 4,184,486 | A | 1/1980 | Papa | 600/373 |
| 4,190,420 | A | 2/1980 | Covington | 422/63 |
| 4,191,193 | A | 3/1980 | Seo | 600/488 |
| 4,193,690 | A | 3/1980 | Levenson | 356/301 |
| 4,203,446 | A | 5/1980 | Hofert | 606/182 |
| 4,207,870 | A | 6/1980 | Eldridge | 128/766 |
| 4,223,674 | A | 9/1980 | Fluent | 604/504 |
| 4,224,125 | A | 9/1980 | Nakamura | 204/195 B |
| 4,224,949 | A | 9/1980 | Scott | 128/734 |
| 4,230,118 | A | 10/1980 | Holman et al. | 128/314 |
| 4,240,439 | A | 12/1980 | Abe | 600/412 |
| 4,254,083 | A | 3/1981 | Columbus | 422/55 |
| 4,258,001 | A | 3/1981 | Pierce | 422/56 |
| 4,259,653 | A | 3/1981 | McGonigal | 310/15 |
| 4,299,230 | A | 11/1981 | Kubota | 600/300 |
| 4,301,412 | A | 11/1981 | Hill | 324/442 |
| 4,321,397 | A | 3/1982 | Nix | 548/366 |
| 4,338,174 | A | 7/1982 | Tamura | 204/195 |
| 4,340,669 | A | 7/1982 | Bauer | 435/14 |
| 4,350,762 | A | 9/1982 | De Luca | 435/10 |
| 4,353,984 | A | 10/1982 | Yamada | 435/14 |
| 4,356,826 | A | 11/1982 | Kubota | 600/300 |
| 4,360,016 | A | 11/1982 | Sarrine | 128/763 |
| 4,388,922 | A | 6/1983 | Telang | 604/319 |
| 4,391,905 | A | 7/1983 | Bauer | 435/14 |
| 4,391,906 | A | 7/1983 | Bauer | 435/14 |
| 4,392,933 | A | 7/1983 | Nakamura | 204/403.14 |
| 4,394,512 | A | 7/1983 | Batz | 548/365 |
| 4,397,556 | A | 8/1983 | Muller | 356/301 |
| 4,407,008 | A | 9/1983 | Schmidt | 356/301 |
| 4,411,266 | A | 10/1983 | Cosman | 128/303.18 |
| 4,414,975 | A | 11/1983 | Ryder | 128/314 |
| 4,418,037 | A | 11/1983 | Katsuyama | 422/56 |
| 4,420,564 | A | 12/1983 | Tsuji | 435/288 |
| 4,425,039 | A | 1/1984 | Grant | 356/35.5 |
| 4,426,451 | A | 1/1984 | ColumbUS | 436/518 |
| 4,426,884 | A | 1/1984 | Polchaninoff | 73/172 |
| 4,440,301 | A | 4/1984 | Intengan | 206/456 |
| 4,442,836 | A | 4/1984 | Meinecke | 128/314 |
| 4,442,972 | A | 4/1984 | Sahay | 236/1 EA |
| 4,449,529 | A | 5/1984 | Burns | 606/182 |
| 4,462,405 | A | 7/1984 | Ehrlich | 606/182 |
| 4,469,110 | A | 9/1984 | Slama | 128/770 |
| 4,490,139 | A | 12/1984 | Huizenga et al. | 604/57 |
| 4,517,978 | A | 5/1985 | Levin | 128/314 |
| 4,518,384 | A | 5/1985 | Tarello | 604/61 |
| 4,523,994 | A | 6/1985 | Shono | 549/352 |
| 4,525,164 | A | 6/1985 | Loeb et al. | |
| 4,535,769 | A | 8/1985 | Burns | 128/314 |
| 4,535,773 | A | 8/1985 | Yoon | 606/185 |
| 4,537,197 | A | 8/1985 | Hulka | 128/633 |
| 4,539,988 | A | 9/1985 | Shirley | 128/314 |
| 4,545,382 | A | 10/1985 | Higgins | 128/635 |
| 4,553,541 | A | 11/1985 | Burns | 128/314 |
| 4,561,445 | A | 12/1985 | Berke | 128/642 |
| 4,577,630 | A | 3/1986 | Nitzsche | 128/314 |
| 4,580,564 | A | 4/1986 | Anderson | 502/8 |
| 4,580,565 | A | 4/1986 | Cornell | 128/314 |
| 4,586,819 | A | 5/1986 | Tochigi | 356/301 |
| 4,586,926 | A | 5/1986 | Osborne | 604/272 |
| 4,590,411 | A | 5/1986 | Kelly | 318/687 |
| 4,595,479 | A | 6/1986 | Kimura | 204/294 |
| 4,600,014 | A | 7/1986 | Beraha | 128/754 |
| 4,603,209 | A | 7/1986 | Tsien | 549/352 |
| 4,608,997 | A | 9/1986 | Conway | 128/763 |
| 4,615,340 | A | 10/1986 | Cronenberg | 128/635 |
| 4,616,649 | A | 10/1986 | Burns | 128/314 |
| 4,619,754 | A | 10/1986 | Niki | 204/290 |
| 4,622,974 | A | 11/1986 | Coleman | 128/634 |
| 4,624,253 | A | 11/1986 | Burns | 128/314 |
| 4,627,445 | A | 12/1986 | Garcia | 600/583 |
| 4,637,393 | A | 1/1987 | Ray | 128/305 |
| 4,637,403 | A | 1/1987 | Garcia | 600/583 |
| 4,643,189 | A | 2/1987 | Mintz | 128/314 |
| 4,648,408 | A | 3/1987 | Hutcheson | 128/770 |
| 4,648,714 | A | 3/1987 | Benner | 356/301 |
| 4,653,511 | A | 3/1987 | Goch | 128/763 |

(56) References Cited

U.S. PATENT DOCUMENTS

| | | | |
|---|---|---|---|
| 4,653,513 A | 3/1987 | Dombrowski | 600/578 |
| 4,655,225 A | 4/1987 | Dahne | 600/316 |
| 4,661,768 A | 4/1987 | Carusillo | 324/678 |
| 4,666,438 A | 5/1987 | Raulerson | 604/272 |
| 4,676,244 A | 6/1987 | Enstrom | 128/314 |
| 4,677,979 A | 7/1987 | Burns | 128/314 |
| 4,678,277 A | 7/1987 | Delhaye | 356/301 |
| 4,682,892 A | 7/1987 | Chawla | 356/353 |
| 4,695,273 A | 9/1987 | Brown | |
| 4,702,594 A | 10/1987 | Grant | 356/35.5 |
| 4,711,245 A | 12/1987 | Higgins | 128/635 |
| 4,712,460 A | 12/1987 | Allen | 83/208 |
| 4,712,548 A | 12/1987 | Enstrom | 128/314 |
| 4,714,462 A | 12/1987 | DiDomenico | 604/67 |
| 4,715,374 A | 12/1987 | Maggio | 128/314 |
| 4,731,330 A | 3/1988 | Hilll | 436/16 |
| 4,731,726 A | 3/1988 | Allen, III | 600/300 |
| 4,734,360 A | 3/1988 | Phillips | 435/25 |
| 4,735,203 A | 4/1988 | Ryder | 128/314 |
| 4,737,458 A | 4/1988 | Batz | 435/28 |
| 4,750,489 A | 6/1988 | Berkman | 606/166 |
| 4,753,776 A | 6/1988 | Hillman | 422/101 |
| 4,756,884 A | 7/1988 | Hillman | 422/73 |
| 4,757,022 A | 7/1988 | Shults et al. | 435/291 |
| 4,758,323 A | 7/1988 | Davis | 204/403 |
| 4,774,192 A | 9/1988 | Teriniello | 436/530 |
| 4,784,486 A | 11/1988 | Van Wagenen | 356/301 |
| 4,787,398 A * | 11/1988 | Garcia | A61B 5/1411 600/583 |
| 4,790,979 A | 12/1988 | Teriniello | 422/56 |
| 4,794,926 A | 1/1989 | Munsch et al. | 606/183 |
| 4,797,283 A | 1/1989 | Allen | 424/443 |
| RE32,922 E | 3/1989 | Levin | 128/314 |
| 4,814,142 A | 3/1989 | Gleisner | 422/56 |
| 4,814,661 A | 3/1989 | Ratzlaff | 310/328 |
| 4,817,603 A | 4/1989 | Turner | 606/182 |
| 4,818,493 A | 4/1989 | Coville | 422/102 |
| 4,820,010 A | 4/1989 | Sciefres | 385/43 |
| 4,820,399 A | 4/1989 | Senda | 204/403 |
| 4,823,806 A | 4/1989 | Bajada | 600/557 |
| 4,824,639 A | 4/1989 | Hildenbrand | 422/56 |
| 4,825,711 A | 5/1989 | Jensen | 73/865.8 |
| 4,827,763 A | 5/1989 | Bourland | 73/172 |
| 4,829,011 A | 5/1989 | Gibbons | 436/512 |
| 4,830,959 A | 5/1989 | McNeill | 435/53 |
| 4,836,904 A | 6/1989 | Armstron | 204/294 |
| 4,840,893 A | 6/1989 | Hill | 435/6 |
| 4,844,095 A | 7/1989 | Chiodo | 128/314 |
| 4,845,392 A | 7/1989 | Mumbower | 310/14 |
| 4,850,973 A | 7/1989 | Jordan | 604/157 |
| 4,857,274 A | 8/1989 | Simon | 422/72 |
| 469,265 A | 9/1989 | McEwen | 128/774 |
| 4,868,129 A | 9/1989 | Gibbons | 436/179 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,877,026 A | 10/1989 | de Laforcade | 128/305 |
| 4,882,013 A | 11/1989 | Turner | 204/1 |
| 4,883,055 A | 11/1989 | Merrick | 128/633 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,895,156 A | 1/1990 | Schulze | 600/342 |
| 4,897,173 A | 1/1990 | Nankai | 204/403 |
| 4,935,346 A | 1/1990 | Phillips | 435/14 |
| 4,900,424 A | 2/1990 | Birch | 204/409 |
| 4,900,666 A | 2/1990 | Phillips | 435/25 |
| 4,911,794 A | 3/1990 | Parce | 204/1 T |
| 4,920,977 A | 5/1990 | Haynes | 128/770 |
| 4,924,879 A | 5/1990 | O'brien | 600/583 |
| 4,938,218 A | 7/1990 | Goodman | 128/633 |
| 4,940,468 A | 7/1990 | Petillo | 606/170 |
| 4,944,304 A | 7/1990 | Nishina | 128/667 |
| 4,945,045 A | 7/1990 | Forrest | 435/25 |
| 4,946,795 A | 8/1990 | Gibbons | 436/179 |
| 4,948,727 A | 8/1990 | Cass | 435/18 |
| 4,948,961 A | 8/1990 | Hillman | 250/252.1 |
| 4,952,373 A | 8/1990 | Sugarman | 422/99 |
| 4,952,515 A | 8/1990 | Gleisner | 436/169 |
| 4,953,552 A | 9/1990 | DeMarzo | 128/635 |
| 4,953,976 A | 9/1990 | Adler-Golden | 356/301 |
| 4,963,498 A | 10/1990 | Hillman | 436/69 |
| 4,966,581 A | 10/1990 | Landau | 604/72 |
| 4,966,646 A | 10/1990 | Zdeblick | 156/633 |
| 4,966,671 A | 10/1990 | Nylander | 204/153.14 |
| 4,975,581 A | 12/1990 | Robinson | 250/339 |
| 4,976,724 A | 12/1990 | Nieto | 606/182 |
| 4,977,910 A | 12/1990 | Miyahara | 134/7 |
| 4,983,178 A | 1/1991 | Schnell | 606/181 |
| 4,984,085 A | 1/1991 | Landowski | 358/213 |
| 4,990,154 A | 2/1991 | Brown | 606/182 |
| 4,995,402 A | 2/1991 | Smith | 600/584 |
| 4,999,582 A | 3/1991 | Parks | 324/438 |
| 5,001,054 A | 3/1991 | Wagner | 435/14 |
| 5,001,873 A | 3/1991 | Rufin | 451/39 |
| 5,004,923 A | 4/1991 | Hillman | 250/341 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,019,974 A | 5/1991 | Beckers | 364/413.02 |
| 5,026,388 A | 6/1991 | Ingalz | 606/182 |
| D318,331 S | 7/1991 | Phillips | D24/169 |
| 5,028,142 A | 7/1991 | Vladimir | 366/273 |
| 5,029,583 A | 7/1991 | Meserol | 600/316 |
| 5,035,704 A | 7/1991 | Lambert | 606/182 |
| 5,039,617 A | 8/1991 | McDonald | 436/69 |
| 5,043,143 A | 8/1991 | Shaw | 422/65 |
| 5,046,496 A | 9/1991 | Betts | 600/352 |
| 5,047,044 A | 9/1991 | Smith | 606/182 |
| 5,049,373 A | 9/1991 | Tsien | 549/352 |
| 5,049,487 A | 9/1991 | Phillips | 435/4 |
| 5,054,487 A | 10/1991 | Clarke | 128/633 |
| 5,054,499 A | 10/1991 | Swierczek | 128/770 |
| 5,057,082 A | 10/1991 | Burchette, Jr. | 604/164 |
| 5,057,277 A | 10/1991 | Mauze | 422/56 |
| 5,059,394 A | 10/1991 | Phillips | 422/68.1 |
| 5,059,789 A | 10/1991 | Salcudean | 250/206.1 |
| 5,060,174 A | 10/1991 | Gross | 702/139 |
| 5,062,898 A | 11/1991 | McDermott | 134/7 |
| 5,064,411 A | 11/1991 | Gordon, III | 604/48 |
| 5,070,874 A | 12/1991 | Barnes | 128/633 |
| 5,070,886 A | 12/1991 | Mitchen | 128/771 |
| 5,073,500 A | 12/1991 | Saito et al. | 436/53 |
| 5,074,872 A | 12/1991 | Brown | 606/182 |
| 5,077,017 A | 12/1991 | Gorin | 422/100 |
| 5,077,199 A | 12/1991 | Basagni | 435/14 |
| 5,080,865 A | 1/1992 | Leiner | 422/68.1 |
| 5,126,034 A | 1/1992 | Carter | 204/403 |
| 5,086,229 A | 2/1992 | Rosenthal | 250/341 |
| 5,089,112 A | 2/1992 | Skotheim | 204/403 |
| 5,092,842 A | 3/1992 | Bechtold | 604/135 |
| 5,094,943 A | 3/1992 | Siedel | 435/25 |
| 5,096,669 A | 3/1992 | Lauks | 204/403.02 |
| 5,097,810 A | 3/1992 | Fishman | 600/556 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,382 A | 4/1992 | Brinkerhoff et al. | 604/164.12 |
| 5,104,619 A | 4/1992 | Castro | 422/56 |
| 5,104,813 A | 4/1992 | Besemer | 436/179 |
| 5,107,764 A | 4/1992 | Gasparrini | 101/425 |
| 5,108,564 A | 4/1992 | Szuminsky | 204/153.12 |
| 5,108,889 A | 4/1992 | Smith | 435/4 |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,128,015 A | 7/1992 | Szuminsky | 204/403 |
| 5,128,171 A | 7/1992 | Gleisner | 427/2 |
| 5,132,801 A | 7/1992 | Yamano | 358/213 |
| 5,133,730 A | 7/1992 | Biro | 606/182 |
| 5,135,719 A | 8/1992 | Hillman | 422/101 |
| 5,139,685 A | 8/1992 | Castro | 210/767 |

(56) References Cited

U.S. PATENT DOCUMENTS

| | | | |
|---|---|---|---|
| 5,140,161 A | 8/1992 | Hillman | 250/341 |
| 5,141,868 A | 8/1992 | Shanks | 435/288 |
| 5,144,139 A | 9/1992 | Hillman | 250/341 |
| 5,145,565 A | 9/1992 | Kater | 600/341 |
| 5,146,091 A | 9/1992 | Knudson | 250/341.6 |
| 5,152,296 A | 10/1992 | Simons | 128/670 |
| 5,152,775 A * | 10/1992 | Ruppert | A61B 5/1411 221/270 |
| 5,153,671 A | 10/1992 | Miles | 356/301 |
| 5,156,611 A | 10/1992 | Haynes | 606/181 |
| 5,162,525 A | 11/1992 | Masilamani | 549/352 |
| 5,163,442 A * | 11/1992 | Ono | A61B 5/150022 600/565 |
| 5,164,598 A | 11/1992 | Hillman | 250/341 |
| 5,167,619 A | 12/1992 | Wuchinich | 604/22 |
| 5,170,364 A | 12/1992 | Gross | 702/139 |
| 5,174,726 A | 12/1992 | Findlay | 417/205 |
| D332,490 S | 1/1993 | Brown | D24/146 |
| 5,178,142 A | 1/1993 | Harjunmaa | 128/633 |
| 5,179,005 A | 1/1993 | Phillips | 435/14 |
| 5,181,910 A | 1/1993 | Scanlon | 604/67 |
| 5,181,914 A | 1/1993 | Zook | 604/307 |
| 5,183,042 A | 2/1993 | Harjunmaa | 128/633 |
| 5,185,256 A | 2/1993 | Nankai | 435/174 |
| 5,187,100 A | 2/1993 | Matzinger | 436/16 |
| 5,188,118 A | 2/1993 | Terwilliger | 600/566 |
| 5,189,751 A | 3/1993 | Giuliani | 15/22.1 |
| 5,192,415 A | 3/1993 | Yoshioka | 204/403 |
| 5,194,391 A | 3/1993 | Mauze | 436/166 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,208,163 A | 5/1993 | Charlton et al. | 436/63 |
| 5,209,028 A | 5/1993 | McDermott | 51/426 |
| 5,211,652 A | 5/1993 | Derbyshire | 606/182 |
| 5,212,879 A | 5/1993 | Biro | 29/437 |
| 5,215,587 A | 6/1993 | McConnellogue | 118/699 |
| 5,216,597 A | 6/1993 | Beckers | 364/413.02 |
| 5,217,476 A | 6/1993 | Wishinsky | 606/167 |
| 5,217,480 A | 6/1993 | Haber | 606/182 |
| 5,218,966 A | 6/1993 | Yamasawa | 600/499 |
| 5,222,504 A | 6/1993 | Solomon | 600/557 |
| 5,228,972 A | 7/1993 | Osaka | 204/415 |
| 5,229,282 A | 7/1993 | Yoshioka | 435/177 |
| 5,230,866 A | 7/1993 | Shartle | 422/103 |
| 5,231,993 A | 8/1993 | Haber et al. | 128/770 |
| 5,241,969 A | 9/1993 | Carson | 600/566 |
| 5,247,932 A | 9/1993 | Chung | 128/633 |
| 5,249,583 A | 10/1993 | Mallaby | 600/567 |
| 5,250,066 A | 10/1993 | Lambert | 606/181 |
| 5,251,126 A | 10/1993 | Kahn | 364/413.11 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| 5,266,359 A | 11/1993 | Spielvogel | 427/388.4 |
| D342,673 S | 12/1993 | Cerola | D24/147 |
| 5,267,974 A | 12/1993 | Lambert | 604/195 |
| 5,272,087 A | 12/1993 | El Murr | 435/291 |
| 5,277,181 A | 1/1994 | Mendelson | 128/633 |
| 5,279,294 A | 1/1994 | Anderson | 600/322 |
| 5,279,791 A | 1/1994 | Aldrich | 422/58 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |
| 5,288,636 A | 2/1994 | Pollman | 435/288 |
| 5,294,261 A | 3/1994 | McDermott | 134/7 |
| 5,296,378 A | 3/1994 | Sakata | 436/63 |
| 5,300,779 A | 4/1994 | Hillman | 250/341 |
| 5,304,192 A | 4/1994 | Crouse | 606/181 |
| 5,304,193 A | 4/1994 | Zhadanov | 606/182 |
| 5,304,347 A | 4/1994 | Mann | 422/67 |
| 5,304,468 A | 4/1994 | Phillips | 435/14 |
| 5,306,623 A | 4/1994 | Kiser | 435/14 |
| 5,307,263 A | 4/1994 | Brown | 600/301 |
| 5,312,590 A | 5/1994 | Gunasingham | 422/56 |
| 5,314,441 A | 5/1994 | Cusack | 606/182 |
| 5,314,442 A | 5/1994 | Susumu | 606/182 |
| 5,315,793 A | 5/1994 | Peterson | 451/2 |
| 5,316,012 A | 5/1994 | Siegal | 128/744 |
| 5,316,229 A | 5/1994 | Draghetti | 606/171 |
| 5,318,583 A | 6/1994 | Rabenau | 606/182 |
| 5,318,584 A | 6/1994 | Lange | 606/182 |
| 5,320,607 A | 6/1994 | Ishibashi | 604/115 |
| 5,320,808 A | 6/1994 | Holen | 422/64 |
| 5,324,302 A | 6/1994 | Crouse | 606/181 |
| 5,324,303 A | 6/1994 | Strong | 606/181 |
| 5,330,634 A | 7/1994 | Wong | 205/777.5 |
| 5,332,479 A | 7/1994 | Uenoyama | 204/153.12 |
| 5,341,206 A | 8/1994 | Pittaro | 356/301 |
| 5,342,382 A | 8/1994 | Brinkerhoff | 606/184 |
| 5,344,703 A | 9/1994 | Kovar | 428/312.6 |
| 5,350,392 A | 9/1994 | Purcell | 606/182 |
| 5,352,351 A | 10/1994 | White | 204/406 |
| 5,354,287 A | 10/1994 | Wacks | 604/232 |
| 5,354,447 A | 10/1994 | Uenoyama | 204/403 |
| 5,356,420 A | 10/1994 | Czernecki | 606/182 |
| 5,360,410 A | 11/1994 | Wacks | 604/232 |
| 5,365,699 A | 11/1994 | Armstrong | 451/7 |
| 5,366,469 A | 11/1994 | Steg | 606/182 |
| 5,366,470 A | 11/1994 | Ramel | 606/183 |
| 5,366,609 A | 11/1994 | White | 204/403 |
| 5,368,047 A | 11/1994 | Suzuki | 600/578 |
| 5,370,509 A | 12/1994 | Golding | 417/423.1 |
| 5,371,687 A | 12/1994 | Holmes | 364/514 |
| 5,372,135 A | 12/1994 | Mendelson | 600/322 |
| 5,375,397 A | 12/1994 | Ferrand | 54/66 |
| 5,378,628 A | 1/1995 | Graetzel | 435/288 |
| 5,382,346 A | 1/1995 | Uenoyama | 204/403 |
| 5,383,885 A | 1/1995 | Bland | 606/182 |
| 5,389,534 A | 2/1995 | Gentezkow | 435/180 |
| 5,390,450 A | 2/1995 | Goenka | 451/39 |
| 5,393,903 A | 2/1995 | Graetzel | 556/137 |
| 5,395,339 A | 3/1995 | Talonn | 604/111 |
| 5,395,387 A | 3/1995 | Burns | 606/181 |
| 5,397,334 A | 3/1995 | Schenk | 606/182 |
| 5,401,376 A | 3/1995 | Foos | 204/415 |
| 5,402,798 A | 4/1995 | Swierczek | 128/770 |
| 5,405,283 A | 4/1995 | Goenka | 451/39 |
| 5,405,510 A | 4/1995 | Betts | 205/782 |
| 5,405,511 A | 4/1995 | White | 204/153.1 |
| 5,407,545 A | 4/1995 | Hirose | 204/153.12 |
| 5,407,554 A | 4/1995 | Saurer | 204/403 |
| 5,407,818 A | 4/1995 | Gentezkow | 435/180 |
| 5,409,583 A | 4/1995 | Yoshioka | 204/153.12 |
| 5,409,664 A | 4/1995 | Allen | 422/56 |
| 5,410,059 A | 4/1995 | Fraser | 546/10 |
| 5,410,474 A | 4/1995 | Fox | 600/300 |
| 5,415,169 A | 5/1995 | Siczek | 600/427 |
| 5,418,142 A | 5/1995 | Kiser | 435/14 |
| 5,423,847 A | 6/1995 | Strong et al. | 606/182 |
| 5,424,545 A | 6/1995 | Block | 350/343 |
| 5,426,032 A | 6/1995 | Phillips | 435/14 |
| 5,436,161 A | 7/1995 | Bergstrom | 435/291 |
| 5,437,999 A | 8/1995 | Diebold | 435/288 |
| 5,438,271 A | 8/1995 | White | 324/444 |
| 5,443,701 A | 8/1995 | Willner | 204/153 |
| 5,445,920 A | 8/1995 | Saito | 430/311 |
| D362,719 S | 9/1995 | Kaplan | D24/147 |
| 5,453,360 A | 9/1995 | Yu | 435/28 |
| 5,454,828 A | 10/1995 | Schraga | 606/181 |
| 5,456,875 A | 10/1995 | Lambert | 264/328.1 |
| 5,459,325 A | 10/1995 | Hueton | 250/458.1 |
| 5,460,182 A | 10/1995 | Goodman | 600/342 |
| 5,462,533 A | 10/1995 | Daugherty | 604/164 |
| 5,464,418 A | 11/1995 | Schraga | 606/182 |
| 5,465,722 A | 11/1995 | Fort | 600/447 |
| 5,471,102 A | 11/1995 | Becker | 310/50 |
| 5,472,427 A | 12/1995 | Rammler | 604/164.01 |
| 5,474,084 A | 12/1995 | Cunniff | 600/557 |
| 5,476,474 A | 12/1995 | Davis | 606/182 |
| 5,480,387 A | 1/1996 | Gabriel | 604/134 |

(56) References Cited

U.S. PATENT DOCUMENTS

| | | | |
|---|---|---|---|
| 5,487,748 A | 1/1996 | Marshall | 606/182 |
| D367,109 S | 2/1996 | Ryner | D24/224 |
| 5,490,505 A | 2/1996 | Diab | 600/323 |
| 5,496,274 A | 3/1996 | Graves | 604/86 |
| 5,496,453 A | 3/1996 | Uenoyama | 205/777.5 |
| 5,498,542 A | 3/1996 | Corey | 435/283.1 |
| 5,501,836 A | 3/1996 | Myerson | 42/57 |
| 5,501,893 A | 3/1996 | Laermer | 428/161 |
| 5,507,288 A | 4/1996 | Bocker | 128/633 |
| 5,507,629 A | 4/1996 | Jarvik | 417/423.3 |
| 5,508,171 A | 4/1996 | Walling | 205/777.5 |
| 5,509,410 A | 4/1996 | Hill | 128/637 |
| 5,510,266 A | 4/1996 | Bonner et al. | 436/43 |
| 5,512,159 A | 4/1996 | Yoshioka | 204/403 |
| 5,514,152 A | 5/1996 | Smith | 606/182 |
| 5,515,170 A | 5/1996 | Matzinger | 356/423 |
| 5,518,006 A | 5/1996 | Mawhirt | 128/770 |
| D371,198 S | 6/1996 | Savage | D24/169 |
| 5,524,636 A | 6/1996 | Sarvazyan | 128/774 |
| 5,525,511 A | 6/1996 | D'Costa | 435/287.9 |
| 5,525,518 A | 6/1996 | Lundsgaard | 436/68 |
| 5,526,120 A | 6/1996 | Jina | 356/446 |
| 5,527,333 A | 6/1996 | Nikkels | 606/182 |
| 5,527,334 A | 6/1996 | Kanner | 606/182 |
| 5,529,074 A | 6/1996 | Greenfield | 600/557 |
| 5,540,676 A | 7/1996 | Freiberg | 606/3 |
| 5,540,709 A | 7/1996 | Ramel | 606/183 |
| 5,543,326 A | 8/1996 | Heller | 435/287.9 |
| 5,545,174 A | 8/1996 | Schenk | 606/182 |
| 5,545,291 A | 8/1996 | Smith | 438/107 |
| 5,547,702 A | 8/1996 | Gleisner | 427/2.13 |
| D373,419 S | 9/1996 | Muramatsu | D24/165 |
| 5,554,153 A | 9/1996 | Costello | 606/9 |
| 5,554,166 A | 9/1996 | Lange | 606/182 |
| 5,558,834 A | 9/1996 | Chu | 422/55 |
| 5,562,384 A | 10/1996 | Alvite | 414/226.01 |
| 5,562,696 A | 10/1996 | Nobles | 606/185 |
| 5,563,031 A | 10/1996 | Yu | 435/4 |
| 5,563,042 A | 10/1996 | Phillips | 435/14 |
| 5,569,286 A | 10/1996 | Peckham | 606/181 |
| 5,569,287 A | 10/1996 | Tezuka | 606/182 |
| 5,571,132 A | 11/1996 | Mawhirt | 606/182 |
| 5,575,284 A | 11/1996 | Athan | 600/323 |
| 5,575,403 A | 11/1996 | Charlton | 221/31 |
| 5,575,895 A | 11/1996 | Ikeda | 204/403 |
| 5,582,697 A | 12/1996 | Ikeda | 204/403 |
| 5,584,846 A | 12/1996 | Mawhirt | 606/181 |
| 5,591,139 A | 1/1997 | Lin | 604/264 |
| 5,593,852 A | 1/1997 | Heller | 435/14 |
| 5,599,501 A | 2/1997 | Carey | 422/99 |
| 5,605,837 A | 2/1997 | Karimi | 436/14 |
| D378,612 S | 3/1997 | Clark | D24/169 |
| 5,608,006 A | 3/1997 | Myerson | 525/54.1 |
| 5,609,749 A | 3/1997 | Yamauchi | 205/777.5 |
| 5,611,809 A | 3/1997 | Marshall | 606/181 |
| 5,611,810 A | 3/1997 | Arnold | 606/185 |
| 5,613,978 A | 3/1997 | Harding | 606/181 |
| 5,616,135 A | 4/1997 | Thorne | 604/192 |
| 5,617,851 A | 4/1997 | Lipkovker | 600/573 |
| 5,618,297 A | 4/1997 | Hart | 606/185 |
| 5,620,279 A | 4/1997 | Genshaw | 204/402 |
| 5,620,863 A | 4/1997 | Tomasco | 435/14 |
| 5,624,458 A | 4/1997 | Lipscher | 606/181 |
| 5,624,459 A | 4/1997 | Kortenbach | 606/185 |
| 5,624,537 A | 4/1997 | Turner | 204/403 |
| D379,516 S | 5/1997 | Rutter | D24/146 |
| 5,628,764 A | 5/1997 | Schraga | 606/182 |
| 5,628,765 A | 5/1997 | Susumu | 606/182 |
| 5,628,890 A | 5/1997 | Carter | 204/403 |
| 5,628,961 A | 5/1997 | Davis | 422/63 |
| 5,630,828 A | 5/1997 | Mawhirt | 606/187 |
| 5,630,986 A | 5/1997 | Charlton | 422/64 |
| 5,632,410 A | 5/1997 | Moulton | 221/79 |
| 5,640,954 A | 6/1997 | Pfeiffer | 128/635 |
| D381,591 S | 7/1997 | Rice | D10/81 |
| 5,643,306 A | 7/1997 | Schraga | 606/182 |
| 5,643,308 A | 7/1997 | Markman | 606/187 |
| 5,645,555 A | 7/1997 | Davis | 606/182 |
| 5,647,851 A | 7/1997 | Pokras | 604/131 |
| 5,650,062 A | 7/1997 | Ikeda | 205/778 |
| 5,653,863 A | 8/1997 | Genshaw | 205/777.5 |
| 5,657,760 A | 8/1997 | Ying et al. | 128/660.03 |
| 5,658,444 A | 8/1997 | Black | 204/415 |
| 5,660,791 A | 8/1997 | Brenneman | 422/58 |
| D383,550 S | 9/1997 | Larson | D24/225 |
| 5,662,127 A | 9/1997 | De Vaughn | 128/765 |
| 5,662,672 A | 9/1997 | Pambianchi | 606/181 |
| 5,666,966 A | 9/1997 | Horie | 128/760 |
| 5,676,143 A | 10/1997 | Simonsen | 128/633 |
| 5,678,306 A | 10/1997 | Bozeman | 29/888.025 |
| 5,680,858 A | 10/1997 | Henrik-Egesborg | 128/635 |
| 5,680,872 A | 10/1997 | Sesekura | 128/760 |
| 5,682,233 A | 10/1997 | Brinda | 356/246 |
| 5,682,884 A | 11/1997 | Hill | 128/637 |
| 5,683,562 A | 11/1997 | Schaffar | 204/403 |
| 5,691,898 A | 11/1997 | Rosenberg | 700/85 |
| 5,692,514 A | 12/1997 | Bowman | 600/504 |
| 5,695,947 A | 12/1997 | Guo | 435/11 |
| 5,700,695 A | 12/1997 | Yassinzadeh | 436/180 |
| 5,705,045 A | 1/1998 | Park | 204/403 |
| 5,707,384 A | 1/1998 | Kim | 606/181 |
| 5,708,247 A | 1/1998 | McAleer | 204/403 |
| 5,709,668 A | 1/1998 | Wacks | 604/232 |
| 5,709,699 A | 1/1998 | Warner | 606/181 |
| 5,710,011 A | 1/1998 | Forrow | 435/25 |
| 5,714,123 A | 2/1998 | Sohrab | 422/99 |
| 5,714,390 A | 2/1998 | Hallowitz | 436/526 |
| 5,719,034 A | 2/1998 | Kiser | 435/14 |
| 5,720,862 A | 2/1998 | Hamamoto | 204/403 |
| 5,720,924 A | 2/1998 | Eikmeier | 422/102 |
| D392,391 S | 3/1998 | Douglas | D24/225 |
| D392,740 S | 3/1998 | Yung | D24/169 |
| 5,723,284 A | 3/1998 | Ye | 435/4 |
| 5,727,548 A | 3/1998 | Hill | 128/637 |
| 5,729,905 A | 3/1998 | Mathiasmeier | 33/3 R |
| 5,730,753 A | 3/1998 | Susumu | 606/181 |
| 5,733,085 A | 3/1998 | Shida | 411/442 |
| 5,733,300 A | 3/1998 | Pambianchi | 606/181 |
| D393,716 S | 4/1998 | Brenneman | D24/147 |
| D393,717 S | 4/1998 | Brenneman | D24/147 |
| 5,735,868 A | 4/1998 | Lee | 606/189 |
| 5,736,103 A | 4/1998 | Pugh | 422/68.1 |
| 5,738,244 A | 4/1998 | Charlton | 221/26 |
| 5,741,228 A | 4/1998 | Lambrecht | 604/93 |
| 5,741,634 A | 4/1998 | Nozoe | 435/4 |
| RE35,803 E | 5/1998 | Lange | 606/182 |
| 5,746,217 A | 5/1998 | Erickson | 128/760 |
| 5,746,761 A | 5/1998 | Turchin | 606/181 |
| 5,746,898 A | 5/1998 | Preidel | 204/403 |
| 5,753,429 A | 5/1998 | Pugh | 435/4 |
| 5,753,452 A | 5/1998 | Smith | 435/14 |
| 5,755,228 A | 5/1998 | Wilson | 600/459 |
| 5,755,733 A | 5/1998 | Susumu | 606/182 |
| 5,758,643 A | 6/1998 | Wong | 600/309 |
| 5,759,364 A | 6/1998 | Charlton | 204/403 |
| 5,762,770 A | 6/1998 | Pritchard | 204/403 |
| 5,770,086 A | 6/1998 | Indriksons | 210/643 |
| 5,770,369 A | 6/1998 | Meade | 435/6 |
| 5,772,586 A | 6/1998 | Heinonen | 600/300 |
| 5,772,677 A | 6/1998 | Mawhirt | 606/181 |
| 5,773,270 A | 6/1998 | D'Orazio | 435/177 |
| 5,776,157 A | 7/1998 | Thorne | 606/182 |
| 5,776,719 A | 7/1998 | Douglas | 435/28 |
| 5,779,365 A | 7/1998 | Takaki | 374/161 |
| 5,780,304 A | 7/1998 | Matzinger | 436/169 |
| 5,782,770 A | 7/1998 | Mooradian | 600/476 |
| 5,782,852 A | 7/1998 | Foggia | 606/182 |
| 5,788,651 A | 8/1998 | Weilandt | 600/567 |
| 5,788,652 A | 8/1998 | Rahn | 600/577 |
| 5,789,255 A | 8/1998 | Yu | 536/95 |
| 5,794,219 A | 8/1998 | Brown | 705/37 |
| 5,795,725 A | 8/1998 | Buechler | 435/7.1 |
| 5,795,774 A | 8/1998 | Matsumoto | 435/287.9 |
| 5,797,940 A | 8/1998 | Mawhirt | 606/167 |

(56) References Cited

U.S. PATENT DOCUMENTS

| | | | |
|---|---|---|---|
| 5,797,942 A | 8/1998 | Schraga | 606/182 |
| 5,798,030 A | 8/1998 | Raguse | 204/403 |
| 5,798,031 A | 8/1998 | Charlton | 204/403 |
| 5,800,781 A | 9/1998 | Gavin | 422/73 |
| 5,801,057 A | 9/1998 | Smart | 436/68 |
| 5,807,375 A | 9/1998 | Gross | 604/890.1 |
| 5,810,199 A | 9/1998 | Charlton | 221/31 |
| D399,566 S | 10/1998 | Sohrab | D24/169 |
| 5,820,551 A | 10/1998 | Hill | 600/347 |
| 5,822,715 A | 10/1998 | Worthington | 702/19 |
| 5,823,973 A | 10/1998 | Racchini | 600/573 |
| 5,824,491 A | 10/1998 | Priest | 435/28 |
| 5,827,181 A | 10/1998 | Dias | 600/322 |
| 5,828,943 A | 10/1998 | Brown | 434/258 |
| 5,829,589 A | 11/1998 | Nguyen | 206/366 |
| 5,830,219 A | 11/1998 | Bird | 606/130 |
| 5,832,448 A | 11/1998 | Brown | 705/2 |
| 5,840,020 A | 11/1998 | Heinonen | 600/309 |
| 5,840,171 A | 11/1998 | Birch | 205/335 |
| 5,843,691 A | 12/1998 | Douglas | 435/14 |
| 5,843,692 A | 12/1998 | Phillips | 435/14 |
| 5,846,216 A | 12/1998 | Gonzales | 604/2 |
| 5,846,486 A | 12/1998 | Pugh | 422/56 |
| 5,846,490 A | 12/1998 | Yokota | 422/66 |
| 5,849,174 A | 12/1998 | Sanghera | 205/775 |
| 5,853,373 A | 12/1998 | Griffith | 600/554 |
| 5,854,074 A | 12/1998 | Charlton | 436/46 |
| 5,855,377 A | 1/1999 | Murphy | 279/50 |
| 5,855,801 A | 1/1999 | Lin | 216/2 |
| 5,856,174 A | 1/1999 | Lipshutz | 435/286.5 |
| 5,856,195 A | 1/1999 | Charlton | 436/50 |
| 5,857,967 A | 1/1999 | Frid | 600/301 |
| 5,857,983 A | 1/1999 | Douglas | 600/538 |
| 5,858,804 A | 1/1999 | Zanzucchi | 506/9 |
| 5,860,922 A | 1/1999 | Gordon et al. | 600/431 |
| 5,863,800 A | 1/1999 | Eikmeier | 436/48 |
| 5,866,353 A | 2/1999 | Berneth | 435/26 |
| 5,868,135 A | 2/1999 | Kaufman | 128/630 |
| 5,868,772 A | 2/1999 | LeVaughn | 606/181 |
| 5,869,972 A | 2/1999 | Birch | 324/439 |
| 5,871,494 A | 2/1999 | Simons | 606/181 |
| 5,872,713 A | 2/1999 | Douglas | 702/85 |
| 5,873,856 A | 2/1999 | Hjertman et al. | |
| 5,873,887 A | 2/1999 | King | 606/182 |
| 5,876,351 A | 3/1999 | Rohde | 600/523 |
| 5,876,957 A | 3/1999 | Douglas | 435/28 |
| 5,879,163 A | 3/1999 | Brown | 434/236 |
| 5,879,310 A | 3/1999 | Sopp | 600/578 |
| 5,879,311 A | 3/1999 | Duchon | 600/583 |
| 5,879,373 A | 3/1999 | Roeper | 606/344 |
| 5,880,829 A | 3/1999 | Kauhaniemi | 356/246 |
| 5,882,494 A | 3/1999 | van Antwerp | 204/403 |
| 5,885,211 A | 3/1999 | Eppstein | 600/309 |
| 5,886,056 A | 3/1999 | Hershkowitz | 518/703 |
| 5,887,133 A | 3/1999 | Brown | 395/200.3 |
| 5,890,128 A | 3/1999 | Diaz | 705/2 |
| RE36,191 E | 4/1999 | Solomon | 395/308 |
| 5,891,053 A | 4/1999 | Sesekura | 600/583 |
| 5,892,569 A | 4/1999 | Van de Velde | 351/221 |
| 5,893,848 A | 4/1999 | Negus | 606/41 |
| 5,893,870 A | 4/1999 | Talen | 606/201 |
| 5,897,493 A | 4/1999 | Brown | 600/300 |
| 5,897,569 A | 4/1999 | Kellogg | 606/169 |
| 5,899,855 A | 5/1999 | Brown | 600/301 |
| 5,899,915 A | 5/1999 | Saadat | 606/170 |
| 5,900,130 A | 5/1999 | Benvegnu | 204/453 |
| 5,902,731 A | 5/1999 | Ouyang | 435/26 |
| 5,906,921 A | 5/1999 | Ikeda | 435/25 |
| D403,975 S | 6/1999 | Douglas | D10/81 |
| D411,619 S | 6/1999 | Duchon | D24/146 |
| 5,908,416 A | 6/1999 | Costello | 606/9 |
| 5,911,937 A | 6/1999 | Hekal | 264/255 |
| 5,912,134 A | 6/1999 | Shartle | 435/7.24 |
| 5,913,310 A | 6/1999 | Brown | 128/897 |
| 5,916,156 A | 6/1999 | Hildenbrand | 600/347 |
| 5,916,229 A | 6/1999 | Evans | 606/171 |
| 5,916,230 A | 6/1999 | Brenneman | 606/172 |
| 5,918,603 A | 7/1999 | Brown | 128/897 |
| 5,919,711 A | 7/1999 | Boyd | 436/178 |
| 5,921,963 A | 7/1999 | Erez | 604/192 |
| 5,922,188 A | 7/1999 | Ikeda | 204/777.5 |
| 5,922,530 A | 7/1999 | Yu | 435/4 |
| 5,922,591 A | 7/1999 | Anderson | 435/287.2 |
| RE36,268 E | 8/1999 | Szuminsky | 205/777.5 |
| 5,931,794 A | 8/1999 | Pitesky | 600/556 |
| 5,933,136 A | 8/1999 | Brown | 345/327 |
| 5,935,075 A | 8/1999 | Casscells et al. | 600/474 |
| 5,938,635 A | 8/1999 | Kuhle | 604/506 |
| 5,938,679 A | 8/1999 | Freeman | 606/181 |
| 5,940,153 A | 8/1999 | Castaneda | 349/58 |
| 5,942,102 A | 8/1999 | Hodges | 205/775 |
| 5,942,189 A | 8/1999 | Wolfbeis | 422/82.08 |
| 5,947,957 A | 9/1999 | Morris | 606/13 |
| 5,951,300 A | 9/1999 | Brown | 434/236 |
| 5,951,492 A | 9/1999 | Douglas | 600/583 |
| 5,951,493 A | 9/1999 | Douglas et al. | 600/583 |
| 5,951,582 A | 9/1999 | Thorne | 606/182 |
| 5,951,836 A | 9/1999 | McAleer | 204/403 |
| 5,954,738 A | 9/1999 | LeVaughn | 606/181 |
| 5,956,501 A | 9/1999 | Brown | 395/500.32 |
| 5,957,846 A | 9/1999 | Chiang | 600/447 |
| 5,958,199 A | 9/1999 | Miyamoto | 204/403 |
| 5,959,098 A | 9/1999 | Goldberg | 536/25.3 |
| 5,960,403 A | 9/1999 | Brown | 705/2 |
| 5,961,451 A | 10/1999 | Reber | 600/322 |
| 5,964,718 A | 10/1999 | Duchon | 600/583 |
| 5,965,380 A | 10/1999 | Heller | 435/14 |
| 5,968,063 A | 10/1999 | Chu | 606/185 |
| 5,968,760 A | 10/1999 | Phillips | 435/14 |
| 5,968,836 A | 10/1999 | Matzinger | 436/169 |
| 5,971,941 A | 10/1999 | Simons | 606/573 |
| 5,972,199 A | 10/1999 | Heller | 205/777.5 |
| 5,972,294 A | 10/1999 | Smith | 422/58 |
| 5,972,715 A | 10/1999 | Celentano | 436/164 |
| 5,974,124 A | 10/1999 | Schlueter | 379/106.02 |
| 5,976,085 A | 11/1999 | Kimball | 600/309 |
| 5,983,193 A | 11/1999 | Heinonen | 705/2 |
| 5,985,116 A | 11/1999 | Ikeda | 204/403 |
| 5,985,559 A | 11/1999 | Brown | 435/6 |
| 5,986,754 A | 11/1999 | Harding | 356/246 |
| 5,993,400 A | 11/1999 | Rincoe | 600/595 |
| 5,993,434 A | 11/1999 | Dev | 604/501 |
| D417,504 S | 12/1999 | Love | D24/169 |
| 5,997,476 A | 12/1999 | Brown | 600/300 |
| 5,997,509 A | 12/1999 | Rosengart et al. | |
| 5,997,561 A | 12/1999 | Boecker | 606/182 |
| 5,997,817 A | 12/1999 | Crismore | 422/58 |
| 5,997,818 A | 12/1999 | Hackner | 422/681 |
| 6,001,067 A | 12/1999 | Shults | 600/584 |
| 6,007,497 A | 12/1999 | Huitema | 600/567 |
| D418,602 S | 1/2000 | Prokop | D24/169 |
| 6,014,577 A | 1/2000 | Henning | 600/345 |
| 6,015,392 A | 1/2000 | Douglas | 600/583 |
| 6,018,289 A | 1/2000 | Sekura | 340/309.4 |
| 6,020,110 A | 2/2000 | Williams | 430/315 |
| 6,022,324 A | 2/2000 | Skinner | 600/566 |
| 6,022,366 A | 2/2000 | Schraga | 606/181 |
| 6,022,748 A | 2/2000 | Charych | 436/527 |
| 6,023,629 A | 2/2000 | Tamada | 600/347 |
| 6,023,686 A | 2/2000 | Brown | 705/37 |
| 6,027,459 A | 2/2000 | Shain | 600/573 |
| 6,030,399 A | 2/2000 | Ignotz | 606/167 |
| 6,030,827 A | 2/2000 | Davis | 435/287 |
| 6,030,967 A | 2/2000 | Marui | 514/215 |
| 6,032,059 A | 2/2000 | Henning | 600/345 |
| 6,032,119 A | 2/2000 | Brown | 705/2 |
| 6,033,421 A | 3/2000 | Theiss | 606/186 |
| 6,033,866 A | 3/2000 | Guo | 435/14 |
| 6,036,924 A | 3/2000 | Simons | 422/100 |
| 6,037,178 A | 3/2000 | Leiner | 436/50 |
| 6,041,253 A | 3/2000 | Kost | 604/20 |
| 6,045,567 A | 4/2000 | Taylor | 606/181 |
| 6,046,055 A | 4/2000 | Wolfbeis | 436/172 |
| 6,048,352 A | 4/2000 | Douglas | 606/181 |

(56) References Cited

U.S. PATENT DOCUMENTS

| | | | |
|---|---|---|---|
| D424,696 S | 5/2000 | Ray | D24/169 |
| 6,056,701 A | 5/2000 | Duchon | 600/583 |
| 6,059,815 A | 5/2000 | Lee | 606/209 |
| 6,060,327 A | 5/2000 | Keen | 436/518 |
| 6,061,128 A | 5/2000 | Zweig | 356/243.4 |
| 6,063,039 A | 5/2000 | Cunningham | 600/573 |
| 6,066,103 A | 5/2000 | Duchon | 600/583 |
| 6,066,243 A | 5/2000 | Anderson | 422/82.01 |
| 6,066,296 A | 5/2000 | Brady | 422/63 |
| 6,067,463 A | 5/2000 | Jeng | 600/336 |
| 6,068,615 A | 5/2000 | Brown | 604/207 |
| D426,638 S | 6/2000 | Ray | D24/169 |
| 6,070,761 A | 6/2000 | Bloom | 222/81 |
| 6,071,249 A | 6/2000 | Cunningham | 600/578 |
| 6,071,250 A | 6/2000 | Douglas | 600/583 |
| 6,071,251 A | 6/2000 | Cunningham | 600/584 |
| 6,071,294 A | 6/2000 | Simons | 606/181 |
| 6,071,391 A | 6/2000 | Gotoh | 204/403 |
| 6,074,360 A | 6/2000 | Hans-Peter | 604/57 |
| 6,077,408 A | 6/2000 | Miyamoto | 204/403 |
| 6,080,106 A | 6/2000 | Lloyd | 600/300 |
| 6,080,172 A | 6/2000 | Fujiwara | 606/166 |
| D428,150 S | 7/2000 | Ruf | D24/146 |
| 6,083,196 A | 7/2000 | Trautman | 604/46 |
| 6,083,710 A | 7/2000 | Heller | 435/14 |
| 6,084,660 A | 7/2000 | Shartle | 356/39 |
| 6,085,576 A | 7/2000 | Sunshine | 73/29.01 |
| 6,086,544 A | 7/2000 | Hibner | 600/568 |
| 6,086,545 A | 7/2000 | Roe | 600/570 |
| 6,086,562 A | 7/2000 | Jacobsen | 604/156 |
| 6,090,078 A | 7/2000 | Erskine | 604/198 |
| 6,091,975 A | 7/2000 | Daddona | 600/345 |
| 6,093,146 A | 7/2000 | Filangeri | 600/300 |
| 6,093,156 A | 7/2000 | Cunningham et al. | 600/573 |
| D428,993 S | 8/2000 | Lubs | D24/165 |
| 6,099,484 A | 8/2000 | Douglas | 600/583 |
| 6,099,802 A | 8/2000 | Pugh | 422/58 |
| 6,100,107 A | 8/2000 | Lei | 438/50 |
| 6,101,478 A | 8/2000 | Brown | 705/2 |
| 6,102,933 A | 8/2000 | Lee | 606/209 |
| 6,103,033 A | 8/2000 | Say | 156/73.1 |
| 6,103,509 A | 8/2000 | Sode | 435/190 |
| 6,104,940 A | 8/2000 | Watanabe | 600/345 |
| 6,106,751 A | 8/2000 | Talbot | 264/81 |
| 6,107,083 A | 8/2000 | Collins | 435/288 |
| 6,113,578 A | 9/2000 | Brown | 604/207 |
| 6,117,115 A | 9/2000 | Lee | 606/189 |
| 6,117,630 A | 9/2000 | Reber | 435/4 |
| 6,118,126 A | 9/2000 | Zanzucchi | 250/458.1 |
| 6,119,033 A | 9/2000 | Spigelman | 600/426 |
| 6,120,462 A | 9/2000 | Hibner | 600/566 |
| 6,120,676 A | 9/2000 | Heller | 205/777.5 |
| 6,121,009 A | 9/2000 | Heller | 435/14 |
| 6,122,536 A | 9/2000 | Sun | 600/341 |
| 6,126,804 A | 10/2000 | Andresen | 204/601 |
| 6,126,899 A | 10/2000 | Woudenberg | 422/50 |
| 6,129,823 A | 10/2000 | Hughes | 204/403.01 |
| 6,132,449 A | 10/2000 | Lum | 606/181 |
| 6,133,837 A | 10/2000 | Riley | 340/573.1 |
| 6,134,461 A | 10/2000 | Say | 600/345 |
| 6,136,013 A | 10/2000 | Marshall | 606/167 |
| 6,139,562 A | 10/2000 | Mauze | 606/171 |
| 6,143,164 A | 11/2000 | Heller | 600/583 |
| 6,144,144 A | 11/2000 | Quy | 434/307 R |
| 6,144,976 A | 11/2000 | Silva et al. | 708/100 |
| 6,149,203 A | 11/2000 | Hanlon | 283/72 |
| 6,151,586 A | 11/2000 | Brown | 705/14 |
| 6,152,875 A | 11/2000 | Hakamata | 600/319 |
| 6,152,942 A | 11/2000 | Brenneman | 606/181 |
| 6,153,069 A | 11/2000 | Pottgen | 204/403 |
| RE36,991 E | 12/2000 | Yamamoto | 204/403 |
| 6,155,267 A | 12/2000 | Nelson | 128/899 |
| 6,155,992 A | 12/2000 | Henning et al. | 600/583 |
| 6,156,051 A | 12/2000 | Schraga | 606/181 |
| 6,157,442 A | 12/2000 | Raskas | 356/39 |
| 6,159,147 A | 12/2000 | Lichter | 600/300 |
| 6,159,424 A | 12/2000 | Kauhaniemi | 422/63 |
| 6,161,095 A | 12/2000 | Brown | 705/2 |
| 6,162,397 A | 12/2000 | Jurik | 422/56 |
| 6,162,611 A | 12/2000 | Heller | 435/14 |
| 6,167,362 A | 12/2000 | Brown | 703/11 |
| 6,167,386 A | 12/2000 | Brown | 705/37 |
| 6,168,563 B1 | 1/2001 | Brown | 600/301 |
| 6,168,957 B1 | 1/2001 | Matzinger | 436/518 |
| 6,171,325 B1 | 1/2001 | Mauze et al. | 606/171 |
| 6,172,743 B1 | 1/2001 | Kley et al. | 356/39 |
| 6,175,752 B1 | 1/2001 | Say | 600/345 |
| 6,176,847 B1 | 1/2001 | Humphreys | 604/246 |
| 6,176,865 B1 | 1/2001 | Mauze | 606/171 |
| 6,177,000 B1 | 1/2001 | Peterson | 205/777.5 |
| 6,177,931 B1 | 1/2001 | Alexander | 725/52 |
| 6,183,489 B1 | 2/2001 | Douglas | 606/181 |
| 6,186,145 B1 | 2/2001 | Brown | 128/897 |
| 6,190,612 B1 | 2/2001 | Berger | 422/82.07 |
| 6,191,852 B1 | 2/2001 | Paffhausen | 356/244 |
| 6,192,891 B1 | 2/2001 | Gravel | 128/920 |
| 6,193,673 B1 | 2/2001 | Viola | 600/568 |
| 6,193,873 B1 | 2/2001 | Ohara | 205/792 |
| 6,194,900 B1 | 2/2001 | Freeman | 324/321 |
| 6,197,040 B1 | 3/2001 | LeVaughn | 606/182 |
| 6,197,257 B1 | 3/2001 | Raskas | 422/82.05 |
| 6,200,289 B1 | 3/2001 | Hochman et al. | |
| 6,200,773 B1 | 3/2001 | Ouyang | 435/26 |
| 6,203,504 B1 | 3/2001 | Latterell | 600/576 |
| 6,206,841 B1 | 3/2001 | Cunningham et al. | 600/584 |
| 6,210,133 B1 | 4/2001 | Aboul-Hosn | 417/423.1 |
| 6,210,272 B1 | 4/2001 | Brown | 463/1 |
| 6,210,369 B1 | 4/2001 | Wilmot | 604/157 |
| 6,210,420 B1 | 4/2001 | Mauze | 606/182 |
| 6,210,421 B1 | 4/2001 | Bocker | 606/182 |
| 6,212,417 B1 | 4/2001 | Ikeda | 204/403.14 |
| 6,214,626 B1 | 4/2001 | Meller | 436/165 |
| 6,214,804 B1 | 4/2001 | Felgner | 514/44 |
| 6,218,571 B1 | 4/2001 | Zheng | 562/61 |
| 6,219,574 B1 | 4/2001 | Cormier | 604/20 |
| 6,221,023 B1 | 4/2001 | Matsuba | 600/486 |
| 6,221,238 B1 | 4/2001 | Grundig | 205/777.5 |
| 6,224,617 B1 | 5/2001 | Saadat et al. | 606/170 |
| 6,225,078 B1 | 5/2001 | Ikeda | 435/25 |
| 6,228,100 B1 | 5/2001 | Schraga | 606/183 |
| 6,230,051 B1 | 5/2001 | Cormier | 604/20 |
| 6,230,501 B1 | 5/2001 | Bailey | 62/51.1 |
| 6,231,531 B1 | 5/2001 | Lum | 601/46 |
| 6,233,471 B1 | 5/2001 | Berner | 600/345 |
| 6,233,539 B1 | 5/2001 | Brown | 703/11 |
| 6,234,772 B1 | 5/2001 | Wampler | 417/423.12 |
| 6,238,926 B1 | 5/2001 | Liu et al. | 600/573 |
| 6,240,393 B1 | 5/2001 | Brown | 705/1 |
| D444,235 S | 6/2001 | Roberts | D24/169 |
| 6,241,862 B1 | 6/2001 | McAleer | 204/403 |
| 6,242,207 B1 | 6/2001 | Douglas | 435/25 |
| 6,245,060 B1 | 6/2001 | Loomis | 606/9 |
| 6,245,215 B1 | 6/2001 | Douglas | 205/775 |
| 6,246,992 B1 | 6/2001 | Brown | 705/2 |
| 6,248,065 B1 | 6/2001 | Brown | 600/300 |
| 6,251,083 B1 | 6/2001 | Yum | 600/584 |
| 6,251,121 B1 | 6/2001 | Saadat | 606/180 |
| 6,251,260 B1 | 6/2001 | Heller | 205/777.5 |
| 6,251,344 B1 | 6/2001 | Goldstein | 422/123 |
| D444,557 S | 7/2001 | Levaughn | D24/146 |
| 6,254,831 B1 | 7/2001 | Barnard | 422/82.08 |
| 6,256,533 B1 | 7/2001 | Vuzhakov | 604/21 |
| 6,258,111 B1 | 7/2001 | Ross | 606/171 |
| 6,258,229 B1 | 7/2001 | Winarta | 204/403 |
| 6,258,254 B1 | 7/2001 | Miyamoto | 205/777.5 |
| 6,261,241 B1 | 7/2001 | Burbank | 600/564 |
| 6,261,245 B1 | 7/2001 | Kawai | 600/576 |
| 6,261,519 B1 | 7/2001 | Harding | 422/58 |
| 6,264,635 B1 | 7/2001 | Wampler | 604/151 |
| 6,268,161 B1 | 7/2001 | Han | 435/14 |
| 6,268,162 B1 | 7/2001 | Phillips | 435/14 |
| 6,269,314 B1 | 7/2001 | Iitawaki | 702/23 |
| 6,270,455 B1 | 8/2001 | Brown | 600/300 |
| 6,270,637 B1 | 8/2001 | Crismore | 204/403 |

(56) References Cited

U.S. PATENT DOCUMENTS

| | | | |
|---|---|---|---|
| 6,272,359 B1 | 8/2001 | Kivela | 455/567 |
| 6,272,364 B1 | 8/2001 | Kurnik | 600/345 |
| 6,275,717 B1 | 8/2001 | Gross | 600/345 |
| 6,280,254 B1 | 8/2001 | Wu | 439/630 |
| 6,281,006 B1 | 8/2001 | Heller | 435/287.9 |
| 6,283,926 B1 | 9/2001 | Cunningham | 600/573 |
| 6,283,982 B1 | 9/2001 | Levaughn | 606/172 |
| 6,284,478 B1 | 9/2001 | Heller | 435/14 |
| 6,285,448 B1 | 9/2001 | Kuenstner | 356/39 |
| 6,285,454 B1 | 9/2001 | Douglas | 356/446 |
| 6,289,254 B1 | 9/2001 | Shimizu | 700/96 |
| 6,290,683 B1 | 9/2001 | Erez | 604/273 |
| 6,294,897 B1 | 9/2001 | Champlin | 320/153 |
| 6,295,506 B1 | 9/2001 | Heinonen | 702/104 |
| 6,299,578 B1 | 10/2001 | Kurnik | 600/309 |
| 6,299,596 B1 | 10/2001 | Ding | 604/96.01 |
| 6,299,757 B1 | 10/2001 | Feldman | 205/775 |
| 6,302,844 B1 | 10/2001 | Walker | 600/300 |
| 6,302,855 B1 | 10/2001 | Lav | 600/584 |
| 6,305,804 B1 | 10/2001 | Rice | 351/221 |
| 6,306,104 B1 | 10/2001 | Cunningham | 600/573 |
| 6,306,152 B1 | 10/2001 | Verdonk | 606/172 |
| 6,306,347 B1 | 10/2001 | Mason | 422/58 |
| 6,309,351 B1 | 10/2001 | Kurnik | 600/309 |
| 6,309,370 B1 | 10/2001 | Haim et al. | |
| 6,309,535 B1 | 10/2001 | Williams | 205/777.5 |
| 6,312,612 B1 | 11/2001 | Sherman | 216/2 |
| 6,315,738 B1 * | 11/2001 | Nishikawa | A61B 5/1411 600/583 |
| 6,318,970 B1 | 11/2001 | Backhouse | 417/92 |
| 6,319,210 B1 | 11/2001 | Douglas | 600/583 |
| 6,322,574 B1 | 11/2001 | Lloyd | 606/181 |
| 6,322,808 B1 | 11/2001 | Trautman | 424/448 |
| 6,322,963 B1 | 11/2001 | Bauer | 435/4 |
| 6,329,161 B1 | 12/2001 | Heller | 435/14 |
| 6,330,426 B2 | 12/2001 | Brown | 434/307 R |
| 6,331,163 B1 | 12/2001 | Kaplan | 600/486 |
| 6,332,871 B1 | 12/2001 | Douglas | 600/583 |
| 6,334,363 B1 | 1/2002 | Testud | 73/862 |
| 6,334,778 B1 | 1/2002 | Brown | 434/258 |
| 6,334,856 B1 | 1/2002 | Allen | 604/191 |
| 6,335,203 B1 | 1/2002 | Patel | 436/169 |
| 6,335,856 B1 | 1/2002 | Allen | 604/191 |
| 6,336,900 B1 | 1/2002 | Alleckson | 600/485 |
| 6,338,790 B1 | 1/2002 | Feldman | 205/777.5 |
| 6,346,120 B1 | 2/2002 | Yamazaki | 623/3.13 |
| 6,349,229 B1 | 2/2002 | Watanabe | 600/345 |
| 6,350,273 B1 | 2/2002 | Minagawa | 606/186 |
| 6,350,451 B1 | 2/2002 | Horn | 424/184.1 |
| 6,352,514 B1 | 3/2002 | Douglas | 600/583 |
| 6,352,523 B1 | 3/2002 | Brown | 604/207 |
| 6,353,753 B1 | 3/2002 | Flock | 600/473 |
| 6,358,196 B1 | 3/2002 | Rayman | |
| 6,364,889 B1 | 4/2002 | Kheiri et al. | 606/181 |
| 6,364,890 B1 | 4/2002 | Lum | 606/181 |
| 6,368,273 B1 | 4/2002 | Brown | 600/300 |
| 6,375,469 B1 | 4/2002 | Brown | 434/236 |
| 6,375,626 B1 | 4/2002 | Allen et al. | 600/584 |
| 6,375,627 B1 | 4/2002 | Mauze | 600/584 |
| 6,379,301 B1 | 4/2002 | WOrthington | 600/309 |
| 6,379,317 B1 | 4/2002 | Kintzig | 600/573 |
| 6,379,324 B1 | 4/2002 | Gartstein | 604/22 |
| 6,379,969 B1 | 4/2002 | Mauze | 436/68 |
| 6,381,577 B1 | 4/2002 | Brown | 705/2 |
| D456,910 S | 5/2002 | Clark | D24/225 |
| 6,387,709 B1 | 5/2002 | Mason | 436/164 |
| 6,391,005 B1 | 5/2002 | Lum | 604/117 |
| 6,395,227 B1 | 5/2002 | Kiser | 422/56 |
| 6,398,522 B2 | 6/2002 | Skill | 417/410.3 |
| 6,398,562 B1 | 6/2002 | Butler | 439/91 |
| 6,399,394 B1 | 6/2002 | Dahm | 436/180 |
| 6,402,701 B1 | 6/2002 | Kaplan | 600/567 |
| 6,402,704 B1 | 6/2002 | Mcmorrow | 600/576 |
| 6,409,740 B1 | 6/2002 | Kuhr | 606/182 |
| 6,413,410 B1 | 7/2002 | Hodges | 205/775 |
| 6,413,411 B1 | 7/2002 | Pottgen | 205/777.5 |
| 6,415,821 B2 | 7/2002 | Kamholz | 137/827 |
| 6,419,661 B1 | 7/2002 | Kuhr et al. | |
| 6,420,128 B1 | 7/2002 | Ouyang | 435/14 |
| 6,421,633 B1 | 7/2002 | Heinonen | 703/11 |
| 6,423,014 B1 | 7/2002 | Churchill | 600/587 |
| 6,428,664 B1 | 8/2002 | Bhullar | 204/403.03 |
| 6,436,055 B1 | 8/2002 | Roe | 600/584 |
| 6,436,256 B1 | 8/2002 | Williams | 204/403.06 |
| 6,436,721 B1 | 8/2002 | Kuo | 436/514 |
| 6,440,645 B1 | 8/2002 | Yon-Hin | 430/322 |
| 6,444,115 B1 | 9/2002 | Hodges | 205/792 |
| 6,447,119 B1 | 9/2002 | Stewart et al. | 351/212 |
| 6,447,265 B1 | 9/2002 | Antaki | 417/354 |
| 6,451,040 B1 | 9/2002 | Purcell | 606/181 |
| 6,453,810 B1 | 9/2002 | Rossmeisl | 101/123 |
| 6,458,258 B2 | 10/2002 | Taniike | 204/403 |
| 6,461,496 B1 | 10/2002 | Feldman | 205/777.5 |
| 6,462,162 B2 | 10/2002 | van Antwerp | 528/77 |
| 6,464,649 B1 | 10/2002 | Duchon | 600/583 |
| 6,471,903 B2 | 10/2002 | Sherman | 264/328.1 |
| 6,472,220 B1 | 10/2002 | Simons | 436/63 |
| 6,475,360 B1 | 11/2002 | Hodges | 204/403.14 |
| 6,475,372 B1 | 11/2002 | Ohara | 205/777.5 |
| 6,475,436 B1 | 11/2002 | Schabbach | 422/64 |
| 6,477,394 B2 | 11/2002 | Rice | 600/318 |
| 6,477,424 B1 | 11/2002 | Thompson | 607/60 |
| 6,484,046 B1 | 11/2002 | Say | 600/345 |
| 6,485,439 B1 | 11/2002 | Roe | 600/578 |
| 6,485,461 B1 | 11/2002 | Mason | 604/132 |
| 6,485,923 B1 | 11/2002 | Yani | 435/14 |
| 6,488,827 B1 | 12/2002 | Shartle | 204/403 |
| 6,488,872 B1 | 12/2002 | Beebe et al. | 264/31 |
| 6,488,891 B1 | 12/2002 | Mason | 422/58 |
| 6,489,052 B1 | 12/2002 | Acker | 600/584 |
| 6,489,133 B2 | 12/2002 | Phillips | 435/14 |
| 6,491,709 B2 | 12/2002 | Sharma | 606/181 |
| 6,491,870 B2 | 12/2002 | Patel | 422/58 |
| 6,494,830 B1 | 12/2002 | Wessel | 600/300 |
| 6,497,845 B1 | 12/2002 | Sacherer | 422/104 |
| 6,501,404 B2 | 12/2002 | Walker | 341/143 |
| 6,501,976 B1 | 12/2002 | Sohrab | 600/347 |
| 6,503,210 B1 | 1/2003 | Hirao | 600/576 |
| 6,503,231 B1 | 1/2003 | Praunsnitz | 604/272 |
| 6,503,290 B1 | 1/2003 | Jarosinski | 75/252 |
| 6,503,381 B1 | 1/2003 | Gotoh | 204/403.14 |
| 6,506,165 B1 | 1/2003 | Sweeney | 600/562 |
| 6,506,168 B1 | 1/2003 | Fathallah | 600/578 |
| 6,506,575 B1 | 1/2003 | Knappe | 435/25 |
| 6,508,795 B1 | 1/2003 | Eppstein | 604/113 |
| 6,512,986 B1 | 1/2003 | Harmon | 702/84 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,521,110 B1 | 2/2003 | Hodges | 204/403.14 |
| 6,521,182 B1 | 2/2003 | Shartle | 422/58 |
| 6,527,521 B2 | 3/2003 | Noda | 417/355 |
| 6,527,716 B1 | 3/2003 | Epstein | 600/309 |
| 6,527,778 B2 | 3/2003 | Athanasiou | 606/80 |
| 6,529,377 B1 | 3/2003 | Nelson | 361/699 |
| 6,530,892 B1 | 3/2003 | Kelly | 600/583 |
| 6,530,937 B1 | 3/2003 | Schraga | 606/182 |
| 6,531,322 B1 | 3/2003 | Jurik | 436/95 |
| 6,533,949 B1 | 3/2003 | Yeshurun | 216/11 |
| 6,537,207 B1 | 3/2003 | Rice | 600/121 |
| 6,537,242 B1 | 3/2003 | Palmer | 604/22 |
| 6,537,264 B1 | 3/2003 | Cormier et al. | 604/506 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,541,266 B2 | 4/2003 | Modzelewski | 436/95 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller | 205/777.5 |
| 6,553,244 B2 | 4/2003 | Lesho | 600/347 |
| 6,554,381 B2 | 4/2003 | Locher | 347/7 |

(56) References Cited

U.S. PATENT DOCUMENTS

| | | | |
|---|---|---|---|
| 6,555,061 B1 | 4/2003 | Leong | 422/58 |
| D475,136 S | 5/2003 | Taniguchi | D24/165 |
| 6,558,320 B1 | 5/2003 | Causey | 600/300 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,560,471 B1 | 5/2003 | Heller | 600/347 |
| 6,561,978 B1 | 5/2003 | Conn | 600/309 |
| 6,561,989 B2 | 5/2003 | Whitson | 600/573 |
| 6,562,210 B1 | 5/2003 | Bhullar | 204/403.3 |
| 6,565,509 B1 | 5/2003 | Say | 600/365 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,572,822 B2 | 6/2003 | Jurik | 422/56 |
| 6,574,490 B2 | 6/2003 | Abbink | 600/316 |
| 6,575,905 B2 | 6/2003 | Knobbe | 600/365 |
| 6,576,101 B1 | 6/2003 | Heller | 204/403.14 |
| 6,576,117 B1 | 6/2003 | Kazuo | 205/777.5 |
| 6,576,416 B2 | 6/2003 | Haviland | 435/4 |
| 6,579,690 B1 | 6/2003 | Bonnecaze et al. | 435/14 |
| 6,582,573 B2 | 6/2003 | Douglas | 204/403.1 |
| 6,584,338 B1 | 6/2003 | Van Muiswinkel | 600/419 |
| D477,670 S | 7/2003 | Jurik | D24/225 |
| 6,586,199 B2 | 7/2003 | Ouyang | 435/26 |
| 6,587,705 B1 | 7/2003 | Kim | 600/347 |
| 6,589,260 B1 | 7/2003 | Schmelzeisen-R | 606/181 |
| 6,589,261 B1 | 7/2003 | Abulhaj | 606/181 |
| 6,591,124 B2 | 7/2003 | Sherman et al. | 600/345 |
| 6,591,125 B1 | 7/2003 | Buse | 600/347 |
| 6,592,744 B1 | 7/2003 | Hodges | 205/775 |
| 6,592,745 B1 | 7/2003 | Feldman | 205/777.5 |
| 6,595,919 B2 | 7/2003 | Berner | 600/365 |
| 6,599,281 B1 | 7/2003 | Struys et al. | |
| 6,599,407 B2 | 7/2003 | Taniike | 204/403.1 |
| 6,599,693 B1 | 7/2003 | Webb | 435/4 |
| 6,599,769 B2 | 7/2003 | Kondo | 438/28 |
| 6,601,534 B2 | 8/2003 | Hebrank | 119/6.8 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,604,050 B2 | 8/2003 | Trippel | 702/19 |
| 6,607,362 B2 | 8/2003 | Lum | 417/53 |
| 6,607,494 B1 | 8/2003 | Fowler | 600/570 |
| 6,607,658 B1 | 8/2003 | Heller | 205/777.5 |
| 6,612,111 B1 | 9/2003 | Hodges | 60/593 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,620,310 B1 | 9/2003 | Ohara | 205/792 |
| 6,623,501 B2 | 9/2003 | Heller | 606/181 |
| 6,626,851 B1 | 9/2003 | Hirao | 600/576 |
| 6,632,349 B1 | 10/2003 | Hodges | 205/792 |
| 6,635,222 B2 | 10/2003 | Kent | 422/22 |
| 6,638,415 B1 | 10/2003 | Hodges | 205/775 |
| 6,638,772 B1 | 10/2003 | Douglas | 436/518 |
| 6,641,533 B2 | 11/2003 | Causey | 600/300 |
| 6,645,142 B2 | 11/2003 | Braig | 600/300 |
| 6,645,219 B2 | 11/2003 | Roe | 606/182 |
| 6,645,368 B1 | 11/2003 | Beatty | 205/792 |
| 6,649,416 B1 | 11/2003 | Kauer | 436/164 |
| 6,650,915 B2 | 11/2003 | Routt | 600/319 |
| 6,652,720 B1 | 11/2003 | Mansouri | 204/403.11 |
| 6,652,734 B1 | 11/2003 | Hodges | 205/777.5 |
| 6,652,814 B1 | 11/2003 | House | 422/104 |
| D484,600 S | 12/2003 | Kaar | D24/169 |
| 6,656,428 B1 | 12/2003 | Clark et al. | 422/404 |
| 6,656,697 B1 | 12/2003 | Ouyang | 435/7.9 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,662,439 B1 | 12/2003 | Bhullar | 29/825 |
| 6,669,669 B2 | 12/2003 | Flaherty | 604/132 |
| 6,671,527 B2 | 12/2003 | Peterson | 600/316 |
| D484,980 S | 1/2004 | Hartwein | D24/165 |
| 6,673,617 B2 | 1/2004 | Patel | 436/8 |
| 6,676,995 B2 | 1/2004 | Dick | 427/286 |
| 6,679,841 B2 | 1/2004 | Bojan | 600/309 |
| 6,679,852 B1 | 1/2004 | Schmelzeisen-R | 600/583 |
| 6,682,933 B2 | 1/2004 | Patel | 436/8 |
| 6,689,411 B2 | 2/2004 | Dick | 427/2.13 |
| 6,706,000 B2 | 3/2004 | Perez | 600/583 |
| 6,706,049 B2 | 3/2004 | Moerman | 606/181 |
| 6,706,159 B2 | 3/2004 | Moerman | 204/403.03 |
| 6,706,232 B2 | 3/2004 | Hasegawa | 264/403.09 |
| 6,709,692 B2 | 3/2004 | Sudor | 427/2.1 |
| 6,713,660 B1 | 3/2004 | Roe | 604/361 |
| 6,716,577 B1 | 4/2004 | Yu | 435/6 |
| 6,719,887 B2 | 4/2004 | Hasegawa | 204/403.09 |
| 6,719,923 B2 | 4/2004 | Stiene | 252/511 |
| 6,721,586 B2 | 4/2004 | Kiser | 600/345 |
| 6,723,046 B2 | 4/2004 | Lichtenstein | 600/300 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,729,546 B2 | 5/2004 | Roustaei | 235/462.45 |
| 6,730,494 B1 | 5/2004 | Toranto | 435/28 |
| 6,731,966 B1 | 5/2004 | Spigelman | 600/407 |
| 6,733,493 B2 | 5/2004 | Gruzdev | 606/9 |
| 6,736,777 B2 | 5/2004 | Kim | 600/365 |
| 6,738,654 B2 | 5/2004 | Sohrab | 600/345 |
| 6,740,215 B1 | 5/2004 | Yamamoto | 204/403.14 |
| 6,743,211 B1 | 6/2004 | PraUSnitz | 604/239 |
| 6,743,597 B1 | 6/2004 | Guo | 435/14 |
| 6,743,635 B2 | 6/2004 | Neel | 436/95 |
| 6,745,750 B2 | 6/2004 | Egler et al. | 435/14 |
| 6,746,872 B2 | 6/2004 | Zheng | 436/16 |
| 6,749,618 B2 | 6/2004 | Levaughn | 606/182 |
| 6,749,740 B2 | 6/2004 | Liamos | 205/792 |
| 6,749,792 B2 | 6/2004 | Olsen | 264/328.1 |
| 6,749,887 B1 | 6/2004 | Dick | 427/2.13 |
| 6,751,491 B2 | 6/2004 | Lew | 600/345 |
| 6,752,817 B2 | 6/2004 | Flora | 606/181 |
| 6,753,187 B2 | 6/2004 | Cizdziel | 436/169 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,499 B1 | 10/2004 | Churchill | 600/587 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,406 B2 | 11/2004 | Grube | 439/66 |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |

(56) References Cited

U.S. PATENT DOCUMENTS

| | | | |
|---|---|---|---|
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |
| 6,821,483 B2 | 11/2004 | Phillips | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,829,507 B1 | 12/2004 | Lidman | 607/19 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,830,934 B1 | 12/2004 | Hardling | 436/166 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 6,835,570 B2 | 12/2004 | Patel | 436/8 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/401 |
| 6,843,254 B2 | 1/2005 | Tapper | 128/898 |
| 6,843,902 B1 | 1/2005 | Penner | 205/76 |
| 6,847,451 B2 | 1/2005 | Pugh | 356/436 |
| 6,849,052 B2 | 2/2005 | Uchigaki | 600/584 |
| 6,849,168 B2 | 2/2005 | Crumly | 204/416 |
| 6,849,216 B2 | 2/2005 | Rappin | 264/134 |
| 6,849,456 B2 | 2/2005 | Patel | 436/8 |
| 6,850,790 B2 | 2/2005 | Berner | 600/347 |
| 6,852,119 B1 | 2/2005 | Abulhaj | 606/182 |
| 6,852,212 B2 | 2/2005 | Maxwell | 205/775 |
| 6,852,500 B1 | 2/2005 | Hoss | 435/14 |
| 6,853,854 B1 | 2/2005 | Proniewicz | 600/319 |
| 6,855,243 B2 | 2/2005 | Khan | 205/777.5 |
| 6,856,125 B2 | 2/2005 | Kermani | 324/71.1 |
| 6,856,928 B2 | 2/2005 | Harmon | 702/84 |
| 6,858,015 B2 | 2/2005 | List | 600/583 |
| 6,858,401 B2 | 2/2005 | Phillips | 435/14 |
| 6,859,738 B2 | 2/2005 | Bush | 702/25 |
| 6,862,466 B2 | 3/2005 | Ackerman | 600/347 |
| 6,862,534 B2 | 3/2005 | Sterling | 702/23 |
| 6,863,800 B2 | 3/2005 | Karinka | 205/777.5 |
| 6,863,801 B2 | 3/2005 | Hodges | 205/792 |
| 6,865,408 B1 | 3/2005 | Abbink | 600/310 |
| 6,866,641 B2 | 3/2005 | Marshall | 600/583 |
| 6,866,675 B2 | 3/2005 | Perez | 606/181 |
| 6,866,758 B2 | 3/2005 | Bhullar | 204/403.2 |
| 6,866,822 B1 | 3/2005 | House | 422/82.05 |
| 6,869,418 B2 | 3/2005 | Marano-Ford | 604/192 |
| 6,872,200 B2 | 3/2005 | Mann | 604/890.1 |
| 6,872,297 B2 | 3/2005 | Mansouri | 205/775 |
| 6,872,298 B2 | 3/2005 | Kermani | 205/777.5 |
| 6,872,299 B2 | 3/2005 | Kermani | 205/777.5 |
| 6,872,358 B2 | 3/2005 | Hagen | 422/61 |
| 6,875,208 B2 | 4/2005 | Santini | 604/890.1 |
| 6,875,223 B2 | 4/2005 | Argauer | 606/181 |
| 6,875,327 B1 | 4/2005 | Miyazaki | 204/403.14 |
| 6,875,613 B2 | 4/2005 | Shartle | 436/63 |
| 6,878,120 B2 | 4/2005 | Roe | 600/583 |
| 6,878,251 B2 | 4/2005 | Hodges | 204/403.14 |
| 6,878,255 B1 | 4/2005 | Wang | 204/452 |
| 6,878,262 B2 | 4/2005 | Taniike | 205/777.5 |
| 6,880,968 B1 | 4/2005 | Haar | 374/131 |
| 6,881,203 B2 | 4/2005 | Delmore | 604/272 |
| 6,881,322 B2 | 4/2005 | Tokunaga | 205/775 |
| 6,881,378 B1 | 4/2005 | Zimmer | 422/58 |
| 6,881,541 B2 | 4/2005 | Petersen | 435/6 |
| 6,881,550 B2 | 4/2005 | Phillips | 435/14 |
| 6,881,551 B2 | 4/2005 | Heller | 435/14 |
| 6,881,578 B2 | 4/2005 | Otake | 436/44 |
| 6,882,940 B2 | 4/2005 | Potts | 702/23 |
| 6,884,592 B2 | 4/2005 | Matzinger | 435/7.1 |
| 6,885,196 B2 | 4/2005 | Taniike | 324/444 |
| 6,885,883 B2 | 4/2005 | Parris | 600/347 |
| 6,887,202 B2 | 5/2005 | Currie | 600/309 |
| 6,887,239 B2 | 5/2005 | Elstrom | 606/41 |
| 6,887,253 B2 | 5/2005 | Curie | 606/181 |
| 6,887,426 B2 | 5/2005 | Phillips | 422/56 |
| 6,887,709 B2 | 5/2005 | Leong | 436/8 |
| 6,889,069 B2 | 5/2005 | Routt | 600/319 |
| 6,890,319 B1 | 5/2005 | Crocker | 604/131 |
| 6,890,421 B2 | 5/2005 | Ohara | 205/777.5 |
| 6,890,484 B2 | 5/2005 | Bautista | 422/58 |
| 6,891,936 B2 | 5/2005 | Kai | 379/106.02 |
| 6,892,085 B2 | 5/2005 | McIvor | 600/347 |
| 6,893,396 B2 | 5/2005 | Schulze | 600/300 |
| 6,893,545 B2 | 5/2005 | Gotoh | 204/403.5 |
| 6,893,552 B1 | 5/2005 | Wang | 205/777.5 |
| 6,895,263 B2 | 5/2005 | Shin | 600/316 |
| 6,895,264 B2 | 5/2005 | Rice | 600/319 |
| 6,895,265 B2 | 5/2005 | Silver | 600/345 |
| 6,896,793 B2 | 5/2005 | Erdosy | 205/775 |
| 6,897,788 B2 | 5/2005 | Khair | 340/870.16 |
| 6,902,905 B2 | 6/2005 | Burson | 435/14 |
| 6,904,301 B2 | 6/2005 | Raskas | 600/310 |
| 6,905,733 B2 | 6/2005 | Russell | 427/393.5 |
| 6,908,008 B2 | 6/2005 | Pugh | 221/135 |
| 6,908,535 B2 | 6/2005 | Rankin | 204/406 |
| 6,908,591 B2 | 6/2005 | MacPhee | 422/22 |
| 6,908,593 B1 | 6/2005 | Shartle | 422/58 |
| 6,911,130 B2 | 6/2005 | Brenneman | 204/400 |
| 6,911,131 B2 | 6/2005 | Miyazaki | 204/403.14 |
| 6,911,621 B2 | 6/2005 | Bhullar | 219/121.69 |
| 6,911,937 B1 | 6/2005 | Sparrow | 342/188 |
| 6,913,210 B2 | 7/2005 | Baasch | 239/407 |
| 6,913,668 B2 | 7/2005 | Matzinger | 156/256 |
| 6,916,410 B2 | 7/2005 | Katsuki | 204/403 |
| 6,918,901 B1 | 7/2005 | Theeuwes | 604/500 |
| 6,918,918 B1 | 7/2005 | Schraga | 606/182 |
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |
| 6,925,393 B1 | 8/2005 | Kalatz | 702/27 |
| 6,929,631 B1 | 8/2005 | Brugger | 604/502 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| RE38,803 E | 9/2005 | Rodgers, Jr. | |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,939,685 B2 | 9/2005 | Ouyang | 435/26 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,953,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |

(56) References Cited

U.S. PATENT DOCUMENTS

| | | | |
|---|---|---|---|
| 6,960,287 B2 | 11/2005 | Charlton | 205/775 |
| 6,960,289 B2 | 11/2005 | Hodges | 205/778 |
| 6,960,323 B2 | 11/2005 | Guo | 422/60 |
| 6,964,871 B2 | 11/2005 | Bell | 436/95 |
| 6,965,791 B1 | 11/2005 | Hitchcock | 600/345 |
| 6,966,880 B2 | 11/2005 | Boecker | 600/583 |
| 6,966,977 B2 | 11/2005 | Hasegawa | 204/403.07 |
| 6,967,105 B2 | 11/2005 | Nomura | 436/169 |
| 6,968,375 B1 | 11/2005 | Brown | 709/224 |
| 6,969,359 B2 | 11/2005 | Duchon | 600/583 |
| 6,969,450 B2 | 11/2005 | Taniike | 204/403.01 |
| 6,969,451 B2 | 11/2005 | Shin | 204/412 |
| 6,973,706 B2 | 12/2005 | Say | 29/595 |
| 6,975,893 B2 | 12/2005 | Say | 600/347 |
| 6,977,032 B2 | 12/2005 | Hasegawa | 204/403.05 |
| 6,977,722 B2 | 12/2005 | Wohlstadter et al. | 356/246 |
| 6,979,544 B2 | 12/2005 | Keen | 435/6 |
| 6,979,571 B2 | 12/2005 | Modzelewski | 436/164 |
| 6,982,027 B2 | 1/2006 | Yagi | 204/403.06 |
| 6,982,431 B2 | 1/2006 | Modlin | 250/573 |
| 6,983,176 B2 | 1/2006 | Gardner | 600/310 |
| 6,983,177 B2 | 1/2006 | Rule | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 * | 1/2006 | Roe | A61B 5/1411 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/345 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,210 B2 | 5/2006 | Hodges | 205/792 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,043,821 B2 | 5/2006 | Hodges | 29/594 |
| 7,044,911 B2 | 5/2006 | Drinan | 600/300 |
| 7,045,046 B2 | 5/2006 | Chambers | 204/400 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,087 B2 | 5/2006 | Jenny | 435/13 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D522,656 S | 6/2006 | Orr | D24/169 |
| D523,555 S | 6/2006 | Loerwald | D24/146 |
| 7,056,425 B2 | 6/2006 | Hasegawa | 204/403.04 |
| 7,056,495 B2 | 6/2006 | Roser | 424/45 |
| 7,058,437 B2 | 6/2006 | Buse | 600/347 |
| 7,059,352 B2 | 6/2006 | Bohm | 137/828 |
| 7,060,059 B2 | 6/2006 | Keith | 604/504 |
| 7,060,168 B2 | 6/2006 | Taniike | 204/403.04 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,079,252 B1 | 7/2006 | Debreezeny | 356/451 |
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,066 B2 | 9/2006 | Schraga | 606/182 |
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,113,172 B2 | 9/2006 | Hohl | 345/168 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |

(56) References Cited

U.S. PATENT DOCUMENTS

| | | | |
|---|---|---|---|
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,550 B2 | 11/2006 | Groth | 206/366 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,034 B2 | 11/2006 | Eppstein | 604/22 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorzyk | 205/792 |
| 7,144,496 B2 | 12/2006 | Meserol | 205/792 |
| 7,144,709 B2 | 12/2006 | Ouyang | 435/7.9 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,156,117 B2 | 1/2007 | Bohm | 137/14 |
| 7,156,810 B2 | 1/2007 | Cho | 600/365 |
| 7,157,723 B2 | 1/2007 | Colvin | 250/458.1 |
| 7,160,251 B2 | 1/2007 | Neel | 600/365 |
| 7,160,313 B2 | 1/2007 | Galloway | 606/167 |
| 7,160,678 B1 | 1/2007 | Kayyem | 435/6 |
| 7,162,289 B2 | 1/2007 | Shah | 600/345 |
| 7,163,616 B2 | 1/2007 | Vreeke | 205/777.5 |
| 7,166,074 B2 | 1/2007 | Reghabi | 600/365 |
| 7,166,208 B2 | 1/2007 | Zweig | 205/777.5 |
| 7,167,734 B2 | 1/2007 | Khalil | 600/310 |
| 7,167,735 B2 | 1/2007 | Uchida | 600/310 |
| 7,167,818 B2 | 1/2007 | Brown | 703/11 |
| 7,169,116 B2 | 1/2007 | Day | 600/583 |
| 7,169,117 B2 | 1/2007 | Allen | 600/584 |
| 7,169,289 B2 | 1/2007 | Schulein | 205/777.5 |
| 7,169,600 B2 | 1/2007 | Hoss | 435/287.1 |
| 7,172,728 B2 | 2/2007 | Otake | 422/58 |
| 7,174,799 B2 | 2/2007 | Berner | 600/347 |
| 7,175,641 B1 | 2/2007 | Schraga | 606/181 |
| 7,175,642 B2 | 2/2007 | Briggs | 606/181 |
| 7,179,233 B2 | 2/2007 | Chang | 600/584 |
| 7,182,910 B2 | 2/2007 | Allen | 422/50 |
| 7,183,068 B2 | 2/2007 | Burson | 435/14 |
| 7,183,102 B2 | 2/2007 | Kasai | 200/51.09 |
| 7,188,034 B2 | 3/2007 | Staib | 702/22 |
| 7,189,576 B2 | 3/2007 | Fukuoka | 436/170 |
| 7,190,988 B2 | 3/2007 | Say | 600/345 |
| 7,192,405 B2 | 3/2007 | DeNuzzio | 600/583 |
| 7,192,450 B2 | 3/2007 | Brauker | 623/23.76 |
| 7,195,704 B2 | 3/2007 | Kermani | 205/777.5 |
| 7,198,606 B2 | 4/2007 | Boecker | 600/583 |
| 7,199,594 B2 | 4/2007 | Kermani | 324/663 |
| 7,202,854 B2 | 4/2007 | Hohl | 345/168 |
| 7,206,620 B2 | 4/2007 | Erickson | 600/310 |
| 7,206,623 B2 | 4/2007 | Blank | 600/344 |
| D542,681 S | 5/2007 | Young | D10/80 |
| 7,211,052 B2 | 5/2007 | Roe | 600/584 |
| 7,211,096 B2 | 5/2007 | Kuhr | 606/182 |
| 7,212,925 B2 | 5/2007 | Genshaw | 702/23 |
| 7,213,720 B2 | 5/2007 | Giraud | 220/839 |
| 7,215,982 B2 | 5/2007 | Oshima | 600/310 |
| 7,215,983 B2 | 5/2007 | Cho | 600/316 |
| 7,223,248 B2 | 5/2007 | Erikson | 600/584 |
| 7,225,008 B1 | 5/2007 | Ward | 600/345 |
| D543,878 S | 6/2007 | Castillo | D10/81 |
| D545,438 S | 6/2007 | Huang | D24/186 |
| 7,225,535 B2 | 6/2007 | Feldman | 29/831 |
| 7,226,414 B2 | 6/2007 | Ballerstadt | 600/365 |
| 7,226,461 B2 | 6/2007 | Boecker | 606/181 |
| 7,226,978 B2 | 6/2007 | Tapsak | 525/296 |
| 7,227,156 B2 | 6/2007 | Colvin | 250/458.1 |
| 7,228,159 B2 | 6/2007 | Petersson | 600/316 |
| 7,228,162 B2 | 6/2007 | Ward | 600/345 |
| 7,228,163 B2 | 6/2007 | Ackerman | 600/347 |
| 7,229,458 B2 | 6/2007 | Freeman | 606/181 |
| 7,232,451 B2 | 6/2007 | Boecker | 606/181 |
| 7,232,510 B2 | 6/2007 | Miyazaki | 204/403.1 |
| 7,233,816 B2 | 6/2007 | Blank | 600/310 |
| 7,235,056 B2 | 6/2007 | Duchon | 600/583 |
| 7,235,170 B2 | 6/2007 | Watanabe | 205/777.5 |
| 7,235,378 B2 | 6/2007 | Yonehara | 435/14 |
| 7,236,812 B1 | 6/2007 | Ballerstadt | 600/316 |
| 7,236,814 B2 | 6/2007 | Shioi | 600/344 |
| D545,705 S | 7/2007 | Voege | D10/81 |
| D546,216 S | 7/2007 | Bolognesi | D10/81 |
| D546,218 S | 7/2007 | Grasso | D10/81 |
| 2,747,138 A1 | 7/2007 | Reghabi | 600/365 |
| 7,238,192 B2 | 7/2007 | List | 606/182 |
| 7,238,534 B1 | 7/2007 | Zimmer | 436/169 |
| 7,241,265 B2 | 7/2007 | Cummings | 600/300 |
| 7,244,264 B2 | 7/2007 | Roe | 606/181 |
| 7,244,265 B2 | 7/2007 | Freeman | 606/181 |
| 7,244,266 B2 | 7/2007 | Garthe | 606/181 |
| 7,247,144 B2 | 7/2007 | Douglas | 600/583 |
| 7,250,037 B2 | 7/2007 | Shermer | 604/134 |
| 7,250,056 B2 | 7/2007 | Hamamoto | 606/181 |
| 7,250,095 B2 | 7/2007 | Black | 204/403.14 |
| 7,250,105 B1 | 7/2007 | Davies | 205/777.5 |
| 7,251,514 B2 | 7/2007 | Cho | 600/316 |
| 7,251,515 B2 | 7/2007 | Cho | 600/316 |
| 7,251,516 B2 | 7/2007 | Walker | 600/316 |
| 7,251,517 B2 | 7/2007 | Cho | 600/316 |
| 7,251,518 B2 | 7/2007 | Herrmann | 600/322 |
| 7,251,573 B2 | 7/2007 | Kondoh | 600/310 |
| 7,252,804 B2 | 8/2007 | Miyashita | 422/104 |
| 7,254,426 B2 | 8/2007 | Cho | 600/316 |
| 7,254,427 B2 | 8/2007 | Cho | 600/316 |
| 7,254,428 B2 | 8/2007 | Cho | 600/316 |
| 7,254,429 B2 | 8/2007 | Schurman | 600/316 |
| 7,254,430 B2 | 8/2007 | Cho | 600/316 |
| 7,254,432 B2 | 8/2007 | Fine | 600/335 |
| 7,258,673 B2 | 8/2007 | Racchini | 600/583 |
| 7,258,693 B2 | 8/2007 | Freeman | 606/181 |
| 7,262,061 B2 | 8/2007 | Petrich | 436/169 |
| 7,264,139 B2 | 9/2007 | Brickwood | 221/270 |
| 7,264,627 B2 | 9/2007 | Perez | 606/181 |
| 7,266,400 B2 | 9/2007 | Fine | 600/316 |
| 7,267,665 B2 | 9/2007 | Steil | 604/131 |
| 7,267,750 B2 | 9/2007 | Watanabe | 204/403.04 |
| 7,270,247 B2 | 9/2007 | Charlton | 221/59 |
| 7,271,912 B2 | 9/2007 | Sterling | 356/436 |
| 7,273,484 B2 | 9/2007 | Thoes | 606/181 |
| 7,276,027 B2 | 10/2007 | Haar | 600/309 |
| 7,276,029 B2 | 10/2007 | Goode | 600/365 |
| 7,276,146 B2 | 10/2007 | Wilsey | 205/792 |
| 7,276,147 B2 | 10/2007 | Wilsey | 205/792 |
| 7,276,380 B2 | 10/2007 | Fukuyama | 436/164 |
| 7,277,740 B2 | 10/2007 | Rohleder | 600/316 |
| 7,278,983 B2 | 10/2007 | Ireland | 604/66 |
| 7,279,130 B2 | 10/2007 | Brown | 422/64 |
| 7,282,058 B2 | 10/2007 | Levin | 606/181 |
| 7,287,318 B2 | 10/2007 | Bhullar | 29/825 |
| 7,288,073 B2 | 10/2007 | Effenhauser | 600/584 |
| 7,288,102 B2 | 10/2007 | Griffin | 606/182 |
| 7,288,174 B2 | 10/2007 | Cui | 204/403.14 |
| 7,289,836 B2 | 10/2007 | Colvin | 600/316 |
| 7,291,117 B2 | 11/2007 | Boecker | 600/583 |
| 7,291,159 B2 | 11/2007 | Schmelzeisen-R | 606/181 |
| 7,291,256 B2 | 11/2007 | Teodorzyk | 205/777.5 |
| 7,291,497 B2 | 11/2007 | Holmes | 435/287.2 |
| 7,294,246 B2 | 11/2007 | Gundel | 204/403.14 |
| 7,295,867 B2 | 11/2007 | Berner | 600/345 |

(56) References Cited

U.S. PATENT DOCUMENTS

| | | | |
|---|---|---|---|
| 7,297,122 B2 | 11/2007 | Boecker | 600/583 |
| 7,297,151 B2 | 11/2007 | Boecker | 606/181 |
| 7,297,152 B2 | 11/2007 | Fukuzawa | 606/181 |
| 7,297,241 B2 | 11/2007 | Kontschieder | 204/403.01 |
| 7,297,248 B2 | 11/2007 | Bae | 205/777.5 |
| 7,297,627 B2 | 11/2007 | Shah | 438/622 |
| 7,299,079 B2 | 11/2007 | Rebec | 600/316 |
| 7,299,080 B2 | 11/2007 | Acosta | 600/316 |
| 7,299,081 B2 | 11/2007 | Mace | 600/345 |
| 7,299,082 B2 | 11/2007 | Feldman | 600/347 |
| 7,300,402 B2 | 11/2007 | Iliff | 600/300 |
| 7,301,629 B2 | 11/2007 | Bambot | 356/337 |
| 7,303,573 B2 | 12/2007 | D'Agostino | 606/181 |
| 7,303,726 B2 | 12/2007 | McAllister | 422/68.1 |
| 7,303,922 B2 | 12/2007 | Jeng | 436/164 |
| 7,305,896 B2 | 12/2007 | Howell | 73/864.02 |
| 7,306,560 B2 | 12/2007 | Iliff | 600/300 |
| 7,308,164 B1 | 12/2007 | Banks | 385/12 |
| 7,308,292 B2 | 12/2007 | Colvin | 600/310 |
| 7,310,542 B2 | 12/2007 | Jeon | 600/344 |
| 7,310,543 B2 | 12/2007 | Smart | 600/345 |
| 7,310,544 B2 | 12/2007 | Brister | 600/345 |
| 7,311,718 B2 | 12/2007 | Schraga | 606/181 |
| 7,311,812 B2 | 12/2007 | Forrow | 204/403.06 |
| 7,312,042 B1 | 12/2007 | Petyt | 435/7.1 |
| 7,313,425 B2 | 12/2007 | Finarov | 600/310 |
| 7,314,453 B2 | 1/2008 | Kuo | 600/584 |
| 7,315,752 B2 | 1/2008 | Kraemer | 600/316 |
| 7,316,700 B2 | 1/2008 | Alden | 606/181 |
| 7,316,766 B2 | 1/2008 | Chen | 204/403.01 |
| 7,316,929 B2 | 1/2008 | Purcell | 436/8 |
| 7,317,938 B2 | 1/2008 | Lorenz | 600/316 |
| 7,317,939 B2 | 1/2008 | Fine | 600/322 |
| 7,320,412 B2 | 1/2008 | Mann | 340/870.07 |
| 7,322,942 B2 | 1/2008 | Roe | 600/583 |
| 7,322,996 B2 | 1/2008 | Taylor | 606/181 |
| 7,322,997 B2 | 1/2008 | Shi | 606/181 |
| 7,322,998 B2 | 1/2008 | Kuhr | 606/182 |
| 7,323,098 B2 | 1/2008 | Miyashita | 205/777.5 |
| 7,323,141 B2 | 1/2008 | Kirchhevel | 422/68.1 |
| 7,323,315 B2 | 1/2008 | Marfurt | 435/7.25 |
| 7,328,052 B2 | 2/2008 | Samsoondar | 600/310 |
| 7,331,931 B2 | 2/2008 | Freeman | 600/583 |
| 7,335,292 B2 | 2/2008 | Hodges | 205/775 |
| 7,335,294 B2 | 2/2008 | Heller | 205/792 |
| 7,337,918 B2 | 3/2008 | Fowler | 221/65 |
| 7,338,639 B2 | 3/2008 | Burke | 422/82.1 |
| 7,343,188 B2 | 3/2008 | Sohrab | 600/345 |
| 7,344,499 B1 | 3/2008 | Prausnitz | 600/309 |
| 7,344,500 B2 | 3/2008 | Talbot | 600/365 |
| 7,344,507 B2 | 3/2008 | Briggs | 600/583 |
| 7,344,626 B2 | 3/2008 | Harding | 204/403.01 |
| 7,347,925 B2 | 3/2008 | Hsieh | 205/777.5 |
| 7,347,926 B2 | 3/2008 | Morita | 205/792 |
| 7,347,973 B2 | 3/2008 | Douglas | 422/61 |
| RE40,198 E | 4/2008 | Buck | 205/777.5 |
| 7,351,213 B2 | 4/2008 | Wong | 600/584 |
| 7,351,323 B2 | 4/2008 | Iketaki | 205/777.5 |
| 7,351,375 B2 | 4/2008 | Noda | 422/82.01 |
| 7,351,770 B2 | 4/2008 | Liu | 525/283 |
| 7,357,808 B2 | 4/2008 | Kennedy | 606/181 |
| 7,357,851 B2 | 4/2008 | Reid | 204/403.04 |
| 7,361,182 B2 | 4/2008 | Fukuda | 606/181 |
| 7,361,307 B2 | 4/2008 | Schartle | 422/82.01 |
| 7,371,247 B2 | 5/2008 | Boecker | 606/181 |
| 7,372,277 B2 | 5/2008 | Diamond | 324/444 |
| 7,374,544 B2 | 5/2008 | Freeman | 600/583 |
| 7,374,546 B2 | 5/2008 | Roe | 600/583 |
| 7,378,007 B2 | 5/2008 | Moerman | 204/403.03 |
| 7,378,720 B2 | 5/2008 | Azarnia | 435/287.2 |
| 7,402,616 B2 | 7/2008 | Rodgers | 523/160 |
| 7,404,815 B2 | 7/2008 | Kollias | 604/501 |
| 7,410,468 B2 | 8/2008 | Freeman | 600/583 |
| 7,429,630 B2 | 9/2008 | Liu | 525/283 |
| 7,431,814 B2 | 10/2008 | Hodges | 204/403.02 |
| 7,431,820 B2 | 10/2008 | Hodges | 205/777.5 |
| 7,438,694 B2 | 10/2008 | Boozer | 600/583 |
| D579,652 S | 11/2008 | Lim | D3/201 |
| D579,653 S | 11/2008 | Lim | D3/201 |
| 7,458,956 B1 | 12/2008 | Adams | |
| 7,462,265 B2 | 12/2008 | Leach | 204/403.14 |
| 7,465,380 B2 | 12/2008 | Rodgers | 204/403.14 |
| 7,468,125 B2 | 12/2008 | Kraft | 205/792 |
| D585,314 S | 1/2009 | Schvetz | D10/78 |
| 7,473,264 B2 | 1/2009 | Allen | 606/181 |
| 7,474,390 B2 | 1/2009 | Robinson | 356/42 |
| 7,474,391 B2 | 1/2009 | Baskeyfield | 356/42 |
| 7,481,776 B2 | 1/2009 | Boecker | 600/583 |
| 7,481,818 B2 | 1/2009 | Allen | 606/181 |
| D586,465 S | 2/2009 | Faulkner | D24/146 |
| D586,466 S | 2/2009 | Smith | D24/186 |
| D586,678 S | 2/2009 | Schvetz | D10/81 |
| D586,916 S | 2/2009 | Faulkner | D24/146 |
| 7,485,128 B2 | 2/2009 | Boecker | 606/181 |
| 7,491,178 B2 | 2/2009 | Boecker | 600/583 |
| 7,498,132 B2 | 3/2009 | Yu | 435/6 |
| 7,501,052 B2 | 3/2009 | Iyengar | 205/777.5 |
| 7,501,093 B2 | 3/2009 | Demelo | 422/58 |
| 7,521,019 B2 | 4/2009 | Polak | 422/82.06 |
| 7,524,293 B2 | 4/2009 | Freeman | 600/583 |
| 7,537,571 B2 | 5/2009 | Freeman | 600/583 |
| 7,547,287 B2 | 6/2009 | Boecker | 600/583 |
| 7,548,772 B2 | 6/2009 | Shartle | 600/345 |
| 7,553,511 B2 | 6/2009 | Hleong | 427/2.28 |
| 7,563,232 B2 | 7/2009 | Freeman | 600/583 |
| D598,126 S | 8/2009 | Alvarez-Icaza | D24/225 |
| 7,572,356 B2 | 8/2009 | Rodgers | 204/403.05 |
| 7,575,558 B2 | 8/2009 | Boecker | 600/573 |
| D600,349 S | 9/2009 | Bell | D24/169 |
| D600,812 S | 9/2009 | Lei | D24/169 |
| D600,813 S | 9/2009 | Bell | D24/169 |
| D601,255 S | 9/2009 | Schvetz | D24/169 |
| D601,258 S | 9/2009 | Bell | D24/169 |
| 7,582,063 B2 | 9/2009 | Wurster | 600/584 |
| 7,582,099 B2 | 9/2009 | Freeman | 606/181 |
| 7,586,590 B2 | 9/2009 | Baskeyfield | 356/42 |
| 7,588,670 B2 | 9/2009 | Rodgers | 204/403.14 |
| 7,589,828 B2 | 9/2009 | Robinson | 356/42 |
| 7,592,151 B2 | 9/2009 | Liu | 435/14 |
| 7,593,097 B2 | 9/2009 | Robinson | 356/42 |
| 7,604,592 B2 | 10/2009 | Freeman | 600/309 |
| 7,604,722 B2 | 10/2009 | Hodges | 204/403.02 |
| 7,608,175 B2 | 10/2009 | Hodges | 204/403.02 |
| 7,618,522 B2 | 11/2009 | Davies | 204/403.14 |
| 7,645,263 B2 | 1/2010 | Angel et al. | |
| 7,648,468 B2 | 1/2010 | Boecker | 600/583 |
| 7,648,469 B2 | 1/2010 | Boecker | 600/583 |
| 7,653,492 B2 | 1/2010 | Davies | 702/22 |
| 7,654,127 B2 | 2/2010 | Krulevitch | 73/1.16 |
| 7,655,119 B2 | 2/2010 | Davies | 204/403.14 |
| 7,665,303 B2 | 2/2010 | Bohm | 60/643 |
| 7,666,287 B2 | 2/2010 | Zhao | 204/600 |
| D611,151 S | 3/2010 | Lei | D24/169 |
| D611,372 S | 3/2010 | Salter | D10/81 |
| D611,489 S | 3/2010 | Bell | D14/486 |
| D611,853 S | 3/2010 | Salter | D10/81 |
| D612,274 S | 3/2010 | Heidemann | D10/78 |
| D612,275 S | 3/2010 | Salter | D10/81 |
| D612,279 S | 3/2010 | Heidemann | D10/103 |
| 7,674,232 B2 | 3/2010 | Boecker | 600/583 |
| 7,682,318 B2 | 3/2010 | Alden | 600/583 |
| 7,713,214 B2 | 5/2010 | Freeman et al. | 600/583 |
| 7,749,174 B2 | 7/2010 | Alden et al. | |
| 7,833,172 B2 | 11/2010 | Hein et al. | 600/583 |
| 7,879,058 B2 | 2/2011 | Ikeda | 606/182 |
| 7,901,365 B2 | 3/2011 | Freeman et al. | 600/583 |
| 7,976,778 B2 | 7/2011 | Drucker et al. | |
| 8,062,235 B2 | 11/2011 | Planman et al. | |
| 8,079,960 B2 | 12/2011 | Briggs et al. | 600/583 |
| 8,162,968 B2 | 4/2012 | Boozer et al. | 606/182 |
| 8,197,421 B2 | 6/2012 | Freeman et al. | |
| 8,206,319 B2 | 6/2012 | Freeman et al. | 600/583 |
| 8,231,548 B2 | 7/2012 | Hoenes | 600/583 |
| 8,251,922 B2 | 8/2012 | List et al. | 600/584 |

(56) References Cited

U.S. PATENT DOCUMENTS

| | | |
|---|---|---|
| 8,282,576 B2 | 10/2012 | Marsot et al. |
| 8,388,639 B2 | 3/2013 | Nicholls et al. |
| 8,491,500 B2 | 7/2013 | Briggs et al. |
| 8,800,781 B1 | 8/2014 | Carlile, Jr. et al. ............ 422/73 |
| 2001/0011157 A1 | 8/2001 | Latterell ...................... 600/576 |
| 2001/0016682 A1 | 8/2001 | Berner ......................... 600/345 |
| 2001/0017269 A1 | 8/2001 | Heller ....................... 205/777.5 |
| 2001/0018353 A1 | 8/2001 | Ishigaki ....................... 455/566 |
| 2001/0023349 A1 | 9/2001 | Van Tassel et al. ............ 606/53 |
| 2001/0027328 A1 | 10/2001 | Lum ............................ 606/186 |
| 2001/0031931 A1 | 10/2001 | Cunningham ................ 600/573 |
| 2001/0037072 A1 | 11/2001 | Virtanen |
| 2001/0037355 A1 | 11/2001 | Britt ............................. 709/201 |
| 2001/0042004 A1 | 11/2001 | Taub ............................. 705/11 |
| 2001/0045355 A1 | 11/2001 | Gephart ........................ 204/400 |
| 2001/0054319 A1 | 12/2001 | Heller ............................ 73/849 |
| 2002/0002326 A1 | 1/2002 | Causey ......................... 600/300 |
| 2002/0002344 A1 | 1/2002 | Douglas ........................ 600/583 |
| 2002/0004196 A1 | 1/2002 | Whitson ....................... 600/573 |
| 2002/0016568 A1 | 2/2002 | Lebel ............................ 604/131 |
| 2002/0016606 A1 | 2/2002 | Moerman ..................... 606/181 |
| 2002/0016923 A1 | 2/2002 | Knaus ........................... 713/200 |
| 2002/0019606 A1 | 2/2002 | Lebel ............................. 604/66 |
| 2002/0019747 A1 | 2/2002 | Ware ............................. 705/2 |
| 2002/0019748 A1 | 2/2002 | Brown ............................ 705/2 |
| 2002/0020646 A1 | 2/2002 | Groth et al. |
| 2002/0025469 A1 | 2/2002 | Heller ............................ 429/43 |
| 2002/0029058 A1 | 3/2002 | Levaughn ..................... 606/181 |
| 2002/0040208 A1 | 4/2002 | Flaherty ................... 604/288.01 |
| 2002/0040230 A1 | 4/2002 | Kuhr ............................. 606/181 |
| 2002/0042090 A1 | 4/2002 | Heller ............................ 435/14 |
| 2002/0042594 A1 | 4/2002 | Lum ............................. 604/117 |
| 2002/0044890 A1 | 4/2002 | Black ............................ 422/56 |
| 2002/1142594 | 4/2002 | Lum Paul et al. |
| 2002/0052618 A1 | 5/2002 | Haar ............................ 606/181 |
| 2002/0053523 A1 | 5/2002 | Liamos ........................ 205/787 |
| 2002/0057993 A1 | 5/2002 | Maisey ..................... 422/82.01 |
| 2002/0058902 A1 | 5/2002 | Kollias et al. ................. 604/20 |
| 2002/0076349 A1 | 6/2002 | Aitken ........................... 422/58 |
| 2002/0078091 A1 | 6/2002 | Vu .............................. 707/513 |
| 2002/0081559 A1 | 6/2002 | Brown ..................... 434/307 R |
| 2002/0081588 A1 | 6/2002 | Lumley-Woodyear ........... 435/6 |
| 2002/0082543 A1 | 6/2002 | Park ............................. 604/21 |
| 2002/0084196 A1 | 7/2002 | Liamos ........................ 205/792 |
| 2002/0087056 A1 | 7/2002 | Aceti |
| 2002/0092612 A1 | 7/2002 | Davies ......................... 156/292 |
| 2002/0099308 A1 | 7/2002 | Bojan ........................... 600/573 |
| 2002/0103499 A1 | 8/2002 | Perez ........................... 606/182 |
| 2002/0111634 A1 | 8/2002 | Stoianovici et al. |
| 2002/0120216 A1 | 8/2002 | Fritz ............................. 600/583 |
| 2002/0120261 A1 | 8/2002 | Morris .......................... 606/41 |
| 2002/0123335 A1 | 9/2002 | Luna ............................ 455/419 |
| 2002/0130042 A1 | 9/2002 | Moerman ................. 204/403.01 |
| 2002/0133377 A1 | 9/2002 | Brown ............................ 705/3 |
| 2002/0136667 A1 | 9/2002 | Subramanian ................ 422/100 |
| 2002/0136863 A1 | 9/2002 | Subramanian ................ 428/156 |
| 2002/0137998 A1 | 9/2002 | Smart .......................... 600/347 |
| 2002/0138040 A1 | 9/2002 | Flora ............................ 604/116 |
| 2002/0141032 A1 | 10/2002 | Guarr et al. ................... 359/265 |
| 2002/0148739 A2 | 10/2002 | Liamos ........................ 205/787 |
| 2002/0156355 A1 | 10/2002 | Gough ......................... 600/345 |
| 2002/0160520 A1 | 10/2002 | Orloff ............................ 436/72 |
| 2002/0161289 A1 | 10/2002 | Hopkins ....................... 600/322 |
| 2002/0168290 A1 | 11/2002 | Yuzhakov ...................... 422/56 |
| 2002/0169393 A1 | 11/2002 | Cunningham ................ 600/573 |
| 2002/0169394 A1 | 11/2002 | Eppstein ...................... 600/573 |
| 2002/0176984 A1 | 11/2002 | Smart .......................... 428/336 |
| 2002/0177761 A1 | 11/2002 | Orloff .......................... 600/309 |
| 2002/0177763 A1 | 11/2002 | Burns ........................... 600/345 |
| 2002/0188224 A1 | 12/2002 | Roe ............................. 600/584 |
| 2003/0014010 A1 | 1/2003 | Carpenter .................... 604/117 |
| 2003/0018282 A1 | 1/2003 | Effenhauser ................. 600/583 |
| 2003/0018300 A1 | 1/2003 | Duchon .................... 604/164.01 |
| 2003/0028125 A1 | 2/2003 | Yuzhakov |
| 2003/0028126 A1 | 2/2003 | List ............................. 600/583 |
| 2003/0032077 A1 | 2/2003 | Itoh ............................... 435/14 |
| 2003/0038047 A1 | 2/2003 | Sleva ........................... 206/370 |
| 2003/0050537 A1 | 3/2003 | Wessel ......................... 600/300 |
| 2003/0050573 A1 | 3/2003 | Kuhr ............................ 600/567 |
| 2003/0050656 A1 | 3/2003 | Schraga ....................... 606/182 |
| 2003/0057391 A1 | 3/2003 | Krulevitch .................... 251/11 |
| 2003/0060730 A1 | 3/2003 | Perez ........................... 600/576 |
| 2003/0069509 A1 | 4/2003 | Matzinger et al. ........... 600/504 |
| 2003/0069753 A1 | 4/2003 | Brown ............................ 705/2 |
| 2003/0072647 A1 | 4/2003 | Lum ............................. 415/1 |
| 2003/0073089 A1 | 4/2003 | Mauze ........................... 435/6 |
| 2003/0073229 A1 | 4/2003 | Greenstein ................ 435/287.2 |
| 2003/0073931 A1 | 4/2003 | Boecker ....................... 600/573 |
| 2003/0083685 A1 | 5/2003 | Freeman ..................... 606/181 |
| 2003/0083686 A1 | 5/2003 | Freeman ..................... 606/181 |
| 2003/0088160 A1 | 5/2003 | Halleck ....................... 600/300 |
| 2003/0088191 A1 | 5/2003 | Freeman et al. ............. 600/583 |
| 2003/0089730 A1 | 5/2003 | May ............................. 221/232 |
| 2003/0092982 A1 | 5/2003 | Eppstein |
| 2003/0093010 A1 | 5/2003 | Essenpreis ................... 600/583 |
| 2003/0100040 A1 | 5/2003 | Bonnecaze .................... 435/14 |
| 2003/0106810 A1 | 6/2003 | Douglas ..................... 205/777.5 |
| 2003/0109777 A1 | 6/2003 | Kloepfer ...................... 600/367 |
| 2003/0109860 A1 | 6/2003 | Black ............................ 606/10 |
| 2003/0111357 A1 | 6/2003 | Black ........................... 205/775 |
| 2003/0113827 A1 | 6/2003 | Burkoth ........................ 435/14 |
| 2003/0116447 A1 | 6/2003 | Surridge .................... 205/777.5 |
| 2003/0120297 A1 | 6/2003 | Beyerlein ..................... 606/185 |
| 2003/0135333 A1 | 7/2003 | Aceti ............................ 702/31 |
| 2003/0136189 A1 | 7/2003 | Lauman ..................... 73/304 C |
| 2003/0139653 A1 | 7/2003 | Manser ........................ 600/300 |
| 2003/0143113 A2 | 7/2003 | Yuzhakov ...................... 422/56 |
| 2003/0144608 A1 | 7/2003 | Kojima ........................ 600/583 |
| 2003/0144609 A1 | 7/2003 | Kennedy ..................... 600/583 |
| 2003/0146110 A1 | 8/2003 | Karinka .................... 205/777.5 |
| 2003/0149348 A1 | 8/2003 | Raskas ........................ 600/310 |
| 2003/0149377 A1 | 8/2003 | Erickson ..................... 600/573 |
| 2003/0150745 A1 | 8/2003 | Teodorczyk et al. .......... 205/775 |
| 2003/0153900 A1 | 8/2003 | Aceti ........................ 604/890.1 |
| 2003/0159944 A1 | 8/2003 | Pottgen .................... 205/777.5 |
| 2003/0163351 A1 | 8/2003 | Brown ............................ 705/2 |
| 2003/0178322 A1 | 9/2003 | Iyengar ....................... 205/775 |
| 2003/0191376 A1 | 10/2003 | Samuels ...................... 600/309 |
| 2003/0191415 A1 | 10/2003 | Moerman ..................... 600/584 |
| 2003/0195435 A1 | 10/2003 | Williams ..................... 600/583 |
| 2003/0195540 A1 | 10/2003 | Moerman ..................... 606/181 |
| 2003/0199744 A1 | 10/2003 | Buse ............................ 600/347 |
| 2003/0199789 A1 | 10/2003 | Boecker ....................... 600/575 |
| 2003/0199790 A1 | 10/2003 | Boecker ....................... 600/576 |
| 2003/0199791 A1 | 10/2003 | Boecker ....................... 600/576 |
| 2003/0199891 A1 | 10/2003 | Argauer ....................... 606/181 |
| 2003/0199893 A1 | 10/2003 | Boecker ....................... 606/181 |
| 2003/0199894 A1 | 10/2003 | Boecker ....................... 606/181 |
| 2003/0199895 A1 | 10/2003 | Boecker ....................... 606/181 |
| 2003/0199896 A1 | 10/2003 | Boecker ....................... 606/181 |
| 2003/0199897 A1 | 10/2003 | Boecker ....................... 606/181 |
| 2003/0199898 A1 | 10/2003 | Boecker ....................... 606/181 |
| 2003/0199899 A1 | 10/2003 | Boecker ....................... 606/181 |
| 2003/0199900 A1 | 10/2003 | Boecker ....................... 606/181 |
| 2003/0199901 A1 | 10/2003 | Boecker ....................... 606/181 |
| 2003/0199902 A1 | 10/2003 | Boecker ....................... 606/181 |
| 2003/0199903 A1 | 10/2003 | Boecker ....................... 606/181 |
| 2003/0199904 A1 | 10/2003 | Boecker ....................... 606/181 |
| 2003/0199905 A1 | 10/2003 | Boecker ....................... 606/181 |
| 2003/0199906 A1 | 10/2003 | Boecker ....................... 606/181 |
| 2003/0199907 A1 | 10/2003 | Boecker ....................... 606/181 |
| 2003/0199908 A1 | 10/2003 | Boecker ....................... 606/181 |
| 2003/0199909 A1 | 10/2003 | Boecker ....................... 606/181 |
| 2003/0199910 A1 | 10/2003 | Boecker ....................... 606/181 |
| 2003/0199911 A1 | 10/2003 | Boecker ....................... 606/181 |
| 2003/0199912 A1 | 10/2003 | Pugh ........................... 606/182 |
| 2003/0201194 A1 | 10/2003 | Heller ....................... 205/777.5 |
| 2003/0203352 A1 | 10/2003 | Haviland ........................ 435/4 |
| 2003/0206828 A1 | 11/2003 | Bell ............................. 422/44 |
| 2003/0208140 A1 | 11/2003 | Pugh ........................... 600/584 |
| 2003/0210811 A1 | 11/2003 | Dubowsky ................... 382/128 |
| 2003/0211619 A1* | 11/2003 | Olson ..................... A61B 5/1411 436/44 |
| 2003/0212344 A1 | 11/2003 | Yuzhakov ..................... 600/583 |

(56) References Cited

U.S. PATENT DOCUMENTS

| | | | |
|---|---|---|---|
| 2003/0212345 A1 | 11/2003 | McAllister | 600/584 |
| 2003/0212346 A1 | 11/2003 | McAllister | 600/584 |
| 2003/0212347 A1 | 11/2003 | Sohrab | 600/584 |
| 2003/0212379 A1 | 11/2003 | Bylund | 604/504 |
| 2003/0212423 A1 | 11/2003 | Pugh | 606/181 |
| 2003/0212424 A1 | 11/2003 | Briggs | 606/181 |
| 2003/0212579 A1 | 11/2003 | Brown | 705/2 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe | 606/182 |
| 2003/0225430 A1 | 12/2003 | Schraga | 606/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0019259 A1 | 1/2004 | Brown | 600/300 |
| 2004/0026243 A1 | 2/2004 | Davies | 204/403.14 |
| 2004/0026244 A1 | 2/2004 | Hodges | 204/409 |
| 2004/0030353 A1 | 2/2004 | Schmelzeisen-R | 606/181 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1* | 2/2004 | Wurster | A61B 5/1411 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0049219 A1 | 3/2004 | Briggs | 606/181 |
| 2004/0049220 A1 | 3/2004 | Boecker | 606/181 |
| 2004/0050694 A1 | 3/2004 | Yang | 204/403.02 |
| 2004/0054267 A1 | 3/2004 | Feldman | 600/316 |
| 2004/0054898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0065669 A1 | 4/2004 | Giraud et al. | |
| 2004/0068093 A1 | 4/2004 | Merrigan et al. | |
| 2004/0068283 A1 | 4/2004 | Fukuzawa et al. | 606/181 |
| 2004/0069657 A1 | 4/2004 | Hodges | 205/787 |
| 2004/0087990 A1 | 5/2004 | Boecker | 606/181 |
| 2004/0092842 A1 | 5/2004 | Boecker | 600/575 |
| 2004/0092994 A1 | 5/2004 | Briggs | 606/181 |
| 2004/0092995 A1 | 5/2004 | Boecker | 606/181 |
| 2004/0096991 A1 | 5/2004 | Zhang | 436/518 |
| 2004/0098009 A1 | 5/2004 | Boecker | 606/181 |
| 2004/0098010 A1 | 5/2004 | Davison | 606/181 |
| 2004/0102803 A1 | 5/2004 | Boecker | 606/183 |
| 2004/0106855 A1 | 6/2004 | Brown | 600/301 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0107116 A1 | 6/2004 | Brown | 705/2 |
| 2004/0115754 A1 | 6/2004 | Chang | 435/14 |
| 2004/0115831 A1 | 6/2004 | Meathrel | 436/514 |
| 2004/0116780 A1 | 6/2004 | Brown | 600/300 |
| 2004/0116829 A1 | 6/2004 | Raney | 600/573 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0137640 A1 | 7/2004 | Hirao | 436/514 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Kheiri | 606/182 |
| 2004/0167383 A1 | 8/2004 | Kim | 600/365 |
| 2004/0171057 A1 | 9/2004 | Yang | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koike | 606/181 |
| 2004/0193201 A1 | 9/2004 | Kim | 606/181 |
| 2004/0193377 A1 | 9/2004 | Brown | 702/19 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0199409 A1 | 10/2004 | Brown | 705/3 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219500 A1 | 11/2004 | Brown | 434/307 R |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220564 A1 | 11/2004 | Ho | 606/47 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |

(56) References Cited

U.S. PATENT DOCUMENTS

| | | | |
|---|---|---|---|
| 2004/0230216 A1* | 11/2004 | Levaughn | A61B 5/1411 606/181 |
| 2004/0231983 A1 | 11/2004 | Shen | 204/403.01 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Shraga | 606/182 |
| 2004/0238357 A1 | 12/2004 | Bhullar | 204/400 |
| 2004/0238358 A1 | 12/2004 | Forrow | 204/403 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249254 A1 | 12/2004 | Racchini | 600/347 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267121 A1 | 12/2004 | Sarvazyan et al. | |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1* | 1/2005 | Kuhr | A61B 5/1411 606/181 |
| 2005/0027181 A1 | 2/2005 | Goode, Jr. | 600/365 |
| 2005/0027211 A1 | 2/2005 | Kuhr | 600/583 |
| 2005/0027562 A1 | 2/2005 | Brown | 705/2 |
| 2005/0033340 A1 | 2/2005 | Lipoma | 606/181 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Katsuji | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Shraga | 606/182 |
| 2005/0038465 A1 | 2/2005 | Shraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049472 A1 | 3/2005 | Manda | 600/345 |
| 2005/0049473 A1 | 3/2005 | Desai | 600/347 |
| 2005/0050859 A1 | 3/2005 | Coppeta | 5/471 |
| 2005/0054082 A1 | 3/2005 | Pachl | 435/287.2 |
| 2005/0054908 A1 | 3/2005 | Blank | 600/316 |
| 2005/0059872 A1 | 3/2005 | Shartle | 600/347 |
| 2005/0059895 A1 | 3/2005 | Brown | 600/481 |
| 2005/0060194 A1 | 3/2005 | Brown | 705/2 |
| 2005/0061668 A1 | 3/2005 | Brenneman | 204/403.01 |
| 2005/0064528 A1 | 3/2005 | Kwon | 435/14 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/64 |
| 2005/0096686 A1 | 5/2005 | Allen | 606/181 |
| 2005/0098431 A1 | 5/2005 | Hodges | 204/403.2 |
| 2005/0098432 A1 | 5/2005 | Gundel | 204/403.2 |
| 2005/0098433 A1 | 5/2005 | Gundel | 204/403.2 |
| 2005/0098434 A1 | 5/2005 | Gundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112712 A1 | 5/2005 | Ouyang | 435/14 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowicz | 705/1 |
| 2005/0114444 A1 | 5/2005 | Brown | 709/203 |
| 2005/0118056 A1 | 6/2005 | Swanson | 423/23 |
| 2005/0118062 A1 | 6/2005 | Otake | 422/68.1 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131440 A1 | 6/2005 | Starnes | |

(56) References Cited

U.S. PATENT DOCUMENTS

| | | | |
|---|---|---|---|
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Gonnelli | 604/173 |
| 2005/0137536 A1 | 6/2005 | Gonnelli | 604/264 |
| 2005/0140659 A1 | 6/2005 | Hohl | 345/169 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1* | 7/2005 | Trissel et al. | 606/181 |
| 2005/0149090 A1 | 7/2005 | Susumu | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/181 |
| 2005/0163176 A1 | 7/2005 | You et al. | 372/36 |
| 2005/0164299 A1 | 7/2005 | Stewart | 435/7.1 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169810 A1 | 8/2005 | Hagen | 422/102 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0176153 A1 | 8/2005 | O'hara | 436/70 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Saito | 435/287.1 |
| 2005/0182307 A1 | 8/2005 | Currie | 600/300 |
| 2005/0187439 A1 | 8/2005 | Blank | 600/310 |
| 2005/0187442 A1 | 8/2005 | Cho et al. | |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205136 A1 | 9/2005 | Freeman | 137/554 |
| 2005/0205422 A1 | 9/2005 | Moser | 204/403.06 |
| 2005/0205816 A1 | 9/2005 | Hayenga | 251/61.1 |
| 2005/0209315 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245846 A1 | 11/2005 | Day | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030050 A1 | 2/2006 | Milne | 436/67 |
| 2006/0030761 A1 | 2/2006 | Raskas | 600/316 |
| 2006/0030788 A1 | 2/2006 | Wong | 600/583 |
| 2006/0034728 A1 | 2/2006 | Kloepfer | 422/68.1 |
| 2006/0037859 A1 | 2/2006 | Hodges | 204/400 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |

(56) References Cited

U.S. PATENT DOCUMENTS

| | | | |
|---|---|---|---|
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094985 A1 | 5/2006 | Aceti | 600/575 |
| 2006/0094986 A1 | 5/2006 | Neel | 600/583 |
| 2006/0095061 A1 | 5/2006 | Trautman | 606/185 |
| 2006/0096859 A1 | 5/2006 | King Tong Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olson | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0160100 A1 | 7/2006 | Gao | 435/6 |
| 2006/0161078 A1 | 7/2006 | Schraga | 600/583 |
| 2006/0161194 A1 | 7/2006 | Freeman | 606/185 |
| 2006/0163061 A1 | 7/2006 | Hodges | 204/401 |
| 2006/0166302 A1 | 7/2006 | Clarke | 435/25 |
| 2006/0167382 A1 | 7/2006 | Deshmukh | 600/583 |
| 2006/1051342 | 7/2006 | Yaguchi | 206/306 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184065 A1 | 8/2006 | Deshmukh | 600/583 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0201804 A1 | 9/2006 | Chambers | 204/400 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222566 A1 | 10/2006 | Brauker et al. | 422/68.1 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | Levaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0229652 A1 | 10/2006 | Lio et al. | 606/182 |
| 2006/0231396 A1 | 10/2006 | Yamaoka | 204/403.14 |
| 2006/0231418 A1 | 10/2006 | Harding | 205/775 |
| 2006/0231421 A1 | 10/2006 | Diamond | 205/777.5 |
| 2006/0231423 A1 | 10/2006 | Harding | 205/792 |
| 2006/0231425 A1 | 10/2006 | Harding | 205/792 |
| 2006/0231442 A1 | 10/2006 | Windus-Smith | 206/438 |
| 2006/0232278 A1 | 10/2006 | Diamond | 324/444 |
| 2006/0232528 A1 | 10/2006 | Harding | 345/87 |
| 2006/0233666 A1 | 10/2006 | Vu | 422/68.1 |
| 2006/0234263 A1 | 10/2006 | Light, II | C12Q 1/68 |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0247154 A1 | 11/2006 | Palmieri | 514/8 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | Levaughn | 606/182 |
| 2006/0254932 A1 | 11/2006 | Hodges | 205/775 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna | 606/181 |
| 2006/0266644 A1 | 11/2006 | Pugh | 204/400 |
| 2006/0266765 A1 | 11/2006 | Pugh | 222/1 |
| 2006/0271083 A1 | 11/2006 | Boecker | 606/181 |
| 2006/0271084 A1 | 11/2006 | Schraga | 606/182 |

(56) References Cited

U.S. PATENT DOCUMENTS

| | | | |
|---|---|---|---|
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0279431 A1 | 12/2006 | Bakarania | 340/870.02 |
| 2006/0281187 A1 | 12/2006 | Emery | 436/169 |
| 2006/0282109 A1 | 12/2006 | Jansen | 606/181 |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |
| 2007/0004990 A1 | 1/2007 | Kistner | 600/583 |
| 2007/0007183 A1 | 1/2007 | Schulat | 209/573 |
| 2007/0009381 A1 | 1/2007 | Schulat | 422/58 |
| 2007/0010839 A1 | 1/2007 | Galloway | 606/167 |
| 2007/0010841 A1 | 1/2007 | Teo | 606/181 |
| 2007/0015978 A1 | 1/2007 | Kanayama | 600/310 |
| 2007/0016079 A1 | 1/2007 | Freeman | 600/476 |
| 2007/0016103 A1 | 1/2007 | Calasso | 600/583 |
| 2007/0016104 A1 | 1/2007 | Jansen | 600/583 |
| 2007/0016239 A1 | 1/2007 | Sato | 606/181 |
| 2007/0017805 A1 | 1/2007 | Hodges | 204/400 |
| 2007/0027370 A1 | 2/2007 | Brauker | 600/309 |
| 2007/0027427 A1 | 2/2007 | Trautman | 604/46 |
| 2007/0032812 A1 | 2/2007 | Loerwald | 606/181 |
| 2007/0032813 A1 | 2/2007 | Flynn | 606/181 |
| 2007/0038149 A1 | 2/2007 | Calasso | 600/583 |
| 2007/0038235 A1 | 2/2007 | Freeman | 606/181 |
| 2007/0043305 A1 | 2/2007 | Boecker | 600/583 |
| 2007/0043386 A1 | 2/2007 | Freeman | 606/181 |
| 2007/0049901 A1 | 3/2007 | Wu | 604/506 |
| 2007/0049959 A1 | 3/2007 | Feaster | 606/181 |
| 2007/0055174 A1 | 3/2007 | Freeman | 600/583 |
| 2007/0055297 A1 | 3/2007 | Fukuzawa | 606/181 |
| 2007/0055298 A1 | 3/2007 | Uehata | 606/181 |
| 2007/0060842 A1 | 3/2007 | Alvarez-Icaza | 600/583 |
| 2007/0060843 A1 | 3/2007 | Alvarez-Icaza | 600/583 |
| 2007/0060844 A1 | 3/2007 | Alvarez-Icaza | 600/583 |
| 2007/0060845 A1 | 3/2007 | Perez | 600/583 |
| 2007/0061393 A1 | 3/2007 | Chen | 205/777.5 |
| 2007/0062250 A1 | 3/2007 | Krulevitch | 73/1.16 |
| 2007/0062251 A1 | 3/2007 | Anex | 73/1.36 |
| 2007/0062315 A1 | 3/2007 | Hodges | 73/864.72 |
| 2007/0064516 A1 | 3/2007 | Briggs | 365/230.05 |
| 2007/0066939 A1 | 3/2007 | Krulevitch | 604/152 |
| 2007/0066940 A1 | 3/2007 | Karunaratne | 604/152 |
| 2007/0068807 A1 | 3/2007 | Feldman | 204/403.01 |
| 2007/0073188 A1 | 3/2007 | Freeman | 600/583 |
| 2007/0073189 A1 | 3/2007 | Freeman | 600/583 |
| 2007/0074977 A1 | 4/2007 | Guo | 205/792 |
| 2007/0078358 A1 | 4/2007 | Escutia | 600/573 |
| 2007/0078360 A1 | 4/2007 | Matsumoto | 600/583 |
| 2007/0078474 A1 | 4/2007 | Kim | 606/181 |
| 2007/0080093 A1 | 4/2007 | Boozer | 206/569 |
| 2007/0083130 A1 | 4/2007 | Thomson | 600/583 |
| 2007/0083131 A1 | 4/2007 | Escutia | 600/583 |
| 2007/0083222 A1 | 4/2007 | Schraga | 606/181 |
| 2007/0083335 A1 | 4/2007 | Moerman | 702/19 |
| 2007/0084749 A1 | 4/2007 | Demelo | 206/569 |
| 2007/0088377 A1 | 4/2007 | LeVaughn | 606/181 |
| 2007/0092923 A1 | 4/2007 | Chang | 435/14 |
| 2007/0093728 A1 | 4/2007 | Douglas | 600/583 |
| 2007/0093752 A1 | 4/2007 | Zhao | 604/131 |
| 2007/0093753 A1 | 4/2007 | Krulevitch | 604/131 |
| 2007/0093863 A1 | 4/2007 | Pugh | 606/181 |
| 2007/0093864 A1 | 4/2007 | Pugh | 606/181 |
| 2007/0095178 A1 | 5/2007 | Schraga | 83/13 |
| 2007/0100255 A1 | 5/2007 | Boecker | 600/583 |
| 2007/0100256 A1 | 5/2007 | Sansom | 600/583 |
| 2007/0100364 A1 | 5/2007 | Sansom | 606/181 |
| 2007/0102312 A1 | 5/2007 | Cha | 206/363 |
| 2007/0106178 A1 | 5/2007 | Roe | 600/583 |
| 2007/0108048 A1 | 5/2007 | Wang | 204/403.01 |
| 2007/0112281 A1 | 5/2007 | Olson | 600/583 |
| 2007/0112367 A1 | 5/2007 | Olson | 606/181 |
| 2007/0118051 A1 | 5/2007 | Korner et al. | 600/583 |
| 2007/0119710 A1 | 5/2007 | Goldberger | 204/403.01 |
| 2007/0123801 A1 | 5/2007 | Goldberger | 600/583 |
| 2007/0123802 A1 | 5/2007 | Freeman | 600/583 |
| 2007/0123803 A1 | 5/2007 | Fujiwara et al. | 600/583 |
| 2007/0129618 A1 | 6/2007 | Goldberger | 600/345 |
| 2007/0129650 A1 | 6/2007 | Freeman | 600/583 |
| 2007/0131565 A1 | 6/2007 | Fujiwara | 205/777.5 |
| 2007/0135828 A1 | 6/2007 | Rutynowski | 606/181 |
| 2007/0142747 A1 | 6/2007 | Boecker | 600/583 |
| 2007/0142748 A1 | 6/2007 | Freeman | 600/583 |
| 2007/0142776 A9 | 6/2007 | Kovelman | 604/136 |
| 2007/0142854 A1 | 6/2007 | Schraga | 606/181 |
| 2007/0144235 A1 | 6/2007 | Werner | 73/1.82 |
| 2007/0149875 A1 | 6/2007 | Ouyang | 600/347 |
| 2007/0149897 A1 | 6/2007 | Ghesquiere | 600/583 |
| 2007/0161960 A1 | 7/2007 | Chen | 604/187 |
| 2007/0162064 A1 | 7/2007 | Starnes | 606/181 |
| 2007/0162065 A1 | 7/2007 | Li | 606/182 |
| 2007/0167869 A1 | 7/2007 | Roe | 600/583 |
| 2007/0167870 A1 | 7/2007 | Freeman | 600/583 |
| 2007/0167871 A1 | 7/2007 | Freeman | 600/583 |
| 2007/0167872 A1 | 7/2007 | Freeman | 600/583 |
| 2007/0167873 A1 | 7/2007 | Freeman | 600/583 |
| 2007/0167874 A1 | 7/2007 | Freeman | 600/583 |
| 2007/0167875 A1 | 7/2007 | Freeman | 600/583 |
| 2007/0173739 A1 | 7/2007 | Chan | 600/583 |
| 2007/0173740 A1 | 7/2007 | Chan | 600/583 |
| 2007/0173741 A1 | 7/2007 | Deshmukh | 600/583 |
| 2007/0173742 A1 | 7/2007 | Freeman | 600/583 |
| 2007/0173743 A1 | 7/2007 | Freeman | 600/583 |
| 2007/0173874 A1 | 7/2007 | Uschold | 606/181 |
| 2007/0173875 A1 | 7/2007 | Uschold | 606/181 |
| 2007/0173876 A1 | 7/2007 | Aylett | 606/181 |
| 2007/0176120 A1 | 8/2007 | Schwind | 250/492.1 |
| 2007/0179356 A1 | 8/2007 | Wessel | 600/300 |
| 2007/0179404 A1 | 8/2007 | Escutia | 600/583 |
| 2007/0179405 A1 | 8/2007 | Emery | 600/583 |
| 2007/0179406 A1 | 8/2007 | DeNuzzio | 600/583 |
| 2007/0182051 A1 | 8/2007 | Harttig | 264/138 |
| 2007/0185412 A1 | 8/2007 | Boecker | 600/583 |
| 2007/0185515 A1 | 8/2007 | Stout | 606/181 |
| 2007/0185516 A1 | 8/2007 | Schosnig | 606/181 |
| 2007/0191702 A1 | 8/2007 | Yodfat | 600/365 |
| 2007/0191737 A1 | 8/2007 | Freeman | 600/583 |
| 2007/0191738 A1 | 8/2007 | Raney | 600/583 |
| 2007/0191739 A1 | 8/2007 | Roe | 600/583 |
| 2007/0193019 A1 | 8/2007 | Feldman | 29/592.1 |
| 2007/0193882 A1 | 8/2007 | Dai | 204/403.02 |
| 2007/0196240 A1 | 8/2007 | Boozer | 422/102 |
| 2007/0196242 A1 | 8/2007 | Boozer | 422/102 |
| 2007/0203514 A1 | 8/2007 | Flaherty | 606/181 |
| 2007/0203903 A1 | 8/2007 | Attaran Rezaei | 707/5 |
| 2007/0205103 A1 | 9/2007 | Hodges | 204/403.01 |
| 2007/0207498 A1 | 9/2007 | Palmieri | 435/7.1 |
| 2007/0213601 A1 | 9/2007 | Freeman | 600/300 |
| 2007/0213637 A1 | 9/2007 | Boozer | 600/583 |
| 2007/0213682 A1 | 9/2007 | Haar | 604/500 |
| 2007/0213756 A1 | 9/2007 | Freeman | 606/181 |
| 2007/0218543 A1 | 9/2007 | Flaherty | 435/287.1 |
| 2007/0219346 A1 | 9/2007 | Trifiro | 530/308 |
| 2007/0219432 A1 | 9/2007 | Thompson | 600/300 |
| 2007/0219436 A1 | 9/2007 | Takase | 600/310 |
| 2007/0219462 A1 | 9/2007 | Briggs | 600/583 |
| 2007/0219463 A1 | 9/2007 | Briggs | 600/583 |
| 2007/0219572 A1 | 9/2007 | Deck | 606/181 |
| 2007/0219573 A1 | 9/2007 | Freeman | 606/183 |
| 2007/0219574 A1 | 9/2007 | Freeman | 606/185 |
| 2007/0225741 A1 | 9/2007 | Ikeda | 606/182 |
| 2007/0225742 A1 | 9/2007 | Abe | 606/182 |
| 2007/0227907 A1 | 10/2007 | Shah | 205/777.5 |
| 2007/0227911 A1 | 10/2007 | Wang | 205/792 |
| 2007/0227912 A1 | 10/2007 | Chatelier | 205/792 |
| 2007/0229085 A1 | 10/2007 | Kawai | 324/450 |
| 2007/0232872 A1 | 10/2007 | Prough | 600/316 |
| 2007/0232956 A1 | 10/2007 | Harman | 600/573 |
| 2007/0233013 A1 | 10/2007 | Schoenberg | 604/192 |
| 2007/0233166 A1 | 10/2007 | Stout | 606/182 |
| 2007/0233167 A1 | 10/2007 | Weiss | 606/182 |
| 2007/0233395 A1 | 10/2007 | Neel | 702/19 |

(56) References Cited

U.S. PATENT DOCUMENTS

| | | | |
|---|---|---|---|
| 2007/0235329 A1 | 10/2007 | Harding | 204/403.01 |
| 2007/0235347 A1 | 10/2007 | Chatelier | 205/792 |
| 2007/0239068 A1 | 10/2007 | Rasch-Menges | 600/573 |
| 2007/0239188 A1 | 10/2007 | Boozer | 606/181 |
| 2007/0239189 A1 | 10/2007 | Freeman | 606/181 |
| 2007/0239190 A1 | 10/2007 | Alden | 606/181 |
| 2007/0240984 A1 | 10/2007 | Popovich | 204/403.01 |
| 2007/0240986 A1 | 10/2007 | Reymond | 204/412 |
| 2007/0244380 A1 | 10/2007 | Say | 600/347 |
| 2007/0244412 A1 | 10/2007 | Lav | 600/584 |
| 2007/0244498 A1 | 10/2007 | Steg | 606/181 |
| 2007/0244499 A1 | 10/2007 | Briggs | 606/182 |
| 2007/0249921 A1 | 10/2007 | Groll | 600/347 |
| 2007/0249962 A1 | 10/2007 | Alden | 600/583 |
| 2007/0249963 A1 | 10/2007 | Alden | 600/583 |
| 2007/0250099 A1 | 10/2007 | Flora | 606/181 |
| 2007/0251836 A1 | 11/2007 | Hsu | 205/792 |
| 2007/0254359 A1 | 11/2007 | Rezania | 435/325 |
| 2007/0255141 A1 | 11/2007 | Esenaliev | 600/475 |
| 2007/0255178 A1 | 11/2007 | Alvarez-Icaza | 600/583 |
| 2007/0255179 A1 | 11/2007 | Alvarez-Icaza | 600/583 |
| 2007/0255180 A1 | 11/2007 | Alvarez-Icaza | 600/583 |
| 2007/0255181 A1 | 11/2007 | Alvarez-Icaza | 600/583 |
| 2007/0255300 A1 | 11/2007 | Vanhiel | 606/181 |
| 2007/0255301 A1 | 11/2007 | Freeman | 606/181 |
| 2007/0255302 A1 | 11/2007 | Koeppel | 606/182 |
| 2007/0260271 A1 | 11/2007 | Freeman | 606/181 |
| 2007/0260272 A1 | 11/2007 | Weiss | 606/181 |
| 2007/0264721 A1 | 11/2007 | Buck | 436/150 |
| 2007/0265511 A1 | 11/2007 | Renouf | 600/319 |
| 2007/0265532 A1 | 11/2007 | Maynard | 600/477 |
| 2007/0265654 A1 | 11/2007 | Iio | 606/185 |
| 2007/0273901 A1 | 11/2007 | Baskeyfield | 358/1.9 |
| 2007/0273903 A1 | 11/2007 | Baskeyfield | 358/1.9 |
| 2007/0273904 A1 | 11/2007 | Robinson | 358/1.9 |
| 2007/0273928 A1 | 11/2007 | Robinson | 358/1.9 |
| 2007/0276197 A1 | 11/2007 | Harmon | 600/300 |
| 2007/0276211 A1 | 11/2007 | Mir | 600/345 |
| 2007/0276290 A1 | 11/2007 | Boecker | 600/583 |
| 2007/0276425 A1 | 11/2007 | Kim | 606/186 |
| 2007/0276621 A1 | 11/2007 | Davies | 702/104 |
| 2007/0278097 A1 | 12/2007 | Bhullar | 204/403.01 |
| 2007/0282186 A1 | 12/2007 | Gilmore | 600/365 |
| 2007/0282362 A1 | 12/2007 | Berg | 606/181 |
| 2007/0288047 A1 | 12/2007 | Thoes | 606/182 |
| 2007/0293743 A1 | 12/2007 | Monfre | 600/316 |
| 2007/0293744 A1 | 12/2007 | Monfre | 600/316 |
| 2007/0293790 A1 | 12/2007 | Bainczyk | 600/583 |
| 2007/0293882 A1 | 12/2007 | Harttig | 606/181 |
| 2007/0293883 A1 | 12/2007 | Horie | 606/181 |
| 2007/0295616 A1 | 12/2007 | Harding | 205/777.5 |
| 2008/0004651 A1 | 1/2008 | Nicholls | 606/182 |
| 2008/0007141 A1 | 1/2008 | Deck | 310/328 |
| 2008/0009767 A1 | 1/2008 | Effenhauser | 600/583 |
| 2008/0009768 A1 | 1/2008 | Sohrab | 600/583 |
| 2008/0009892 A1 | 1/2008 | Freeman | 606/181 |
| 2008/0009893 A1 | 1/2008 | LeVaughn | 606/181 |
| 2008/0015425 A1 | 1/2008 | Douglas | 600/347 |
| 2008/0015623 A1 | 1/2008 | Deck | 606/181 |
| 2008/0017522 A1 | 1/2008 | Heller | 205/777.5 |
| 2008/0019870 A1 | 1/2008 | Newman | 422/68.1 |
| 2008/0021291 A1 | 1/2008 | Zocchi | 600/300 |
| 2008/0021293 A1 | 1/2008 | Schurman | 600/316 |
| 2008/0021295 A1 | 1/2008 | Wang | 600/347 |
| 2008/0021296 A1 | 1/2008 | Creaven | 600/365 |
| 2008/0021346 A1 | 1/2008 | Haar | 600/583 |
| 2008/0021490 A1 | 1/2008 | Briggs | 606/181 |
| 2008/0021491 A1 | 1/2008 | Freeman | 606/181 |
| 2008/0021492 A1 | 1/2008 | Freeman | 606/181 |
| 2008/0021493 A1 | 1/2008 | Levaughn | 606/181 |
| 2008/0021494 A1 | 1/2008 | Schmelzeisen-R | 606/181 |
| 2008/0027385 A1 | 1/2008 | Freeman | 604/117 |
| 2008/0031778 A1 | 2/2008 | Kramer | 422/68.1 |
| 2008/0033268 A1 | 2/2008 | Stafford | 600/345 |
| 2008/0033318 A1 | 2/2008 | Mace | 600/583 |
| 2008/0033319 A1 | 2/2008 | Kloepfer | 600/583 |
| 2008/0033468 A1 | 2/2008 | Lathrop | 606/181 |
| 2008/0033469 A1 | 2/2008 | Winheim | 606/181 |
| 2008/0034834 A1 | 2/2008 | Schell | 73/1.02 |
| 2008/0034835 A1 | 2/2008 | Schell | 73/1.02 |
| 2008/0039885 A1 | 2/2008 | Purcell | 606/182 |
| 2008/0039886 A1 | 2/2008 | Shi | 606/182 |
| 2008/0039887 A1 | 2/2008 | Conway | 606/182 |
| 2008/0040919 A1 | 2/2008 | Griss | 29/777 |
| 2008/0045825 A1 | 2/2008 | Melker | 600/365 |
| 2008/0045992 A1 | 2/2008 | Schraga | 606/182 |
| 2008/0047764 A1 | 2/2008 | Lee | G08C 21/00 |
| 2008/0053201 A1 | 3/2008 | Roesicke | 73/61.41 |
| 2008/0057484 A1 | 3/2008 | Miyata | 434/739 |
| 2008/0058624 A1 | 3/2008 | Smart | 600/345 |
| 2008/0058626 A1 | 3/2008 | Miyata | 600/365 |
| 2008/0058631 A1 | 3/2008 | Draudt | 600/385 |
| 2008/0058847 A1 | 3/2008 | Abe | 606/181 |
| 2008/0058848 A1 | 3/2008 | Griffin | 606/182 |
| 2008/0058849 A1 | 3/2008 | Conway | 606/183 |
| 2008/0060424 A1 | 3/2008 | Babic | 73/61.41 |
| 2008/0064986 A1 | 3/2008 | Kraemer | 600/583 |
| 2008/0064987 A1 | 3/2008 | Escutia | 600/583 |
| 2008/0065130 A1 | 3/2008 | Patel | 606/181 |
| 2008/0065131 A1 | 3/2008 | List | 606/181 |
| 2008/0065132 A1 | 3/2008 | Trissel | 606/182 |
| 2008/0065133 A1 | 3/2008 | Kennedy | 606/182 |
| 2008/0065134 A1 | 3/2008 | Conway | 606/182 |
| 2008/0073224 A1 | 3/2008 | Diamond | 205/775 |
| 2008/0077048 A1 | 3/2008 | Escutia | 600/583 |
| 2008/0077167 A1 | 3/2008 | Flynn | 606/172 |
| 2008/0077168 A1 | 3/2008 | Nicholls | 606/182 |
| 2008/0081969 A1 | 4/2008 | Feldman | 600/322 |
| 2008/0081976 A1 | 4/2008 | Hodges | 600/345 |
| 2008/0082023 A1 | 4/2008 | Deck | 600/583 |
| 2008/0082116 A1 | 4/2008 | Lathrop | 606/181 |
| 2008/0082117 A1 | 4/2008 | Ruf | 606/182 |
| 2008/0086042 A1 | 4/2008 | Brister | 600/347 |
| 2008/0086044 A1 | 4/2008 | Brister | 600/365 |
| 2008/0086273 A1 | 4/2008 | Shults | 702/19 |
| 2008/0093227 A1 | 4/2008 | Diamond | 205/775 |
| 2008/0093228 A1 | 4/2008 | Diamond | 205/782 |
| 2008/0093230 A1 | 4/2008 | Diamond | 205/792 |
| 2008/0094804 A1 | 4/2008 | Reynolds | 361/727 |
| 2008/0097171 A1 | 4/2008 | Smart | 600/309 |
| 2008/0097241 A1 | 4/2008 | Maltezos | 600/576 |
| 2008/0097503 A1 | 4/2008 | Creaven | 606/182 |
| 2008/0098802 A1 | 5/2008 | Burke | 73/61.61 |
| 2008/0103396 A1 | 5/2008 | Johnson | 600/477 |
| 2008/0103415 A1 | 5/2008 | Roe | 600/583 |
| 2008/0103517 A1 | 5/2008 | Takemoto | 606/182 |
| 2008/0105024 A1 | 5/2008 | Creaven | 73/1.02 |
| 2008/0105568 A1 | 5/2008 | Wu | 205/780.5 |
| 2008/0108130 A1 | 5/2008 | Nakaminami | 435/287.1 |
| 2008/0108942 A1 | 5/2008 | Brister | 604/118 |
| 2008/0109024 A1 | 5/2008 | Berkovitch | 606/181 |
| 2008/0109025 A1 | 5/2008 | Yang | 606/182 |
| 2008/0109259 A1 | 5/2008 | Thompson | 705/3 |
| 2008/0114227 A1 | 5/2008 | Haar | 600/347 |
| 2008/0114228 A1 | 5/2008 | McCluskey | 600/365 |
| 2008/0118400 A1 | 5/2008 | Neel | 422/68.1 |
| 2008/0119703 A1 | 5/2008 | Brister | 600/347 |
| 2008/0119704 A1 | 5/2008 | Brister | 600/347 |
| 2008/0119706 A1 | 5/2008 | Brister | 600/365 |
| 2008/0119761 A1 | 5/2008 | Boecker | 600/583 |
| 2008/0119883 A1 | 5/2008 | Conway | 606/181 |
| 2008/0119884 A1 | 5/2008 | Flora | 606/182 |
| 2008/0121533 A1 | 5/2008 | Hodges | 205/775 |
| 2008/0125800 A1 | 5/2008 | List | 606/181 |
| 2008/0125801 A1 | 5/2008 | List | 606/181 |
| 2008/0134806 A1 | 6/2008 | Capriccio | 73/863.21 |
| 2008/0134810 A1 | 6/2008 | Neel | 73/866 |
| 2008/0135559 A1 | 6/2008 | Byrd | 220/506 |
| 2008/0140105 A1 | 6/2008 | Zhong | 606/182 |
| 2008/0144022 A1 | 6/2008 | Schulat | 356/213 |
| 2008/0146899 A1 | 6/2008 | Ruchti | 600/316 |
| 2008/0146966 A1 | 6/2008 | LeVaughn | 600/583 |
| 2008/0147108 A1 | 6/2008 | Kennedy | 606/182 |
| 2008/0149268 A1 | 6/2008 | Zhao | 156/299 |

(56) References Cited

U.S. PATENT DOCUMENTS

| | | | |
|---|---|---|---|
| 2008/0149599 A1 | 6/2008 | Bohm | 216/94 |
| 2008/0152507 A1 | 6/2008 | Bohm | 417/44.1 |
| 2008/0154187 A1 | 6/2008 | Krulevitch | 604/48 |
| 2008/0154513 A1 | 6/2008 | Kovatchev | 702/19 |
| 2008/0159913 A1 | 7/2008 | Jung | 422/57 |
| 2008/0161664 A1 | 7/2008 | Mastrototaro | 600/347 |
| 2008/0161724 A1 | 7/2008 | Roe | 600/583 |
| 2008/0161725 A1 | 7/2008 | Wong | 600/583 |
| 2008/0166269 A1 | 7/2008 | Jansen | 422/63 |
| 2008/0167578 A1 | 7/2008 | Bryer | 600/583 |
| 2008/0167673 A1 | 7/2008 | Zhong | 606/181 |
| 2008/0188771 A1 | 8/2008 | Boecker | 600/583 |
| 2008/0194987 A1 | 8/2008 | Boecker | 600/583 |
| 2008/0194989 A1 | 8/2008 | Briggs | 600/583 |
| 2008/0200782 A1 | 8/2008 | Planman et al. | |
| 2008/0208026 A1 | 8/2008 | Noujaim | 600/365 |
| 2008/0208079 A1 | 8/2008 | Hein | 600/583 |
| 2008/0210574 A1 | 9/2008 | Boecker | 205/777.5 |
| 2008/0214909 A1 | 9/2008 | Fuerst | 600/309 |
| 2008/0214917 A1 | 9/2008 | Boecker | 600/347 |
| 2008/0214919 A1 | 9/2008 | Harmon | 600/365 |
| 2008/0214956 A1 | 9/2008 | Briggs | 600/575 |
| 2008/0228212 A1 | 9/2008 | List | 606/182 |
| 2008/0249435 A1 | 10/2008 | Haar | 600/583 |
| 2008/0249554 A1 | 10/2008 | Freeman | 606/181 |
| 2008/0255598 A1 | 10/2008 | LeVaughn et al. | 606/183 |
| 2008/0262387 A1 | 10/2008 | List | 600/583 |
| 2008/0262388 A1 | 10/2008 | List | 600/583 |
| 2008/0267822 A1 | 10/2008 | List | 422/68.1 |
| 2008/0269723 A1 | 10/2008 | Mastrototaro | 604/890.1 |
| 2008/0269791 A1 | 10/2008 | Hoenes | 606/181 |
| 2008/0275365 A1 | 11/2008 | Guthrie | 600/584 |
| 2008/0275384 A1 | 11/2008 | Mastrototaro | 604/66 |
| 2008/0277291 A1 | 11/2008 | Heller | 205/777.5 |
| 2008/0277292 A1 | 11/2008 | Heller | 205/777.5 |
| 2008/0277293 A1 | 11/2008 | Heller | 205/777.5 |
| 2008/0277294 A1 | 11/2008 | Heller | 205/777.5 |
| 2008/0286149 A1 | 11/2008 | Roe | 422/58 |
| 2008/0294068 A1 | 11/2008 | Briggs | 600/583 |
| 2008/0300614 A1 | 12/2008 | Freeman | 606/181 |
| 2008/0318193 A1 | 12/2008 | Alvarez-Icaza | 434/262 |
| 2008/0319284 A1 | 12/2008 | Alvarez-Icaza | 600/309 |
| 2008/0319291 A1 | 12/2008 | Freeman | 600/347 |
| 2009/0005664 A1 | 1/2009 | Freeman | 600/347 |
| 2009/0020438 A1 | 1/2009 | Hodges | 205/782 |
| 2009/0024009 A1 | 1/2009 | Freeman | 600/309 |
| 2009/0026075 A1 | 1/2009 | Harding | 204/403.14 |
| 2009/0026091 A1 | 1/2009 | Harding | 205/777.5 |
| 2009/0027040 A1 | 1/2009 | Kermani | 324/123 |
| 2009/0029479 A1 | 1/2009 | Docherty | 436/149 |
| 2009/0030441 A1 | 1/2009 | Hoerauf | 600/583 |
| 2009/0043177 A1 | 2/2009 | Milledge | 600/309 |
| 2009/0043183 A1 | 2/2009 | Kermani | 600/365 |
| 2009/0048536 A1 | 2/2009 | Freeman | 600/583 |
| 2009/0054813 A1 | 2/2009 | Freeman | 600/584 |
| 2009/0057146 A1 | 3/2009 | Teodorezyk | 204/403.01 |
| 2009/0069716 A1 | 3/2009 | Freeman | 600/583 |
| 2009/0076415 A1 | 3/2009 | Moerman | |
| 2009/0084687 A1 | 4/2009 | Chatelier | 205/792 |
| 2009/0099477 A1 | 4/2009 | Hoenes et al. | |
| 2009/0105572 A1 | 4/2009 | Malecha | 600/365 |
| 2009/0105573 A1 | 4/2009 | Malecha | 600/365 |
| 2009/0112123 A1 | 4/2009 | Freeman | 600/583 |
| 2009/0112155 A1 | 4/2009 | Zhao | 604/67 |
| 2009/0112180 A1 | 4/2009 | Krulevitch | 604/506 |
| 2009/0112185 A1 | 4/2009 | Krulevitch | 604/523 |
| 2009/0118752 A1 | 5/2009 | Perez et al. | |
| 2009/0124932 A1 | 5/2009 | Freeman | 606/181 |
| 2009/0131829 A1 | 5/2009 | Freeman | 600/583 |
| 2009/0131830 A1 | 5/2009 | Freeman | 600/583 |
| 2009/0131964 A1 | 5/2009 | Freeman | 606/181 |
| 2009/0131965 A1 | 5/2009 | Freeman | 606/181 |
| 2009/0137930 A1 | 5/2009 | Freeman | 600/583 |
| 2009/0138032 A1 | 5/2009 | Freeman | 606/181 |
| 2009/0139300 A1 | 6/2009 | Pugh | 73/1.36 |
| 2009/0177117 A1 | 7/2009 | Amano et al. | 600/583 |
| 2009/0184004 A1 | 7/2009 | Chatelier | 205/777.5 |
| 2009/0187351 A1 | 7/2009 | Orr | 702/19 |
| 2009/0192410 A1 | 7/2009 | Freeman | 600/583 |
| 2009/0192411 A1 | 7/2009 | Freeman | 600/583 |
| 2009/0196580 A1 | 8/2009 | Freeman | 386/124 |
| 2009/0204025 A1 | 8/2009 | Marsot | 600/573 |
| 2009/0216100 A1 | 8/2009 | Ebner | 600/347 |
| 2009/0237262 A1 | 9/2009 | Smith | 340/634 |
| 2009/0240127 A1 | 9/2009 | Pinaki | 600/365 |
| 2009/0247838 A1 | 10/2009 | Cummings | 600/309 |
| 2009/0247982 A1 | 10/2009 | Krulevitch | 604/500 |
| 2009/0259146 A1 | 10/2009 | Freeman | 600/583 |
| 2009/0270765 A1 | 10/2009 | Ghesquiere et al. | 600/583 |
| 2009/0280551 A1 | 11/2009 | Cardosi | 435/190 |
| 2009/0281457 A1 | 11/2009 | Faulkner | 600/583 |
| 2009/0281458 A1 | 11/2009 | Faulkner | 600/583 |
| 2009/0281459 A1 | 11/2009 | Faulkner | 600/583 |
| 2009/0301899 A1 | 12/2009 | Hodges | 205/777.5 |
| 2009/0302872 A1 | 12/2009 | Haggett | 324/715 |
| 2009/0302873 A1 | 12/2009 | Haggett | 324/724 |
| 2009/0322630 A1 | 12/2009 | Friman | 343/720 |
| 2009/0325307 A1 | 12/2009 | Haggett | 436/150 |
| 2010/0016700 A1 | 1/2010 | Sieh | 600/365 |
| 2010/0018878 A1 | 1/2010 | Davies | 205/782 |
| 2010/0030110 A1 | 2/2010 | Choi | 600/583 |
| 2010/0041084 A1 | 2/2010 | Stephens | 435/14 |
| 2010/0094170 A1 | 4/2010 | Wilson et al. | |
| 2010/0094324 A1 | 4/2010 | Huang et al. | |
| 2010/0113981 A1 | 5/2010 | Oki et al. | 600/587 |
| 2010/0145377 A1 | 6/2010 | Lai et al. | |
| 2010/0198107 A1 | 8/2010 | Groll et al. | 600/583 |
| 2010/0210970 A1 | 8/2010 | Horikawa et al. | |
| 2010/0256525 A1 | 10/2010 | List et al. | 600/583 |
| 2010/0274273 A1 | 10/2010 | Schraga et al. | |
| 2010/0292611 A1 | 11/2010 | Lum et al. | 600/583 |
| 2010/0324452 A1 | 12/2010 | Freeman et al. | 600/583 |
| 2010/0324582 A1 | 12/2010 | Nicholls et al. | |
| 2011/0041449 A1 | 2/2011 | Espinosa | |
| 2011/0077478 A1 | 3/2011 | Freeman et al. | 600/309 |
| 2011/0077553 A1 | 3/2011 | Alroy | 600/573 |
| 2011/0098541 A1 | 4/2011 | Freeman et al. | 600/309 |
| 2011/0178429 A1 | 7/2011 | Jacobs | |
| 2011/0184448 A1 | 7/2011 | Brown et al. | |
| 2012/0149999 A1 | 6/2012 | Freeman et al. | 600/309 |
| 2012/0232425 A1 | 9/2012 | Freeman et al. | 600/583 |
| 2012/0271197 A1 | 10/2012 | Castle et al. | 600/583 |
| 2012/0296233 A9 | 11/2012 | Freeman | 600/583 |
| 2013/0261500 A1 | 10/2013 | Jacobs | |

FOREIGN PATENT DOCUMENTS

| | | | |
|---|---|---|---|
| DE | 3538313 A1 | 4/1986 | B08B 5/02 |
| DE | 4212315 A1 | 10/1993 | A61B 5/14 |
| DE | 4320347 | 12/1994 | C07D 239/82 |
| DE | 4344452 | 6/1995 | C07D 471/04 |
| DE | 4420232 | 12/1995 | A61B 17/34 |
| DE | 29800611 U | 7/1998 | A61B 17/32 |
| DE | 19819407 | 11/1999 | G01N 33/48 |
| DE | 20009475 | 10/2000 | A61B 5/15 |
| DE | 29824204 | 10/2000 | G01N 33/48 |
| DE | 10032042 | 1/2002 | |
| DE | 10057832 | 2/2002 | |
| DE | 10057832 C1 | 2/2002 | |
| DE | 10142232 | 3/2003 | |
| DE | 10208575 C1 | 8/2003 | |
| DE | 10208575 C1 | 8/2003 | |
| DE | 10245721 | 12/2003 | |
| DE | 10361560 A1 | 7/2005 | A61B 5/15 |
| EP | 0112498 A2 | 7/1984 | A47L 1/00 |
| EP | 137975 A2 | 4/1985 | A61B 5/14 |
| EP | 0160768 | 11/1985 | A61B 5/00 |
| EP | 0199484 A2 | 10/1986 | A61B 5/14 |
| EP | 0254246 | 1/1988 | G01N 21/03 |
| EP | 0289 269 | 11/1988 | |
| EP | 0317847 A1 | 5/1989 | A61B 5/14 |
| EP | 0320109 | 6/1989 | |
| EP | 0 364 208 A1 | 4/1990 | |
| EP | 0364208 A1 | 4/1990 | G01N 33/58 |

(56) References Cited

FOREIGN PATENT DOCUMENTS

| | | | |
|---|---|---|---|
| EP | 0170375 | 5/1990 | |
| EP | 0136362 | 12/1990 | ........... G01N 27/327 |
| EP | 0449525 | 10/1991 | ............... A61B 5/14 |
| EP | 0453283 | 10/1991 | |
| EP | 0263948 | 2/1992 | |
| EP | 0449147 A2 | 8/1992 | ............... A61M 5/32 |
| EP | 0530994 | 3/1993 | ........... C07D 239/80 |
| EP | 0374355 | 6/1993 | |
| EP | 0351891 | 9/1993 | |
| EP | 0593096 | 4/1994 | ........... G01N 27/327 |
| EP | 0630609 A2 | 12/1994 | ............... A61B 5/14 |
| EP | 0415388 | 5/1995 | |
| EP | 0654659 | 5/1995 | ............... G01N 3/52 |
| EP | 0505494 | 7/1995 | |
| EP | 0662367 A1 | 7/1995 | ............... B24C 1/00 |
| EP | 0359831 | 8/1995 | |
| EP | 0471986 | 10/1995 | |
| EP | 0368474 | 12/1995 | |
| EP | 0461601 | 12/1995 | |
| EP | 0429076 | 1/1996 | ........... C12M 1/140 |
| EP | 0552223 | 7/1996 | ........... G01N 33/48 |
| EP | 0735363 | 10/1996 | |
| EP | 0505504 | 3/1997 | |
| EP | 0777123 | 6/1997 | ........... G01N 33/487 |
| EP | 0406304 | 8/1997 | |
| EP | 0537761 | 8/1997 | |
| EP | 0795601 | 9/1997 | |
| EP | 0562370 | 11/1997 | ........... G01N 27/327 |
| EP | 0415393 | 12/1997 | |
| EP | 0823239 | 2/1998 | ............... A61N 1/36 |
| EP | 0560336 | 5/1998 | |
| EP | 0878 708 | 11/1998 | ........... G01N 27/327 |
| EP | 0 898 936 A2 | 3/1999 | |
| EP | 0505475 | 3/1999 | |
| EP | 0898936 A2 | 3/1999 | ............... A61B 5/14 |
| EP | 0901018 | 3/1999 | ............ G01N 33/48 |
| EP | 0470649 | 6/1999 | |
| EP | 0 951 939 | 10/1999 | |
| EP | 0 951 939 A2 | 10/1999 | |
| EP | 0951939 A2 | 10/1999 | ............... B01L 11/00 |
| EP | 0847447 | 11/1999 | |
| EP | 0964059 | 12/1999 | |
| EP | 0964060 | 12/1999 | ............... C12Q 1/00 |
| EP | 0969097 | 1/2000 | |
| EP | 0985376 A1 | 3/2000 | ............... A61B 5/15 |
| EP | 0 985 376 | 5/2000 | |
| EP | 1021950 | 7/2000 | |
| EP | 0894869 | 2/2001 | |
| EP | 1074832 | 2/2001 | ........... G01N 27/327 |
| EP | 1093854 | 4/2001 | |
| EP | 1 101 443 | 5/2001 | |
| EP | 1101443 A2 | 5/2001 | ............... A61B 5/15 |
| EP | 1114995 | 7/2001 | ........... G01N 33/487 |
| EP | 0736607 | 8/2001 | ........... G01N 27/327 |
| EP | 0874984 | 11/2001 | |
| EP | 1157660 | 11/2001 | ............... A61B 5/15 |
| EP | 0730037 | 12/2001 | |
| EP | 0636879 | 1/2002 | |
| EP | 01174083 | 1/2002 | ............... A61B 5/15 |
| EP | 0851224 | 3/2002 | ........... G01N 27/327 |
| EP | 0759553 | 5/2002 | ........... G01N 27/416 |
| EP | 0856586 | 5/2002 | |
| EP | 0817809 | 7/2002 | ............... C08G 77/26 |
| EP | 0872728 | 7/2002 | |
| EP | 0795748 | 8/2002 | ........... G01N 27/327 |
| EP | 0685737 | 9/2002 | ........... G01N 27/327 |
| EP | 0958495 | 11/2002 | |
| EP | 0937249 | 12/2002 | |
| EP | 1337182 | 8/2003 | |
| EP | 0880692 | 1/2004 | ........... G01N 27/327 |
| EP | 01374770 | 1/2004 | ............... A61B 5/15 |
| EP | 1404232 | 4/2004 | |
| EP | 1404233 | 4/2004 | |
| EP | 1246688 | 5/2004 | ............... B01D 71/10 |
| EP | 1486766 | 12/2004 | ............... G01N 1/00 |
| EP | 1492457 A1 | 1/2005 | |
| EP | 1502614 | 2/2005 | ........... A61M 5/172 |
| EP | 1643908 | 4/2006 | |
| EP | 1779780 A2 | 5/2007 | |
| EP | 1790288 | 5/2007 | ............... A61B 5/151 |
| EP | 1790288 A1 | 5/2007 | |
| EP | 1881322 A1 | 1/2008 | ........... G01N 33/487 |
| EP | 1921992 | 5/2008 | |
| EP | 2039294 | 3/2009 | ............ A61B 5/151 |
| EP | 2039294 A1 | 3/2009 | |
| EP | 2119396 A1 | 11/2009 | |
| EP | 2130493 A1 | 12/2009 | ............... A61B 5/15 |
| FR | 2 555 432 A | 5/1985 | |
| FR | 2555432 | 5/1985 | ............ A61B 10/00 |
| FR | 2622457 | 11/1987 | ............ A61M 5/20 |
| GB | 1558111 | 12/1979 | ............... A61B 5/05 |
| GB | 2168815 | 6/1986 | ............ G01N 27/30 |
| GB | 233936 A | 6/1999 | |
| GB | 2331936 | 6/1999 | ............... A61B 5/14 |
| GB | 2335860 | 10/1999 | ............... A61B 5/14 |
| GB | 2335860 A | 10/1999 | |
| GB | 2335990 | 10/1999 | ............... A61B 5/05 |
| GB | 2335990 A | 10/1999 | |
| JP | HEI 4 1992 194660 | 7/1992 | ............ G01N 27/28 |
| JP | 1996010208 | 12/1992 | |
| JP | 9-276235 | 10/1997 | ............... A61B 5/00 |
| JP | 1014906 | 1/1998 | ............... A61B 5/14 |
| JP | 2000-116768 | 4/2000 | ............... A61M 1/02 |
| JP | 2009082631 A | 4/2009 | |
| WO | WO 1980/01389 | 7/1980 | |
| WO | WO 1985/04089 | 9/1985 | |
| WO | WO 1986/07632 | 12/1985 | |
| WO | WO86/005966 | 10/1986 | ............... A61B 5/00 |
| WO | WO 1991/09139 | 6/1991 | |
| WO | WO92/003099 | 3/1992 | ............ A61B 17/32 |
| WO | WO92/006971 | 4/1992 | ........... C07D 401/06 |
| WO | WO92/07263 | 4/1992 | ............... C12Q 1/00 |
| WO | WO92/007468 | 5/1992 | ............ A01N 43/90 |
| WO | WO93/000044 | 1/1993 | ............ A61B 17/32 |
| WO | WO 93/02720 | 2/1993 | ............... A61M 5/00 |
| WO | WO 1993/06979 | 4/1993 | |
| WO | WO93/09723 | 5/1993 | ............ A61B 17/32 |
| WO | WO 93/12726 | 7/1993 | ............ A61B 17/34 |
| WO | WO 1993/25898 | 12/1993 | |
| WO | WO 1994/27140 | 11/1994 | |
| WO | WO 1994/29703 | 12/1994 | |
| WO | WO 1994/29704 | 12/1994 | |
| WO | WO 1994/29731 | 12/1994 | |
| WO | WO 1995/00662 | 1/1995 | |
| WO | WO 95/06240 | 3/1995 | |
| WO | WO 1995/06240 | 3/1995 | ............... G01N 21/77 |
| WO | WO 1995/10223 | 4/1995 | |
| WO | WO95/012583 | 5/1995 | ............ C07D 239/80 |
| WO | WO 1995/22597 | 8/1995 | |
| WO | WO96/014799 | 5/1996 | ............ A61B 17/32 |
| WO | WO 1996/30431 | 10/1996 | |
| WO | WO96/037148 | 11/1996 | ............... A61B 5/15 |
| WO | WO 1997/02359 | 1/1997 | |
| WO | WO 1997/02487 | 1/1997 | |
| WO | WO 97/11883 A1 | 4/1997 | |
| WO | WO 1997/11883 | 4/1997 | ............... B65B 1/00 |
| WO | WO 1997/18464 | 5/1997 | |
| WO | WO97/028741 | 8/1997 | ............... A61B 5/15 |
| WO | WO 1997/30344 | 8/1997 | |
| WO | WO 1997/42882 | 11/1997 | |
| WO | WO 1997/42888 | 11/1997 | ............... A61B 5/00 |
| WO | WO 1997/45720 | 12/1997 | |
| WO | WO 1998/03431 | 1/1998 | |
| WO | WO98/014436 | 4/1998 | ............... C07B 59/00 |
| WO | WO98/019609 | 5/1998 | ............ A61B 17/32 |
| WO | WO98/020867 | 5/1998 | ............ A61K 31/00 |
| WO | WO 1998/19159 | 5/1998 | |
| WO | WO 1998/20332 | 5/1998 | |
| WO | WO 1998/20348 | 5/1998 | |
| WO | WO 98/24373 | 6/1998 | ............ A61B 17/00 |
| WO | WO 1998/24366 | 6/1998 | |
| WO | WO 1998 24373 | 6/1998 | ............ A61B 17/00 |
| WO | WO 1998/35225 | 8/1998 | |
| WO | WO98/045276 | 10/1998 | ........... C07D 239/80 |

(56) References Cited

FOREIGN PATENT DOCUMENTS

| | | | |
|---|---|---|---|
| WO | WO 1999/03584 | 1/1999 | |
| WO | WO99/007295 | 2/1999 | |
| WO | WO 99/07431 A1 | 2/1999 | ............ A61M 25/06 |
| WO | WO 1999/05966 | 2/1999 | |
| WO | WO 1999/07431 | 2/1999 | ............ A61M 25/06 |
| WO | WO 1999/62576 | 3/1999 | |
| WO | WO 99/17854 | 4/1999 | ............... G06F 3/28 |
| WO | WO 99/18532 | 4/1999 | ............. G06F 19/00 |
| WO | WO 1999/19507 | 4/1999 | |
| WO | WO 1999/19717 | 4/1999 | |
| WO | WO 99/27483 | 6/1999 | ............. G06F 19/00 |
| WO | WO 1999/27852 | 6/1999 | |
| WO | WO 1999/13100 | 12/1999 | |
| WO | WO 1999/64580 | 12/1999 | |
| WO | WO 00/06024 | 2/2000 | ............... A61B 5/16 |
| WO | WO 00/09184 | 2/2000 | |
| WO | WO 00/11578 | 3/2000 | ............. G06F 17/40 |
| WO | WO 00/15103 | 3/2000 | ............. A61B 5/00 |
| WO | WO 00/17799 | 3/2000 | ............. G06F 17/60 |
| WO | WO 00/17800 | 3/2000 | ............. G06F 17/60 |
| WO | WO 00/18293 | 4/2000 | ............. A61B 5/00 |
| WO | WO 00/19346 | 4/2000 | ............. G06F 17/60 |
| WO | WO 2000/20626 | 4/2000 | ............... C12Q 1/00 |
| WO | WO00/029577 | 5/2000 | ......... C07K 14/705 |
| WO | WO 00/30186 | 5/2000 | ............. H01L 41/09 |
| WO | WO 00/32097 | 6/2000 | ............. A61B 5/00 |
| WO | WO 00/32098 | 6/2000 | ............. A61B 5/00 |
| WO | WO 00/33236 | 6/2000 | ............. G06F 159/00 |
| WO | WO 00/39914 | 7/2000 | |
| WO | WO 00/42422 | 7/2000 | |
| WO | WO 00/44084 | 7/2000 | ............. H02K 37/12 |
| WO | WO00/046854 | 8/2000 | ............. G02F 1/1333 |
| WO | WO 00/50771 | 8/2000 | ............... F03G 7/00 |
| WO | WO00/055915 | 9/2000 | ............. H01L 21/98 |
| WO | WO 00/60340 | 10/2000 | ........... G01N 27/237 |
| WO | WO 00/64022 | 10/2000 | ............... H02H 3/33 |
| WO | WO 00/67245 | 11/2000 | |
| WO | WO 00/67268 | 11/2000 | ............... H01H 1/00 |
| WO | WO 00/72452 | 11/2000 | ............. G06F 17/60 |
| WO | WO 01/00090 | 1/2001 | ............... A61B 5/15 |
| WO | WO 01/15807 | 3/2001 | |
| WO | WO 01/15807 A1 | 3/2001 | ............. B01L 3/100 |
| WO | WO 01/16578 A1 | 3/2001 | ............. G01N 21/35 |
| WO | WO 01/75433 | 3/2001 | |
| WO | WO 01/23885 | 4/2001 | ........... G01N 33/487 |
| WO | WO 01/25775 | 4/2001 | ............. G01N 27/30 |
| WO | WO 01/26813 | 4/2001 | ................. B01L 3/00 |
| WO | WO01/029037 | 4/2001 | ............. A61K 31/44 |
| WO | WO 01/33216 | 5/2001 | ........... G01N 33/487 |
| WO | WO 01/34029 | 5/2001 | ............. A61B 5/15 |
| WO | WO 01/36955 | 5/2001 | ........... G01N 27/327 |
| WO | WO 01/37174 | 5/2001 | ............. G06F 17/60 |
| WO | WO 01/45014 A1 | 6/2001 | ............. G06F 17/60 |
| WO | WO 01/40788 | 7/2001 | ........... G01N 27/237 |
| WO | WO 01/57510 | 8/2001 | ............. G01N 27/30 |
| WO | WO 2001/63271 | 8/2001 | ........... G01N 27/327 |
| WO | WO 01/64105 | 9/2001 | |
| WO | WO 01/66010 | 9/2001 | ............. A61B 5/15 |
| WO | WO 01/69505 | 9/2001 | ............. G06F 17/60 |
| WO | WO 01/72220 A | 10/2001 | |
| WO | WO 01/72220 A1 | 10/2001 | ............. A61B 5/00 |
| WO | WO 01/72225 | 10/2001 | ............. A61B 5/15 |
| WO | WO 01/73124 | 10/2001 | ............. C12Q 1/68 |
| WO | WO 01/73395 | 10/2001 | ............. G01N 1/00 |
| WO | WO 01/89691 | 11/2001 | |
| WO | WO 01/95806 | 12/2001 | ............. A61B 5/15 |
| WO | WO 2001/091634 A2 | 12/2001 | ............. A61B 5/00 |
| WO | WO 2001/95806 | 12/2001 | ............. A61B 5/15 |
| WO | WO 02/00101 | 1/2002 | |
| WO | WO 02/02796 | 1/2002 | |
| WO | WO 02/08750 | 1/2002 | |
| WO | WO 02/08753 | 1/2002 | |
| WO | WO 02/08950 | 1/2002 | |
| WO | WO 02/18940 | 3/2002 | |
| WO | WO 02/21317 | 3/2002 | ............. G06F 17/00 |
| WO | WO 02/25551 | 3/2002 | ............. G06F 17/60 |
| WO | WO 02/32559 | 4/2002 | |
| WO | WO 02/41227 | 5/2002 | ............. G06F 17/60 |
| WO | WO 02/41779 | 5/2002 | |
| WO | WO 02/44948 | 6/2002 | |
| WO | WO 2002/49507 | 6/2002 | ............. A61B 10/00 |
| WO | WO/0249507 | 6/2002 | ............. A61B 10/00 |
| WO | WO 2002/056769 | 7/2002 | ............... A61B 5/00 |
| WO | WO 02/059734 | 8/2002 | |
| WO | WO 02/069791 | 9/2002 | |
| WO | WO 02/077638 | 10/2002 | |
| WO | WO 02/100251 | 12/2002 | |
| WO | WO 02/100252 | 12/2002 | |
| WO | WO 02/100253 | 12/2002 | |
| WO | WO 02/100254 | 12/2002 | |
| WO | WO 02/100460 | 12/2002 | |
| WO | WO 02/100461 | 12/2002 | |
| WO | WO 02/101343 | 12/2002 | |
| WO | WO 02/101359 | 12/2002 | |
| WO | WO 03/000321 | 1/2003 | |
| WO | WO 03/023389 | 3/2003 | |
| WO | WO 03/042691 | 5/2003 | |
| WO | WO 03039369 A | 5/2003 | ............. A61B 10/00 |
| WO | WO 03/045557 | 6/2003 | |
| WO | WO 03/046542 | 6/2003 | |
| WO | WO 03/049609 | 6/2003 | |
| WO | WO 03/050534 | 6/2003 | |
| WO | WO 03/066128 | 8/2003 | |
| WO | WO 03/070099 | 8/2003 | |
| WO | WO 03/071940 | 9/2003 | |
| WO | WO 03/082091 | 10/2003 | ............... A61B 5/00 |
| WO | WO 03/082091 A2 | 10/2003 | |
| WO | WO 03/088834 | 10/2003 | ............... A61B 5/00 |
| WO | WO 03/088851 A1 | 10/2003 | ............. A61B 17/14 |
| WO | WO 2003/082091 | 10/2003 | ............... A61B 5/00 |
| WO | WO 2003/088824 | 10/2003 | ............... A61B 5/15 |
| WO | WO 2003/088834 | 10/2003 | ............... A61B 5/00 |
| WO | WO 2003/088835 | 10/2003 | ............... A61B 5/15 |
| WO | WO 2003/094752 | 11/2003 | |
| WO | WO 03/101297 | 12/2003 | |
| WO | WO 04/008130 | 1/2004 | |
| WO | WO 2004/022133 | 3/2004 | |
| WO | WO 04/026130 | 4/2004 | |
| WO | WO 04/040285 A2 | 5/2004 | |
| WO | WO 04/040287 A1 | 5/2004 | |
| WO | WO 04/040948 | 5/2004 | |
| WO | WO 04/041082 | 5/2004 | |
| WO | WO 2004/045375 | 6/2004 | ............... A61B 5/15 |
| WO | WO 04/054455 | 7/2004 | |
| WO | WO 04/060174 | 7/2004 | |
| WO | WO 04/060446 | 7/2004 | |
| WO | WO 04/091693 | 10/2004 | |
| WO | WO 04/098405 | 11/2004 | |
| WO | WO 04/107964 | 12/2004 | |
| WO | WO 04/107975 | 12/2004 | |
| WO | WO 04/112602 | 12/2004 | |
| WO | WO 2004/003147 | 12/2004 | |
| WO | WO 2004/107964 | 12/2004 | |
| WO | WO 2004/112612 | 12/2004 | ............... A61B 5/15 |
| WO | WO 2004/112612 A1 | 12/2004 | |
| WO | WO 05/001418 | 1/2005 | |
| WO | WO 2005/001418 | 1/2005 | |
| WO | WO 2005/006939 | 1/2005 | |
| WO | WO 2005/011774 | 2/2005 | |
| WO | WO 2005/013824 | 2/2005 | ............... A61B 5/15 |
| WO | WO 2005/016125 | 2/2005 | |
| WO | WO 05/022143 | 3/2005 | |
| WO | WO 2005/018425 | 3/2005 | |
| WO | WO 2005/018430 | 3/2005 | |
| WO | WO 2005/018454 | 3/2005 | |
| WO | WO 2005/018709 | 3/2005 | |
| WO | WO 2005/018710 | 3/2005 | |
| WO | WO 2005/018711 | 3/2005 | ............. A61B 17/32 |
| WO | WO 2005/023088 | 3/2005 | |
| WO | WO 2005/033659 | 4/2005 | |
| WO | WO 2005/034720 | 4/2005 | |
| WO | WO 2005/034721 | 4/2005 | |
| WO | WO 2005/034741 | 4/2005 | ............... A61B 5/00 |
| WO | WO 2005/034778 | 4/2005 | ............. A61M 17/32 |

(56) References Cited

FOREIGN PATENT DOCUMENTS

| | | | |
|---|---|---|---|
| WO | WO 2005/035017 | 4/2005 | |
| WO | WO 2005/035018 | 4/2005 | ............. A61B 17/34 |
| WO | WO 2005/037095 | 4/2005 | |
| WO | WO 2005/046477 | 5/2005 | |
| WO | WO 2005045414 A1 | 5/2005 | ............... C12Q 1/00 |
| WO | WO 2005/065399 | 7/2005 | |
| WO | WO 2005/065414 | 7/2005 | |
| WO | WO 2005/065415 | 7/2005 | |
| WO | WO 065545 A2 | 7/2005 | |
| WO | WO 05/072604 | 8/2005 | ................ A61B 5/00 |
| WO | WO05/084546 A2 | 9/2005 | ................ A61B 5/15 |
| WO | WO 2005/084557 | 9/2005 | ............. A61B 17/14 |
| WO | WO 2005/104948 | 11/2005 | ................ A61B 5/15 |
| WO | WO 2005/104948 A1 | 11/2005 | |
| WO | WO 05/116622 | 12/2005 | |
| WO | WO 05/119234 | 12/2005 | |
| WO | WO 05/121759 | 12/2005 | |
| WO | WO 2005/114185 | 12/2005 | ............. G01N 21/64 |
| WO | WO 2005/120197 | 12/2005 | ............. A61B 17/14 |
| WO | WO 2005/120199 | 12/2005 | ................ A61B 5/00 |
| WO | WO 2005/120365 | 12/2005 | ............. A61B 17/32 |
| WO | WO 2005/120365 A1 | 12/2005 | |
| WO | WO 06/001973 | 1/2006 | ................ A61B 5/15 |
| WO | WO 2006/001797 | 1/2006 | ............. A61B 17/14 |
| WO | WO 06/011062 | 2/2006 | |
| WO | WO 06/013045 | 2/2006 | ................ A61B 5/15 |
| WO | WO 2006/015615 | 2/2006 | ................ C12Q 1/00 |
| WO | WO 06/027702 A2 | 3/2006 | |
| WO | WO 06/032391 | 3/2006 | ................ A61B 5/15 |
| WO | WO 2006/031920 | 3/2006 | ................ A61B 5/00 |
| WO | WO-2006037646 A2 | 4/2006 | |
| WO | WO 2006/072004 | 7/2006 | |
| WO | WO 2006/105146 | 10/2006 | ................ A61B 5/05 |
| WO | WO 2006/116441 | 11/2006 | .............. A61B 5/151 |
| WO | WO 2007/010087 A2 | 1/2007 | .............. A61B 5/151 |
| WO | WO 2007/025635 | 3/2007 | ................ A61B 5/15 |
| WO | WO 2007/044834 | 4/2007 | ................ A61B 5/00 |
| WO | WO 2007/054335 | 5/2007 | ................ A61B 5/15 |
| WO | WO 2007/070719 | 6/2007 | ................ A61B 5/00 |
| WO | WO 2007/084367 | 7/2007 | ................ A61B 5/00 |
| WO | WO 2007/088905 A1 | 8/2007 | ............. A61B 5/1473 |
| WO | WO 2007/106470 | 9/2007 | ............. G01N 1/00 |
| WO | WO 2007/119900 | 10/2007 | .............. A61B 5/157 |
| WO | WO 2008/085052 A2 | 7/2008 | ................ A61B 5/15 |
| WO | WO 2008/112268 | 9/2008 | ............. A61B 17/32 |
| WO | WO 2008/112279 | 9/2008 | .............. A61B 5/155 |
| WO | WO 2010109461 A1 | 9/2010 | .............. A61B 5/151 |

OTHER PUBLICATIONS

A. Bott, W. Heineman, Chronocoulometry, Current Separations, 2004, 20, pp. 121.

\* cited by examiner

METHOD AND APPARATUS FOR A FLUID SAMPLING DEVICE

CROSS REFERENCE TO RELATED APPLICATIONS

This application is a National Stage Entry of PCT/US05/19445, which claims benefit of priority from provisional applications 60/577,376, filed Jun. 3, 2004 and 60/577,412, filed Jun. 3, 2004.

BACKGROUND OF THE INVENTION

Technical Field

The technical field relates to analyte detecting devices, and more specifically, device for obtaining a fluid sample.

Background Art

Lancing devices are known in the medical health-care products industry for piercing the skin to produce blood for analysis. Typically, a drop of blood for this type of analysis is obtained by making a small incision in the fingertip, creating a small wound, which generates a small blood droplet on the surface of the skin.

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. The device may be held against the skin and mechanically triggered to ballistically launch the lancet. Unfortunately, the pain associated with each lancing event using known technology discourages patients from testing. In addition to vibratory stimulation of the skin as the driver impacts the end of a launcher stop, known spring based devices have the possibility of firing lancets that harmonically oscillate against the patient tissue, causing multiple strikes due to recoil. This recoil and multiple strikes of the lancet is one major impediment to patient compliance with a structured glucose monitoring regime.

Success rate generally encompasses the probability of producing a blood sample with one lancing action, which is sufficient in volume to perform the desired analytical test. The blood may appear spontaneously at the surface of the skin, or may be "milked" from the wound. Milking generally involves pressing the side of the digit, or in proximity of the wound to express the blood to the surface. In traditional methods, the blood droplet produced by the lancing action must reach the surface of the skin to be viable for testing.

When using existing methods, blood often flows from the cut blood vessels but is then trapped below the surface of the skin, forming a hematoma. In other instances, a wound is created, but no blood flows from the wound. In either case, the lancing process cannot be combined with the sample acquisition and testing step. Spontaneous blood droplet generation with current mechanical launching system varies between launcher types but on average it is about 50% of lancet strikes, which would be spontaneous. Otherwise milking is required to yield blood. Mechanical launchers are unlikely to provide the means for integrated sample acquisition and testing if one out of every two strikes does not yield a spontaneous blood sample.

Many diabetic patients (insulin dependent) are required to self-test for blood glucose levels five to six times daily. The large number of steps required in traditional methods of glucose testing ranging from lancing, to milking of blood, applying blood to the test strip, and getting the measurements from the test strip discourages many diabetic patients from testing their blood glucose levels as often as recommended. Tight control of plasma glucose through frequent testing is therefore mandatory for disease management. The pain associated with each lancing event further discourages patients from testing. Additionally, the wound channel left on the patient by known systems may also be of a size that discourages those who are active with their hands or who are worried about healing of those wound channels from testing their glucose levels.

Another problem frequently encountered by patients who must use lancing equipment to obtain and analyze blood samples is the amount of manual dexterity and hand-eye coordination required to properly operate the lancing and sample testing equipment due to retinopathies and neuropathies particularly, severe in elderly diabetic patients. For those patients, operating existing lancet and sample testing equipment can be a challenge. Once a blood droplet is created, that droplet must then be guided into a receiving channel of a small test strip or the like. If the sample placement on the strip is unsuccessful, repetition of the entire procedure including re-lancing the skin to obtain a new blood droplet is necessary.

Early methods of using test strips required a relatively substantial volume of blood to obtain an accurate glucose measurement. This large blood requirement made the monitoring experience a painful one for the user since the user may need to lance deeper than comfortable to obtain sufficient blood generation. Alternatively, if insufficient blood is spontaneously generated, the user may need to "milk" the wound to squeeze enough blood to the skin surface. Neither method is desirable as they take additional user effort and may be painful. The discomfort and inconvenience associated with such lancing events may deter a user from testing their blood glucose levels in a rigorous manner sufficient to control their diabetes.

A further impediment to patient compliance is the amount of time that at lower volumes, it becomes even more important that blood or other fluid sample be directed to a measurement device without being wasted or spilled along the way. Known devices do not effectively handle the low sample volumes in an efficient manner. Accordingly, improved sensing devices are desired to increase user compliance and reduce the hurdles associated with analyte measurement.

A further concern is the use of blood glucose monitoring devices in a professional setting. For the professional health care market, single device multiple user is the norm. A sterility barrier between patients is required or a single use professional lancing device is used and then discarded after use. To interface an integrated point of care lancing, sampling and analyte detection device with a multiple user paradigm, each lancet analyte detecting member pair may be isolated from the previous and subsequent user.

SUMMARY OF THE INVENTION

The present invention provides solutions for at least some of the drawbacks discussed above. Specifically, some embodiments of the present invention provide an improved apparatus for improving the release of penetrating members from their cartridges. The present invention also provided improved techniques for indexing and rotating the cartridge. At least some of these and other objectives described herein will be met by embodiments of the present invention.

The present invention provides solutions for at least some of the drawbacks discussed above. Specifically, some embodiments of the present invention provide an improved apparatus for maintain sterility of a device being used on multiple users. The device described below functions to open the analyte detecting member channel and guide the sample into the analyte detecting member. It is then removed and discarded. Subsequent patient are protected as a new device is inserted to open the sensor at the time of lancing. The present invention may also provide improved techniques for manufacturing such analyte detecting devices. At least some of these and other objectives described herein will be met by embodiments of the present invention.

In one embodiment of the present invention, the method comprises obtaining a fluid sample by: removing the protective covering from the packaging exposing a single item of sterile barrier film by pulling on the tab provided; pressing the sterile barrier film to the front and underside of the case; preparing a penetrating member by operating the slider on the side of the device and depressing the fire button once; pressing the center circular cutout in the foam front of the barrier film against the patients skin in the area to be lanced; lancing the patient; and checking that the outer case of device has not been contaminated by blood and if necessary clean it with disinfectant.

Methods and apparatus are provided for manufacturing an analyte detecting device. In one embodiment, the method comprises obtaining a fluid sample by: removing the protective covering from the packaging exposing a single item of sterile barrier film by pulling on the tab provided; pressing the sterile barrier film to the front and underside of the case; preparing a penetrating member by operating the slider on the side of the device and depressing the fire button once; pressing the center circular cutout in the foam front of the barrier film against the patients skin in the area to be lanced; lancing the patient; and checking that the outer case of device has not been contaminated by blood and if necessary clean it with disinfectant.

In one embodiment of the present invention, a fluid sampling device is provided comprising a housing; a slider located on a surface of the housing, wherein the slider movable in a linear direction to rotate the cartridge to bring an unused penetrating member into position for use.

In one embodiment of the present invention, a fluid sampling device comprising a housing; a cartridge defining a plurality of cavities, the cartridge sized to fit within the housing; and a plurality of penetrating members at least partially contained in the cavities of the cartridge wherein the penetrating members are slidably movable to extend outward from the cartridge to penetrate tissue, the cavities each having a longitudinal opening providing access to an elongate portion of the penetrating member. The device may include a sterility barrier coupled to the cartridge, the sterility barrier covering a plurality of the longitudinal openings, wherein the sterility barrier covering the lateral openings is configured to be moved so that the elongate portion may be accessed by the gripper without touching the barrier; and a slider located on a surface of the housing, the slider movable in a linear direction to rotate the cartridge to bring an unused penetrating member into position for use. A tooth gear may be coupled to the slider to control a distance the slider can travel. A follower may be coupled to the slider. A cam surface may be engaged by the follower to lift the cartridge a desired distance above a first position to allow for rotation of the cartridge without engaging a gripper used to advance the penetrating member.

The cam surface may be aligned parallel to the slider. The linear motion of the cam rotates the cartridge and moves a plunger to break the sterility barrier on the cartridge. The cam surface comprise a linear strip of material with at least two raised portions and two depressed portions. The In one embodiment of the present invention, a device is provided for use in penetrating tissue to obtain a body fluid sample. The device comprises a cartridge; and a plurality of penetrating members slidably coupled to the cartridge, each of the penetrating members having a distal end sufficiently sharp to pierce tissue and each of the penetrating members being moveable relative to the other ones of the penetrating members, so that the distal end of the respective penetrating member is movable to penetrate tissue. Each of the penetrating members may be a bare lancet does not penetrate an outer sterility barrier during actuation.

In one embodiment of the present invention, a device may be provided comprising a cartridge having a plurality of cavities; and a plurality of penetrating members at least partially contained in the cavities of the single cartridge wherein the penetrating members are slidably movable to extend outward from lateral openings on the cartridge to penetrate tissue. A sterility barrier may be coupled to the cartridge, the sterility barrier covering a plurality of the lateral openings, wherein the sterility barrier covering the lateral openings is configured to be moved so that a penetrating member exits the lateral opening without contacting the barrier. The sterility barrier may cover the lateral openings and may be configured to be moved substantially vertically so that a penetrating member exits the lateral opening without contacting the barrier.

In one embodiment of the present invention, a device may be provided comprising a housing; a penetrating member driver; a cartridge containing a plurality of penetrating members; a display on the cartridge; and a linear slider on the housing, the slider coupled to a rod, wherein the rod moves with the slider, the rod having at least one roller. The device may use the linear motion of the slider to rotate the cartridge, punch open a new cavity and load a new penetrating member.

In one embodiment of the present invention, a method is provided for indexing. The method comprises moving a linear slider; the linear slider coupled to a rod; the rod moving with the slider, the rod having at least one roller; using the linear motion of the slider and linear motion of the rod to push at least one linear slider and to roll a roller along a linear cam surfaces to lift clear a drive assembly, rotate the cartridge, punch open a new cavity and load a new penetrating member.

In one embodiment of the present invention, a fluid sampling device is provided comprising a housing; a cartridge defining a plurality of cavities, the cartridge sized to fit within the housing; and a plurality of penetrating members at least partially contained in the cavities of the cartridge wherein the penetrating members are slidably movable to extend outward from the cartridge to penetrate tissue, the cavities each having a longitudinal opening providing access to an elongate portion of the penetrating member. A sterility barrier may be coupled to the cartridge, the sterility barrier covering a plurality of the longitudinal openings, wherein the sterility barrier covering the lateral openings is configured to be moved so that the elongate portion may be accessed by the gripper without touching the barrier; and a replaceable tissue interface barrier located on the housing, wherein the interface is replaced after each lancing event to prevent fluid contamination between different users.

Replaceable tissue interface may be positioned about an opening on the housing where the penetrating members extend outward to engage tissue on a user to obtain a fluid sample. Each of the cavities further include a lateral opening. Replaceable tissue interface may comprise a plurality of individually removable sheets of material, wherein one sheet is removed prior to each lancing event to uncover a sterile unused sheet to provide an uncontaminated surface for the next user to use.

In one embodiment of the present invention, a device is provided for use in penetrating tissue to obtain a body fluid sample. The device comprises a cartridge; and a plurality of penetrating members slidably coupled to the cartridge, each of the penetrating members having a distal end sufficiently sharp to pierce tissue and each of the penetrating members being moveable relative to the other ones of the penetrating members, so that the distal end of the respective penetrating member is movable to penetrate tissue; wherein each of the penetrating member is a bare lancet does not penetrate an outer, removable sterility barrier during actuation.

In one embodiment of the present invention, a device comprises a cartridge having a plurality of cavities; and a plurality of penetrating members at least partially contained in the cavities of the single cartridge wherein the penetrating members are slidably movable to extend outward from lateral openings on the cartridge to penetrate tissue; a sterility barrier coupled to the cartridge, the sterility barrier covering a plurality of the lateral openings, wherein the sterility barrier covering the lateral openings is configured to be moved so that a penetrating member exits the lateral opening without contacting the barrier. A fluid contamination barrier may be located on a housing the device, the barrier being removed and replaced by a clean barrier prior to each lancing event.

In one embodiment of the present invention, a method is provided for obtaining a fluid sample. The method comprises removing the protective covering from the packaging exposing a single item of sterile barrier film by pulling on the tab provided; pressing the sterile barrier film to the front and underside of the case; preparing a penetrating member by operating the slider on the side of the device and depressing the fire button once; pressing the center circular cutout in the foam front of the barrier film against the patients skin in the area to be lanced; lancing the patient; removing the barrier film from the front of the device; and checking that outer case of device has not been contaminated by blood and if necessary clean it with disinfectant.

In one embodiment of the present invention, a method is provided for obtaining a fluid sample. The method comprises preparing the skin of the patient in the area to be lanced with a sterile wipe; removing the protective covering from the packaging exposing a single item of sterile barrier film by pulling on the tab provided; removing the sterile barrier film from the carrier by pulling on the applicator tab provided; applying the adhesive side to the front area of the device ensuring that both the outer circular holes in the barrier film fit around the matching circular bosses on the front of the device; pressing the sterile barrier film to the front and underside of the case taking care not to touch the firing area of the barrier film; preparing a penetrating member by operating the slider on the side of the device and depressing the fire button once; pressing the center circular cutout in the foam front of the barrier film against the patients skin in the area to be lanced; lancing the patient by depressing the fire button a second time; removing the device from the patients skin and take the blood sample from their skin; removing the barrier film from the front of the device using the tab provided and dispose of it properly; and checking that outer case of device has not been contaminated by blood and if necessary clean it with disinfectant.

A further understanding of the nature and advantages of the invention will become apparent by reference to the remaining portions of the specification and drawings.

DESCRIPTION OF THE SPECIFIC EMBODIMENTS

The present invention provides a solution for body fluid sampling. Specifically, some embodiments of the present invention provides a method for improving release of penetrating members for a cartridge. The invention may use a high density penetrating member design. It may use penetrating members of smaller size, such as but not limited to diameter or length, than those of conventional penetrating members known in the art. The device may be used for multiple lancing events without having to remove a disposable from the device. The invention may provide improved sensing capabilities. At least some of these and other objectives described herein will be met by embodiments of the present invention.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

Figure 1:
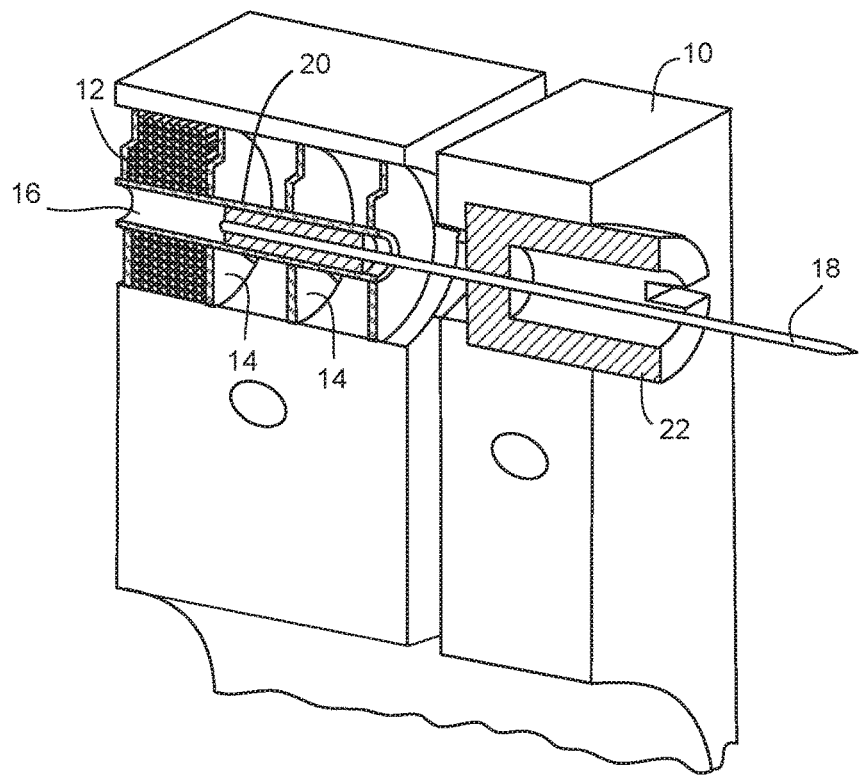
FIG. 1 illustrates an embodiment of a controllable force driver in the form of a cylindrical electric penetrating member driver using a coiled solenoid-type configuration.

The present invention may be used with a variety of different penetrating member drivers. It is contemplated that these penetrating member drivers may be spring based, solenoid based, magnetic driver based, nanomuscle based, or based on any other mechanism useful in moving a penetrating member along a path into tissue. It should be noted that the present invention is not limited by the type of driver used with the penetrating member feed mechanism. One suitable penetrating member driver for use with the present invention is shown in FIG. 1. This is an embodiment of a solenoid type electromagnetic driver that is capable of driving an iron core or slug mounted to the penetrating member assembly using a direct current (DC) power supply. The electromagnetic driver includes a driver coil pack that is divided into three separate coils along the path of the penetrating member, two end coils and a middle coil. Direct current is alternated to the coils to advance and retract the penetrating member. Although the driver coil pack is shown with three coils, any suitable number of coils may be used, for example, 4, 5, 6, 7 or more coils may be used.

Referring to the embodiment of FIG. 1, the stationary iron housing 10 may contain the driver coil pack with a first coil 12 flanked by iron spacers 14 which concentrate the magnetic flux at the inner diameter creating magnetic poles. The inner insulating housing 16 isolates the penetrating member 18 and iron core 20 from the coils and provides a smooth, low friction guide surface. The penetrating member guide 22 further centers the penetrating member 18 and iron core 20. The penetrating member 18 is protracted and retracted by alternating the current between the first coil 12, the middle coil, and the third coil to attract the iron core 20. Reversing the coil sequence and attracting the core and penetrating member back into the housing retracts the penetrating member. The penetrating member guide 22 also serves as a stop for the iron core 20 mounted to the penetrating member 18.

Figure 2A:
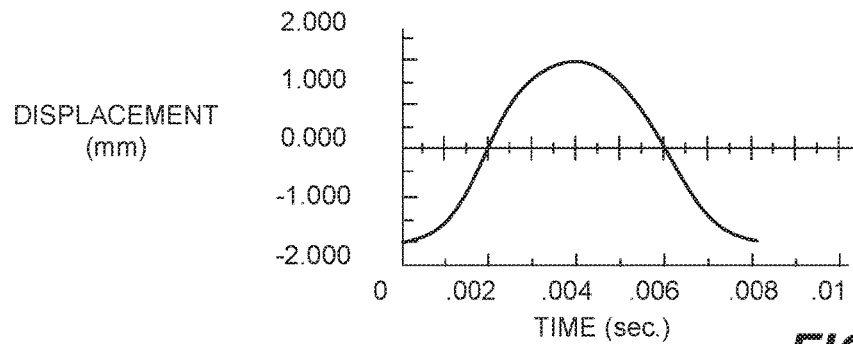
FIG. 2A illustrates a displacement over time profile of a penetrating member driven by a harmonic spring/mass system.
Figure 2B:
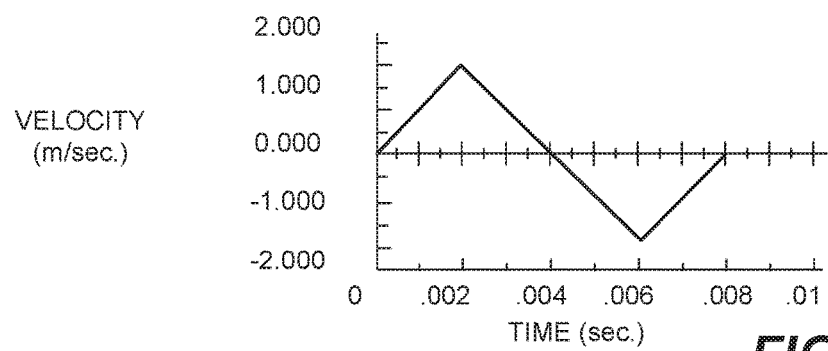
FIG. 2B illustrates the velocity over time profile of a penetrating member driver by a harmonic spring/mass system.
Figure 2C:
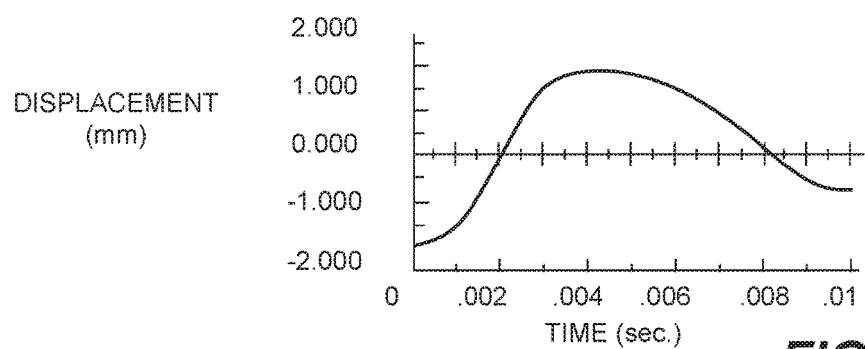
FIG. 2C illustrates a displacement over time profile of an embodiment of a controllable force driver.
Figure 2D:
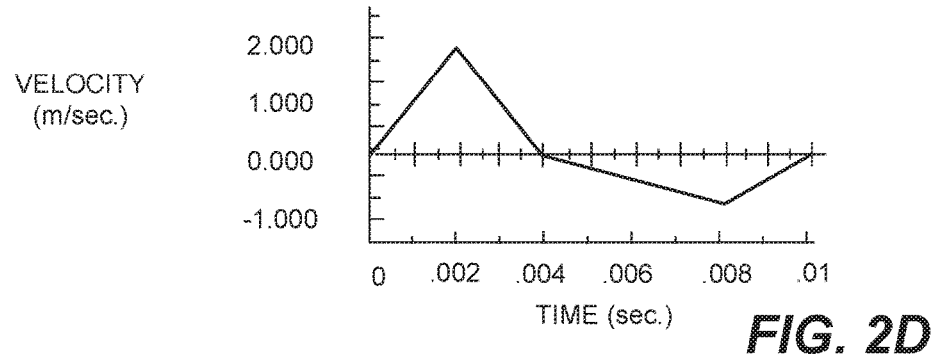
FIG. 2D illustrates a velocity over time profile of an embodiment of a controllable force driver.
Figure 3:
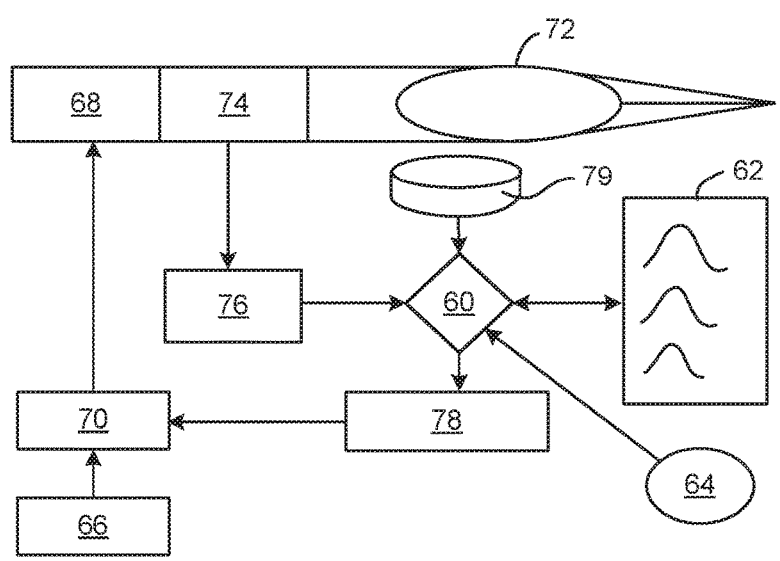
FIG. 3 is a diagrammatic view illustrating a controlled feed-back loop.

As discussed above, tissue penetration devices which employ spring or cam driving methods have a symmetrical or nearly symmetrical actuation displacement and velocity profiles on the advancement and retraction of the penetrating member as shown in FIGS. 2 and 3. In most of the available lancet devices, once the launch is initiated, the stored energy determines the velocity profile until the energy is dissipated. Controlling impact, retraction velocity, and dwell time of the penetrating member within the tissue can be useful in order to achieve a high success rate while accommodating variations in skin properties and minimize pain. Advantages can be achieved by taking into account of the fact that tissue dwell time is related to the amount of skin deformation as the penetrating member tries to puncture the surface of the skin and variance in skin deformation from patient to patient based on skin hydration.

In this embodiment, the ability to control velocity and depth of penetration may be achieved by use of a controllable force driver where feedback is an integral part of driver control. Such drivers can control either metal or, polymeric penetrating members or any other type of tissue penetration element. The dynamic control of such a driver is illustrated in FIG. 2C which illustrates an embodiment of a controlled displacement profile and FIG. 2D which illustrates an embodiment of a the controlled velocity profile. These are compared to FIGS. 2A and 2B, which illustrate embodiments of displacement and velocity profiles, respectively, of a harmonic spring/mass powered driver. Reduced pain can be achieved by using impact velocities of greater than about 2 m/s entry of a tissue penetrating element, such as a lancet, into tissue. Other suitable embodiments of the penetrating member driver are described in commonly assigned, copending U.S. patent application Ser. No. 10/127,395, filed Apr. 19, 2002 and previously incorporated herein.

FIG. 3 illustrates the operation of a feedback loop using a processor 60. The processor 60 stores profiles 62 in non-volatile memory. A user inputs information 64 about the desired circumstances or parameters for a lancing event. The processor 60 selects a driver profile 62 from a set of alternative driver profiles that have been preprogrammed in the processor 60 based on typical or desired tissue penetration device performance determined through testing at the factory or as programmed in by the operator. The processor 60 may customize by either scaling or modifying the profile based on additional user input information 64. Once the processor has chosen and customized the profile, the processor 60 is ready to modulate the power from the power supply 66 to the penetrating member driver 68 through an amplifier 70. The processor 60 may measure the location of the penetrating member 72 using a position sensing mechanism 74 through an analog to digital converter 76 linear encoder or other such transducer. Examples of position sensing mechanisms have been described in the embodiments above and may be found in the specification for commonly assigned, copending U.S. patent application Ser. No. 10/127,395, filed Apr. 19, 2002 and previously incorporated herein. The processor 60 calculates the movement of the penetrating member by comparing the actual profile of the penetrating member to the predetermined profile. The processor 60 modulates the power to the penetrating member driver 68 through a signal generator 78, which may control the amplifier 70 so that the actual velocity profile of the penetrating member does not exceed the predetermined profile by more than a preset error limit. The error limit is the accuracy in the control of the penetrating member.

After the lancing event, the processor 60 can allow the user to rank the results of the lancing event. The processor 60 stores these results and constructs a database 80 for the individual user. Using the database 79, the processor 60 calculates the profile traits such as degree of painlessness, success rate, and blood volume for various profiles 62 depending on user input information 64 to optimize the profile to the individual user for subsequent lancing cycles. These profile traits depend on the characteristic phases of penetrating member advancement and retraction. The processor 60 uses these calculations to optimize profiles 62 for each user. In addition to user input information 64, an internal clock allows storage in the database 79 of information such as the time of day to generate a time stamp for the lancing event and the time between lancing events to anticipate the user's diurnal needs. The database stores information and statistics for each user and each profile that particular user uses.

In addition to varying the profiles, the processor 60 can be used to calculate the appropriate penetrating member diameter and geometry suitable to realize the blood volume required by the user. For example, if the user requires about 1-5 microliter volume of blood, the processor 60 may select a 200 micron diameter penetrating member to achieve these results. For each class of lancet, both diameter and lancet tip geometry, is stored in the processor 60 to correspond with upper and lower limits of attainable blood volume based on the predetermined displacement and velocity profiles.

The lancing device is capable of prompting the user for information at the beginning and the end of the lancing event to more adequately suit the user. The goal is to either change to a different profile or modify an existing profile. Once the profile is set, the force driving the penetrating member is varied during advancement and retraction to follow the profile. The method of lancing using the lancing device comprises selecting a profile, lancing according to the selected profile, determining lancing profile traits for each characteristic phase of the lancing cycle, and optimizing profile traits for subsequent lancing events.

Figure 4:
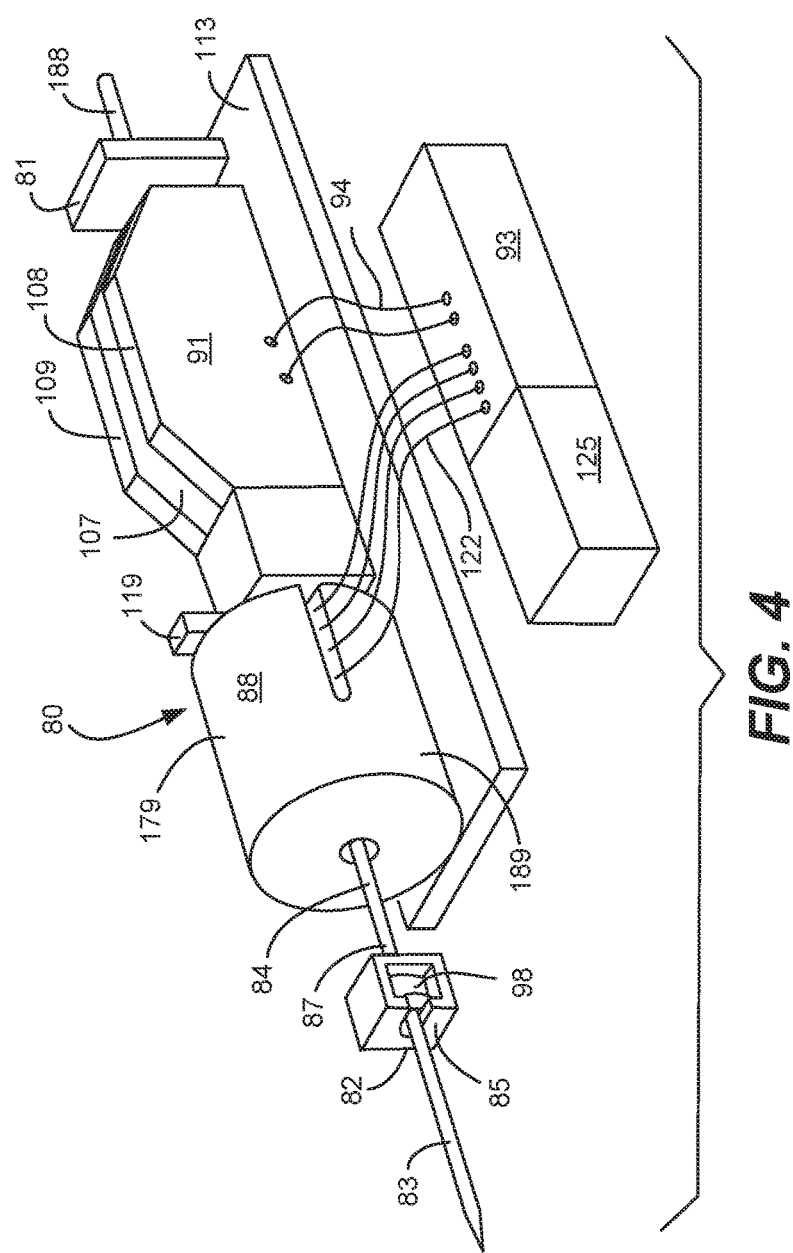
FIG. 4 is a perspective view of a tissue penetration device having features of the invention.

FIG. 4 illustrates an embodiment of a tissue penetration device, more specifically, a lancing device 80 that includes a controllable driver 179 coupled to a tissue penetration element. The lancing device 80 has a proximal end 81 and a distal end 82. At the distal end 82 is the tissue penetration element in the form of a penetrating member 83, which is coupled to an elongate coupler shaft 84 by a drive coupler 85. The elongate coupler shaft 84 has a proximal end 86 and a distal end 87. A driver coil pack 88 is disposed about the elongate coupler shaft 84 proximal of the penetrating member 83. A position sensor 91 is disposed about a proximal portion 92 of the elongate coupler shaft 84 and an electrical conductor 94 electrically couples a processor 93 to the position sensor 91. The elongate coupler shaft 84 driven by the driver coil pack 88 controlled by the position sensor 91 and processor 93 form the controllable driver, specifically, a controllable electromagnetic driver.

Figure 5:
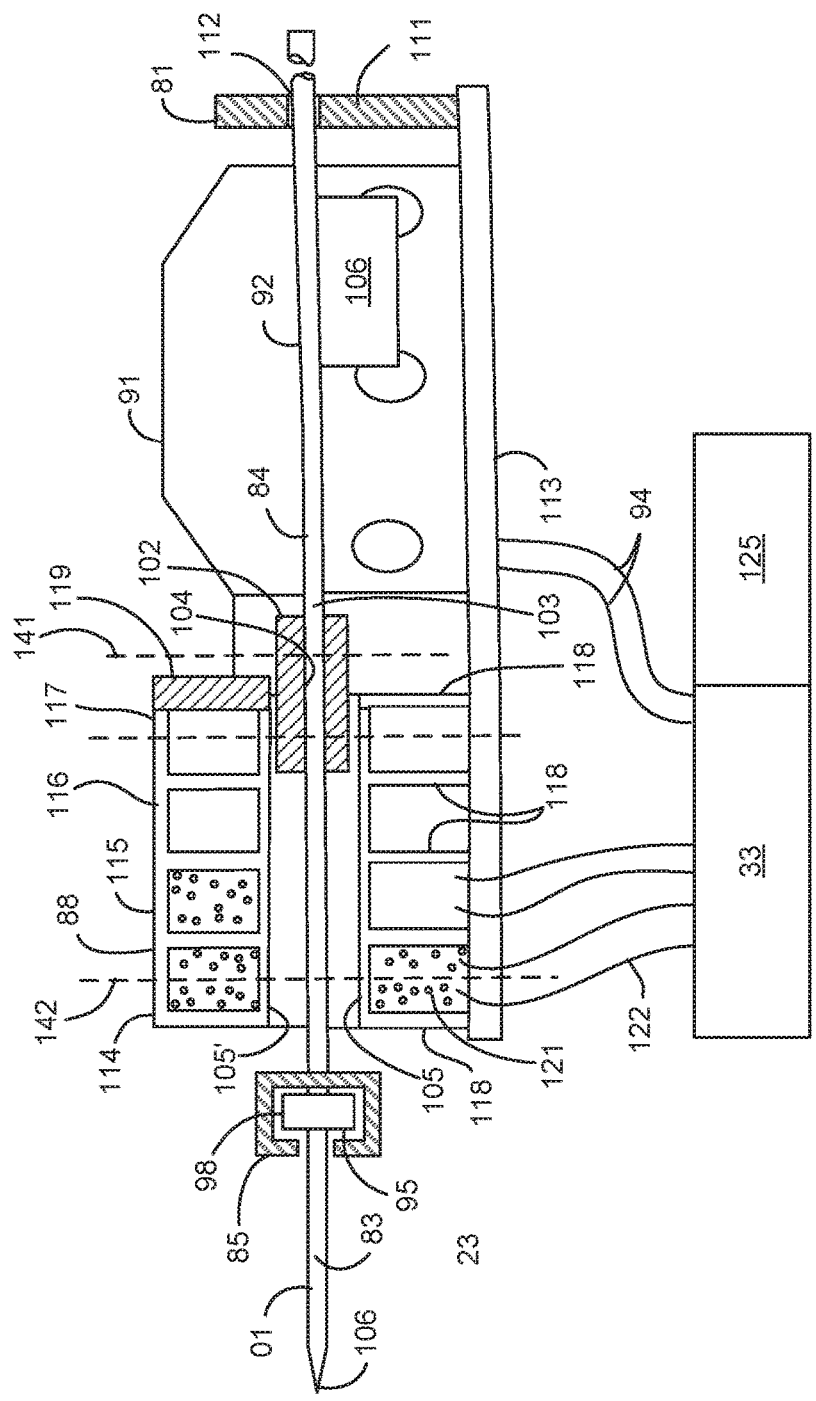
FIG. 5 is an elevation view in partial longitudinal section of the tissue penetration device of FIG. 4.

Referring to FIG. 5, the lancing device 80 can be seen in more detail, in partial longitudinal section. The penetrating member 83 has a proximal end 95 and a distal end 96 with a sharpened point at the distal end 96 of the penetrating member 83 and a drive head 98 disposed at the proximal end 95 of the penetrating member 83. A penetrating member shaft 201 is disposed between the drive head 98 and the sharpened point 97. The penetrating member shaft 201 may be comprised of stainless steel, or any other suitable material or alloy and have a transverse dimension of about 0.1 to about 0.4 mm. The penetrating member shaft may have a length of about 3 mm to about 50 mm, specifically, about 15 mm to about 20 mm. The drive head 98 of the penetrating member 83 is an enlarged portion having a transverse dimension greater than a transverse dimension of the penetrating member shaft 201 distal of the drive head 98. This configuration allows the drive head 98 to be mechanically captured by the drive coupler 85. The drive head 98 may have a transverse dimension of about 0.5 to about 2 mm.

A magnetic member 102 is secured to the elongate coupler shaft 84 proximal of the drive coupler 85 on a distal portion 203 of the elongate coupler shaft 84. The magnetic member 102 is a substantially cylindrical piece of magnetic material having an axial lumen 204 extending the length of the magnetic member 102. The magnetic member 102 has an outer transverse dimension that allows the magnetic member 102 to slide easily within an axial lumen 105 of a low friction, possibly lubricious, polymer guide tube 105' disposed within the driver coil pack 88. The magnetic member 102 may have an outer transverse dimension of about 1.0 to about 5.0 mm, specifically, about 2.3 to about 2.5 mm. The magnetic member 102 may have a length of about 3.0 to about 5.0 mm, specifically, about 4.7 to about 4.9 mm. The magnetic member 102 can be made from a variety of magnetic materials including ferrous metals such as ferrous steel, iron, ferrite, or the like. The magnetic member 102 may be secured to the distal portion 203 of the elongate coupler shaft 84 by a variety of methods including adhesive or epoxy bonding, welding, crimping or any other suitable method.

Proximal of the magnetic member 102, an optical encoder flag 206 is secured to the elongate coupler shaft 84. The optical encoder flag 206 is configured to move within a slot 107 in the position sensor 91. The slot 107 of the position sensor 91 is formed between a first body portion 108 and a second body portion 109 of the position sensor 91. The slot 107 may have separation width of about 1.5 to about 2.0 mm. The optical encoder flag 206 can have a length of about 14 to about 18 mm, a width of about 3 to about 5 mm and a thickness of about 0.04 to about 0.06 mm.

The optical encoder flag 206 interacts with various optical beams generated by LEDs disposed on or in the position sensor body portions 108 and 109 in a predetermined manner. The interaction of the optical beams generated by the LEDs of the position sensor 91 generates a signal that indicates the longitudinal position of the optical flag 206 relative to the position sensor 91 with a substantially high degree of resolution. The resolution of the position sensor 91 may be about 200 to about 400 cycles per inch, specifically, about 350 to about 370 cycles per inch. The position sensor 91 may have a speed response time (position/time resolution) of 0 to about 120,000 Hz, where one dark and light stripe of the flag constitutes one Hertz, or cycle per second. The position of the optical encoder flag 206 relative to the magnetic member 102, driver coil pack 88 and position sensor 91 is such that the optical encoder 91 can provide precise positional information about the penetrating member 83 over the entire length of the penetrating member's power stroke.

An optical encoder that is suitable for the position sensor 91 is a linear optical incremental encoder, model HEDS 9200, manufactured by Agilent Technologies. The model HEDS 9200 may have a length of about 20 to about 30 mm, a width of about 8 to about 12 mm, and a height of about 9 to about 11 mm. Although the position sensor 91 illustrated is a linear optical incremental encoder, other suitable position sensor embodiments could be used, provided they posses the requisite positional resolution and time response. The HEDS 9200 is a two channel device where the channels are 90 degrees out of phase with each other. This results in a resolution of four times the basic cycle of the flag. These quadrature outputs make it possible for the processor to determine the direction of penetrating member travel. Other suitable position sensors include capacitive encoders, analog reflective sensors, such as the reflective position sensor discussed above, and the like.

A coupler shaft guide 111 is disposed towards the proximal end 81 of the lancing device 80. The guide 111 has a guide lumen 112 disposed in the guide 111 to slidingly accept the proximal portion 92 of the elongate coupler shaft 84. The guide 111 keeps the elongate coupler shaft 84 centered horizontally and vertically in the slot 102 of the optical encoder 91.

Figure 6:
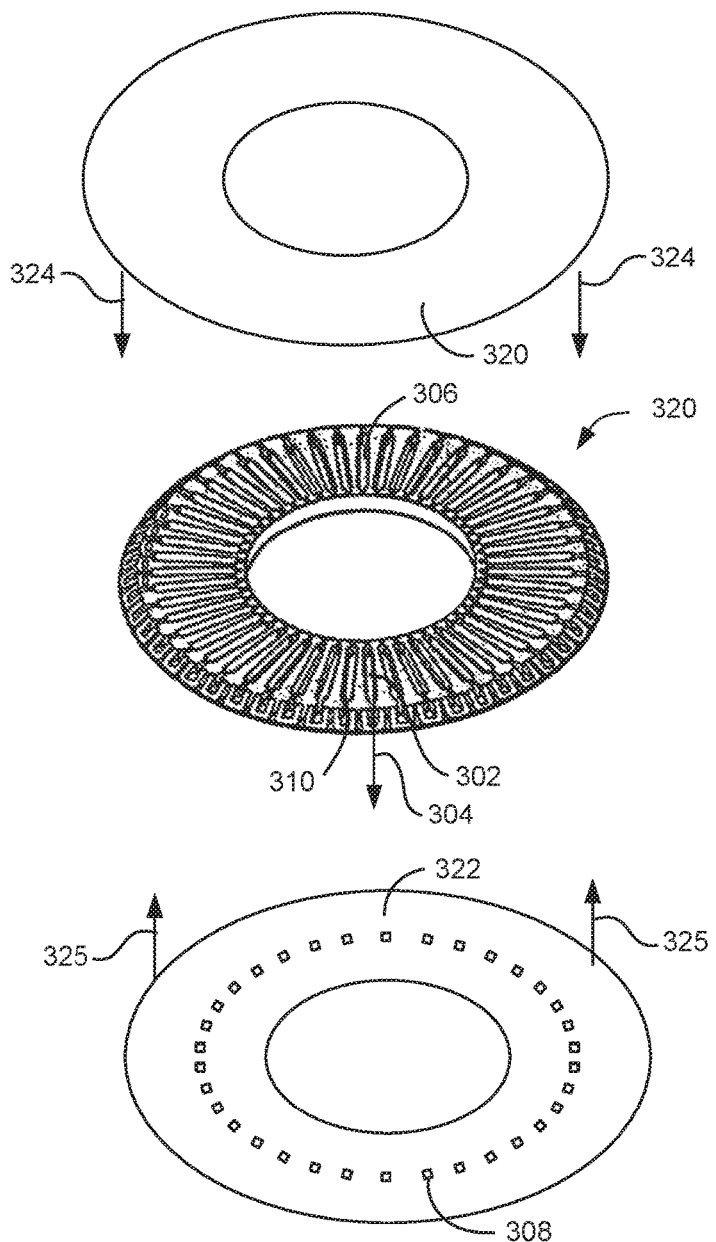
FIG. 6 shows an exploded perspective view of one embodiment of a device according to the present invention.

Referring now to FIG. 6, a still further embodiment of a cartridge according to the present invention will be described. FIG. 6 shows one embodiment of a cartridge 300 which may be removably inserted into an apparatus for driving penetrating members to pierce skin or tissue. The cartridge 300 has a plurality of penetrating members 302 that may be individually or otherwise selectively actuated so that the penetrating members 302 may extend outward from the cartridge, as indicated by arrow 304, to penetrate tissue. In the present embodiment, the cartridge 300 may be based on a flat disc with a number of penetrating members such as, but in no way limited to, (25, 50, 75, 100, . . . ) arranged radially on the disc or cartridge 800. It should be understood that although the cartridge 300 is shown as a disc or a disc-shaped housing, other shapes or configurations of the cartridge may also work without departing from the spirit of the present invention of placing a plurality of penetrating members to be engaged, singly or in some combination, by a penetrating member driver.

Each penetrating member 302 may be contained in a cavity 306 in the cartridge 300 with the penetrating member's sharpened end facing radially outward and may be in the same plane as that of the cartridge. The cavity 306 may be molded, pressed, forged, or otherwise formed in the cartridge. Although not limited in this manner, the ends of the cavities 306 may be divided into individual fingers (such as one for each cavity) on the outer periphery of the disc. The particular shape of each cavity 306 may be designed to suit the size or shape of the penetrating member therein or the amount of space desired for placement of the analyte detecting members 808. For example and not limitation, the cavity 306 may have a V-shaped cross-section, a U-shaped cross-section, C-shaped cross-section, a multi-level cross section or the other cross-sections. The opening 810 through which a penetrating member 302 may exit to penetrate tissue may also have a variety of shapes, such as but not limited to, a circular opening, a square or rectangular opening, a U-shaped opening, a narrow opening that only allows the penetrating member to pass, an opening with more clearance on the sides, a slit, a configuration as shown in FIG. 75, or the other shapes.

In this embodiment, after actuation, the penetrating member 302 is returned into the cartridge and may be held within the cartridge 300 in a manner so that it is not able to be used again. By way of example and not limitation, a used penetrating member may be returned into the cartridge and held by the launcher in position until the next lancing event. At the time of the next lancing, the launcher may disengage the used penetrating member with the cartridge 300 turned or indexed to the next clean penetrating member such that the cavity holding the used penetrating member is position so that it is not accessible to the user (i.e. turn away from a penetrating member exit opening). In some embodiments, the tip of a used penetrating member may be driven into a protective stop that hold the penetrating member in place after use. The cartridge 300 is replaceable with a new cartridge 300 once all the penetrating members have been used or at such other time or condition as deemed desirable by the user.

Referring still to the embodiment in FIG. 6, the cartridge 300 may provide sterile environments for penetrating members via seals, foils, covers, polymeric, or similar materials used to seal the cavities and provide enclosed areas for the penetrating members to rest in. In the present embodiment, a foil or seal layer 320 is applied to one surface of the cartridge 300. The seal layer 320 may be made of a variety of materials such as a metallic foil or other seal materials and may be of a tensile strength and other quality that may provide a sealed, sterile environment until the seal layer 320 is penetrate by a suitable or penetrating device providing a preselected or selected amount of force to open the sealed, sterile environment. Each cavity 306 may be individually sealed with a layer 320 in a manner such that the opening of one cavity does not interfere with the sterility in an adjacent or other cavity in the cartridge 800. As seen in the embodiment of FIG. 6, the seal layer 320 may be a planar material that is adhered to a top surface of the cartridge 800.

Depending on the orientation of the cartridge 300 in the penetrating member driver apparatus, the seal layer 320 may be on the top surface, side surface, bottom surface, or other positioned surface. For ease of illustration and discussion of the embodiment of FIG. 6, the layer 320 is placed on a top surface of the cartridge 800. The cavities 306 holding the penetrating members 302 are sealed on by the foil layer 320 and thus create the sterile environments for the penetrating members. The foil layer 320 may seal a plurality of cavities 306 or only a select number of cavities as desired.

In a still further feature of FIG. 6, the cartridge 300 may optionally include a plurality of analyte detecting members 308 on a substrate 822 which may be attached to a bottom surface of the cartridge 300. The substrate may be made of a material such as, but not limited to, a polymer, a foil, or other material suitable for attaching to a cartridge and holding the analyte detecting members 308. As seen in FIG. 6, the substrate 322 may hold a plurality of analyte detecting members, such as but not limited to, about 10-50, 50-100, or other combinations of analyte detecting members. This facilitates the assembly and integration of analyte detecting members 308 with cartridge 300. These analyte detecting members 308 may enable an integrated body fluid sampling system where the penetrating members 302 create a wound tract in a target tissue, which expresses body fluid that flows into the cartridge for analyte detection by at least one of the analyte detecting members 308. The substrate 322 may contain any number of analyte detecting members 308 suitable for detecting analytes in cartridge having a plurality of cavities 306. In one embodiment, many analyte detecting members 308 may be printed onto a single substrate 322 which is then adhered to the cartridge to facilitate manufacturing and simplify assembly. The analyte detecting members 308 may be electrochemical in nature. The analyte detecting members 308 may further contain enzymes, dyes, or other detectors which react when exposed to the desired analyte. Additionally, the analyte detecting members 308 may comprise of clear optical windows that allow light to pass into the body fluid for analyte analysis. The number, location, and type of analyte detecting member 308 may be varied as desired, based in part on the design of the cartridge, number of analytes to be measured, the need for analyte detecting member calibration, and the sensitivity of the analyte detecting members. If the cartridge 300 uses an analyte detecting member arrangement where the analyte detecting members are on a substrate attached to the bottom of the cartridge, there may be through holes (as shown in FIG. 76), wicking elements, capillary tube or other devices on the cartridge 300 to allow body fluid to flow from the cartridge to the analyte detecting members 308 for analysis. In other configurations, the analyte detecting members 308 may be printed, formed, or otherwise located directly in the cavities housing the penetrating members 302 or areas on the cartridge surface that receive blood after lancing.

The use of the seal layer 320 and substrate or analyte detecting member layer 822 may facilitate the manufacture of these cartridges 10. For example, a single seal layer 320 may be adhered, attached, or otherwise coupled to the cartridge 300 as indicated by arrows 324 to seal many of the cavities 306 at one time. A sheet 322 of analyte detecting members may also be adhered, attached, or otherwise coupled to the cartridge 300 as indicated by arrows 325 to provide many analyte detecting members on the cartridge at one time. During manufacturing of one embodiment of the present invention, the cartridge 300 may be loaded with penetrating members 302, sealed with layer 320 and a temporary layer (not shown) on the bottom where substrate 322 would later go, to provide a sealed environment for the penetrating members. This assembly with the temporary bottom layer is then taken to be sterilized. After sterilization, the assembly is taken to a clean room (or it may already be in a clear room or equivalent environment) where the temporary bottom layer is removed and the substrate 322 with analyte detecting members is coupled to the cartridge as shown in FIG. 6. This process allows for the sterile assembly of the cartridge with the penetrating members 302 using processes and/or temperatures that may degrade the accuracy or functionality of the analyte detecting members on substrate 322. As a nonlimiting example, the entire cartridge 300 may then be placed in a further sealed container such as a pouch, bag, plastic molded container, etc. . . . to facilitate contact, improve ruggedness, and/or allow for easier handling.

In some embodiments, more than one seal layer 320 may be used to seal the cavities 306. As examples of some embodiments, multiple layers may be placed over each cavity 306, half or some selected portion of the cavities may be sealed with one layer with the other half or selected portion of the cavities sealed with another sheet or layer, different shaped cavities may use different seal layer, or the like. The seal layer 320 may have different physical properties, such as those covering the penetrating members 302 near the end of the cartridge may have a different color such as red to indicate to the user (if visually inspectable) that the user is down to say 10, 5, or other number of penetrating members before the cartridge should be changed out.

Figure 7:
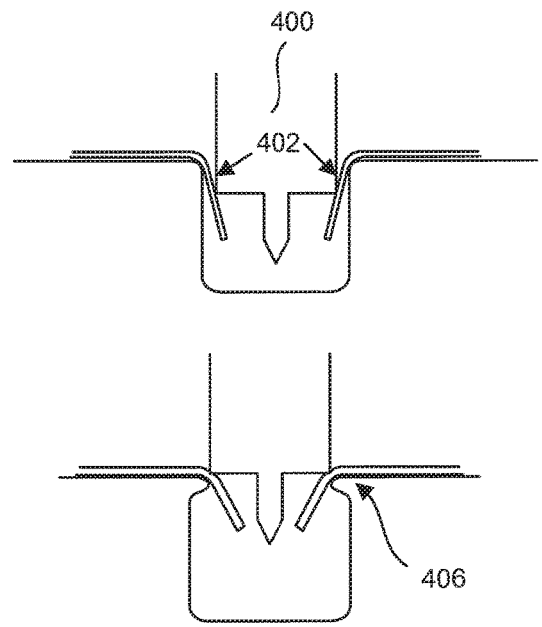
FIG. 7 shows a cross-sectional view of one embodiment of a punch according to the present invention.
Figure 8:
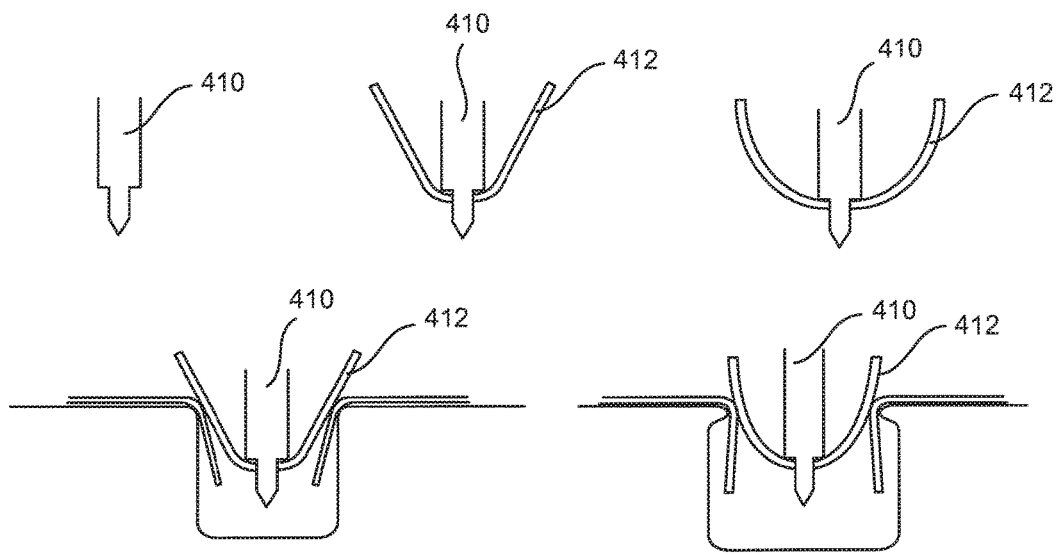
FIG. 8 shows another embodiment of a punch according to the present invention.

Referring now to FIGS. 7 and 8, various embodiments of the present invention will now be described in further detail. Improvements have been made to the punch device 400. The present invention addresses issues with the punch moving the cut foil to the sides of the chamber, so that the foil springs back and you get some end effects where the punch angles the foil into the corner, resulting in tearing rather than a clean cut to open the sterility barrier. The gripper has to bend the foil out of the way, as it runs along the channel and this results in the half Newton range or force required.

FIG. 7 shows an embodiment of the punch 400 with a widened portion 402 that tightly fits against the opening of the cavity. Some embodiments may also have a flash portion 406 that interferes with the punch 400 during punching. The helps push the flaps of the foil to the side and does not interfere with the gripper during travel.

FIG. 8 shows yet another embodiment with a narrow punch 410 with winged portions 412. The wings 412 are of sufficient size and stiffness to push the foil pieces against the side of the cavities.

Referring now to FIGS. 9 through 16, a still further embodiment of the present invention describes a shield or guide rail attached to the gripper and not the punch. Thus the shield is in placed while the gripper is coupled to the penetrating member. It does not need to be fitted to be exactly the same size as the cavity width, such as may be needed by a punch, thus allowing for easier manufacturability.

Figure 9:
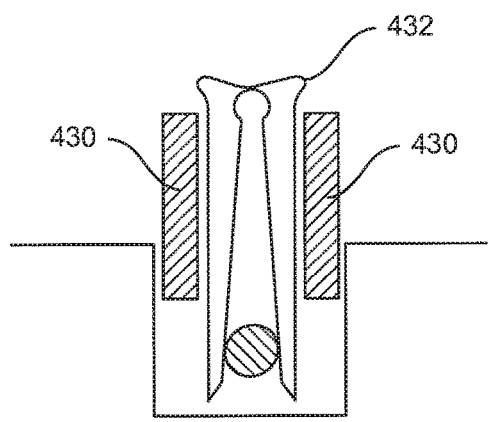
FIG. 9 shows one embodiment of a gripper with a shield.
Figure 10:
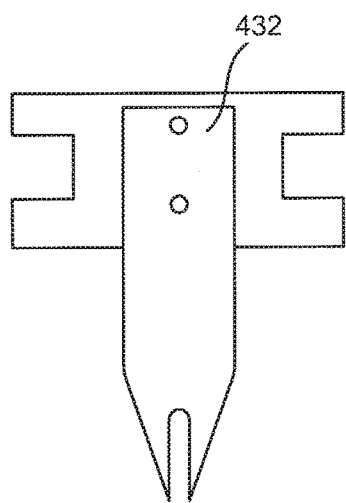
FIGS. 10-12 show other embodiments of a gripper.

Referring now to FIGS. 9 and 10, in this embodiment the shield 430 is mounted above the gripper 432. This hollow open channel rides over the gripper and is fixed to the track. It also guards from accidentally touching the gripper itself. The present invention uses the guard to bend the foil out of the way.

Figure 11:
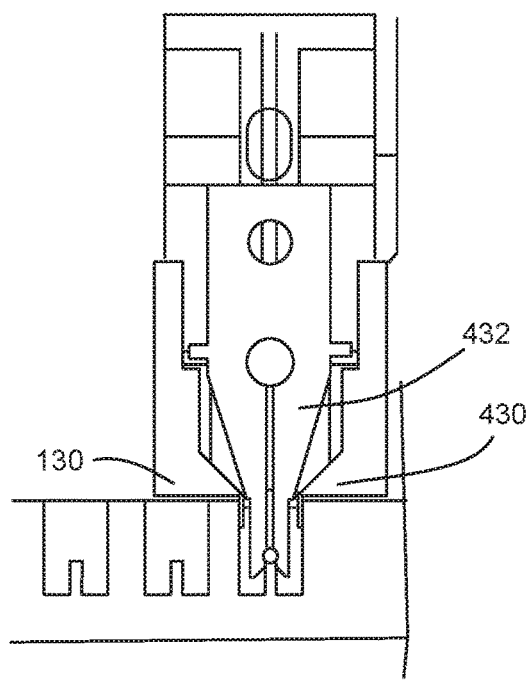
Figure 12:
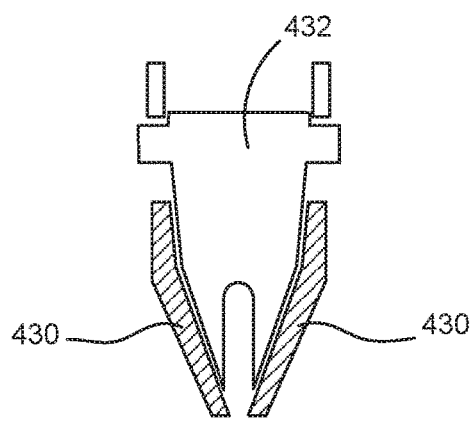
Figure 13:
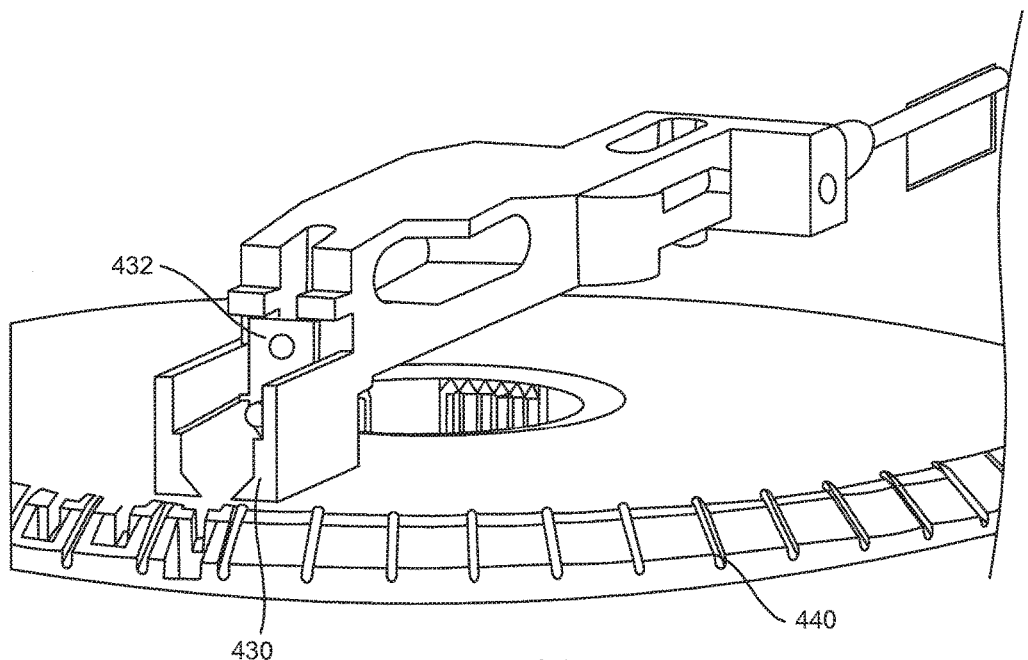
FIGS. 13-14 show embodiments of a gripper and a drive assembly.
Figure 14:
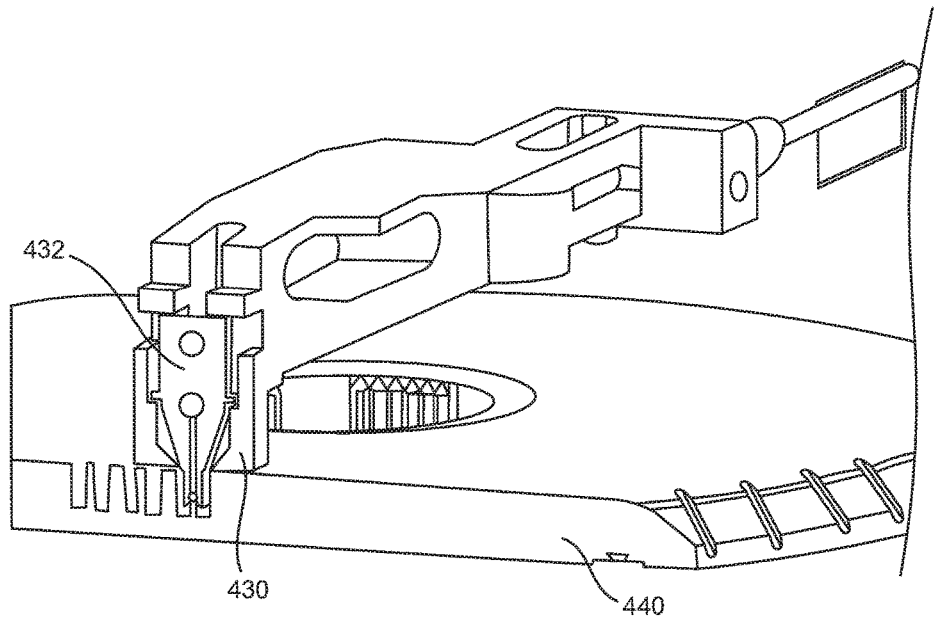

Referring now to FIG. 11, a view of the gripper 432 engaged to a penetrating member and a shield 430 pushing foil aside is shown. FIG. 12 shows yet another cross-section of the gripper 432 and shield 430. FIGS. 13 and 14 shows yet another depiction with the entire gripper and drive assembly positioned over a cartridge 440 containing a plurality of penetrating members.

Figure 15:
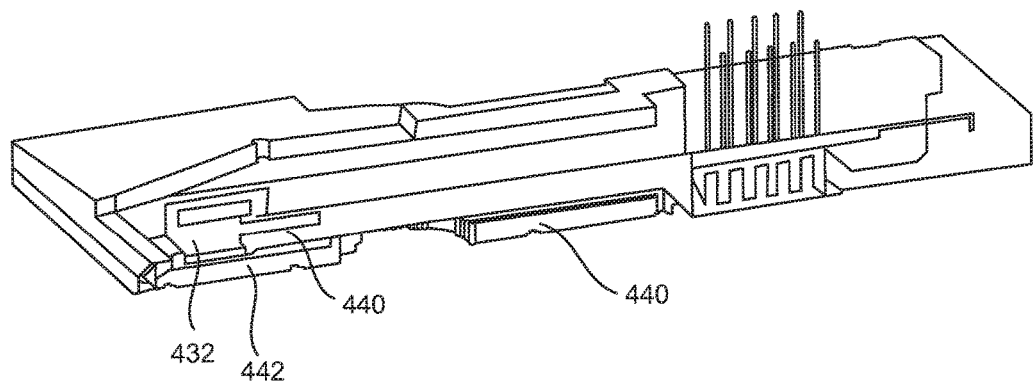
FIGS. 15-16 show a cross-section and side view of one embodiment of the gripper and the drive assembly.
Figure 16:
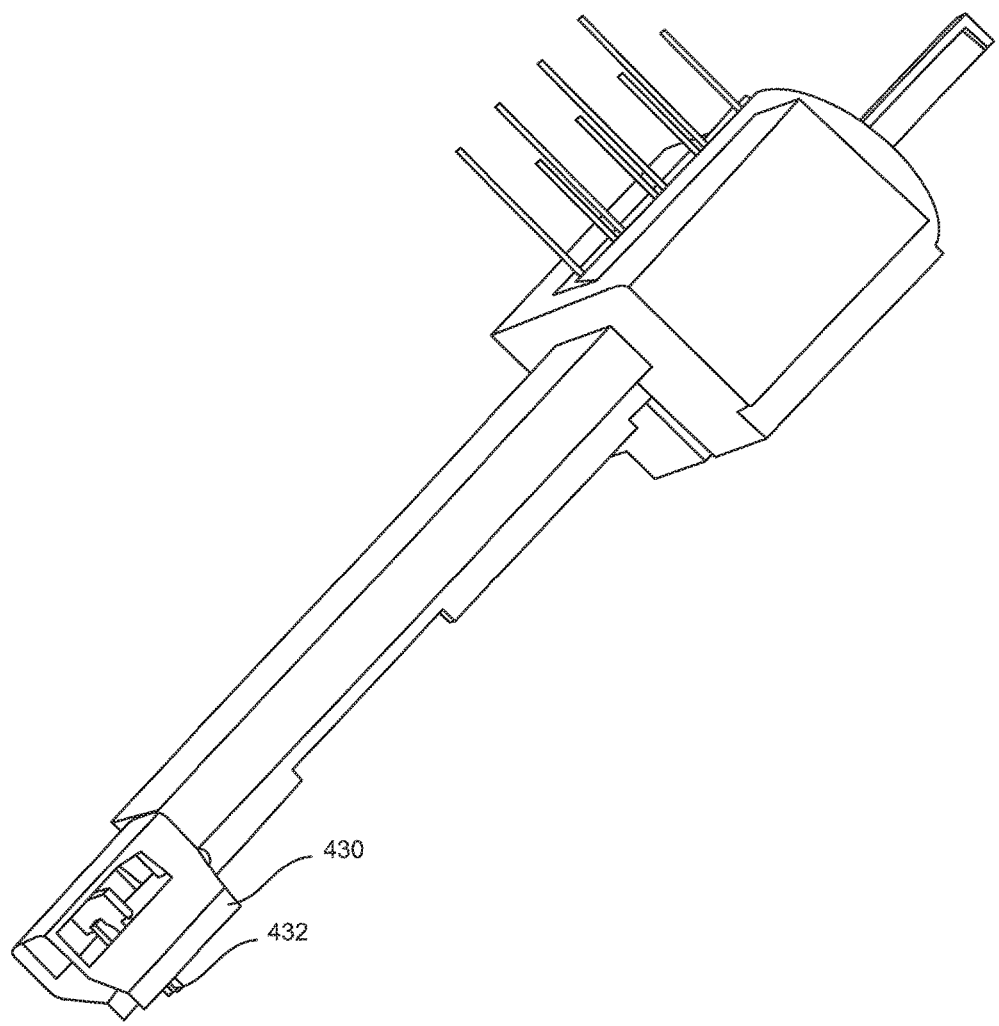

FIG. 15 shows a cross-section view with the entire gripper and drive assembly positioned over a cartridge 440 containing a plurality of penetrating members 442. FIG. 16 shows a perspective view of just the gripper and drive assembly.

In yet another embodiment of the present invention, there is now a new type of punch proposed which will result in less friction and may be able to avoid a razor sharp blade and use a blunt blade instead. This punch has an "H" blade leaving an "H" cut which the guard now can fold nicely out of the way. The blade may be angled like a guillotine with feet at either end to reduce the force needed to cut open the foil and hence we could maybe increase the foil thickness (we are at 12 microns and would like to be at 20 to avoid pinholes (and hence bacteria/spores)

In a still further embodiment, the present invention may include an improved armature design. In one embodiment, the armature is made stiffer, by increasing diameter of the rod or going to a rectangular cross section in the place that suffers the most deflection. Bearings can also be modified (in the cartridge); currently it is a round lancet in a square bearing. The plan is to set the lancet in a "V" channel and then to provide a light downward force pressing the lancet into the "V". As the lancet wants to move due to the asymmetrical chamfer, that force will be overcome and then it can move in compliance with eh chamfer force. We apply this force to the top of the gripper using a "V" shape top on the gripper, the gripper is now stabilized so that it cant rattle around, while maintaining the compliance for the lancet to move because of the chamfer. The end result is dampening of the oscillations in the armature, thus reducing the jitter.

Space: to reduce the length of the travel of the slider due to space constraints. One solution would be to ramp quickly and ramp up only when needed, therefore it becomes a non-linear cam arrangement. This gets us reduced length. In addition, it allows us to shorten the stroke. To get height for PCB we can go from a double-sided cam to a single sided cam with a spring to provide the force in two directions.

Figure 17:
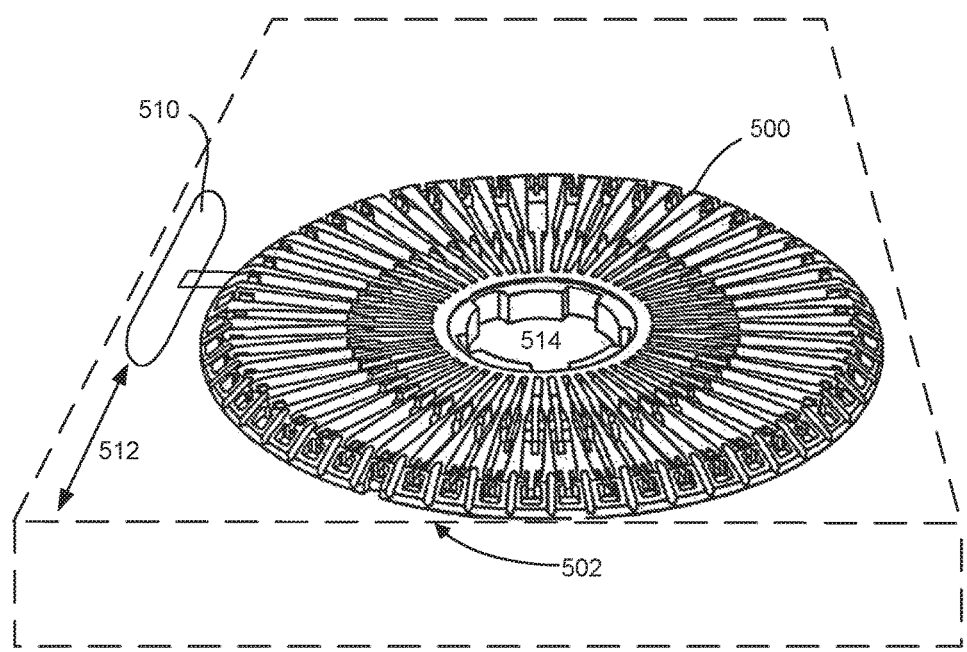
FIG. 17 shows a schematic of one embodiment of a slider used to rotate a disc.

Referring now to FIG. 17, yet another aspect of the present invention will now be described. To bring a new, unused penetrating member to use, the cartridge 500 may be rotated as indicated by arrow 502. A linear slider 510 moves forward and backward as indicated by arrow 512. The forward motion of the slider 510 rotates the cartridge, among other things. In some embodiments, backward motion may be used to rotate the cartridge (it all depends on where the slider starts). Rotation occurs when a keyed gear (not shown) that the opening 514 fits over is rotated by motion of the slider 510. Of course, the slider 510 in the present embodiment also actuates a plurality of other motions such as clearing the gripper, shield, and drive assembly, to lift them clear so that the cartridge 500 can rotate.

Figure 18:
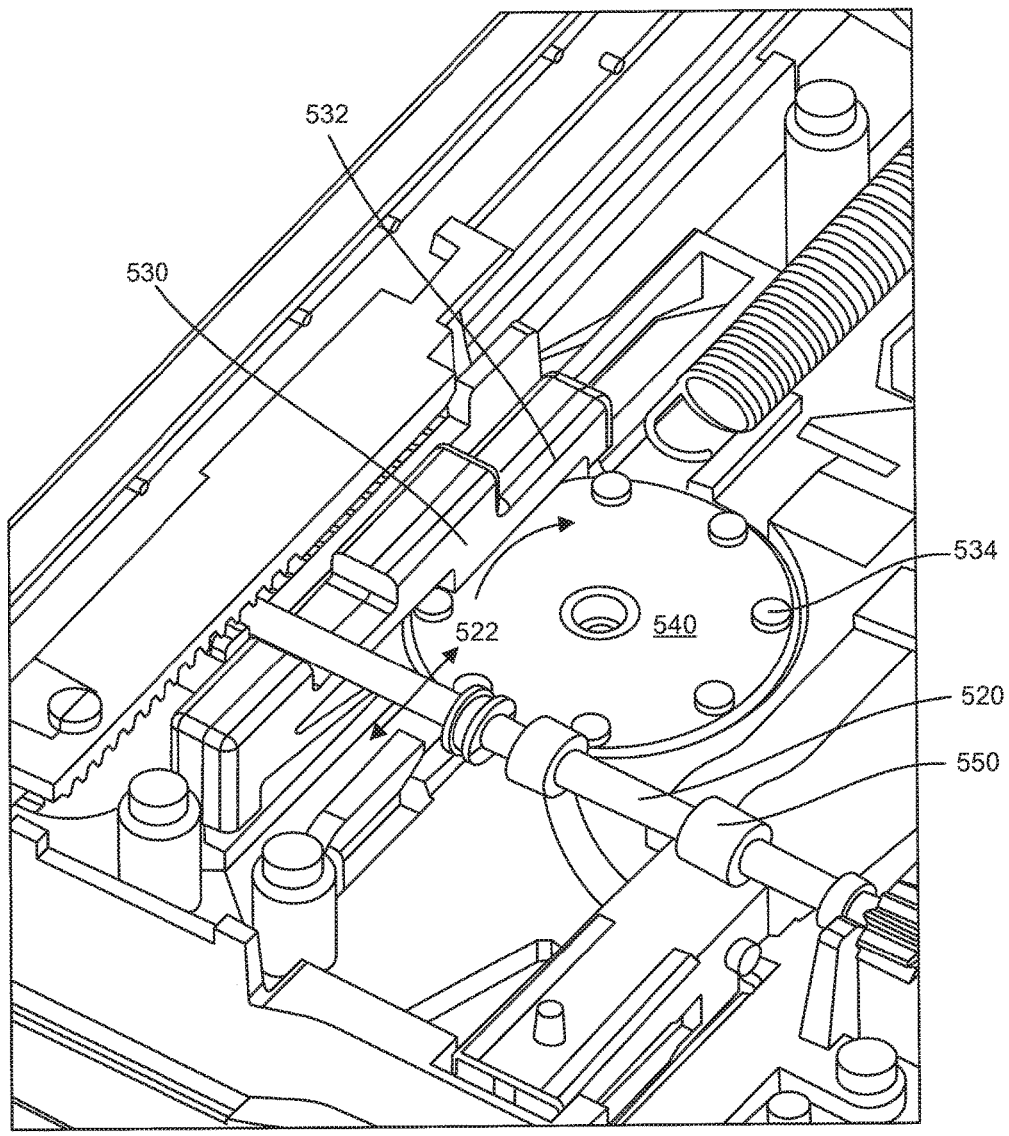
FIGS. 18 through 21 are cut-away views of various elements of a device according to the present invention.

Referring now to FIG. 18 shows how movement of the slider 510 moves rod 520 as indicate by arrows 522. For ease of illustration, certain portions of the device are removed to allow easier visualization of the moving parts. The motion of rod 522 causes a second slider 530 to move as indicated by arrow 532 and engage a stub 534 on the rotating wheel 540. This wheel 540 turns the gear the fits inside the opening 514, which rotates the cartridge. In the present embodiment, a roller 550 also travels on a cam surface 552.

Figure 19:
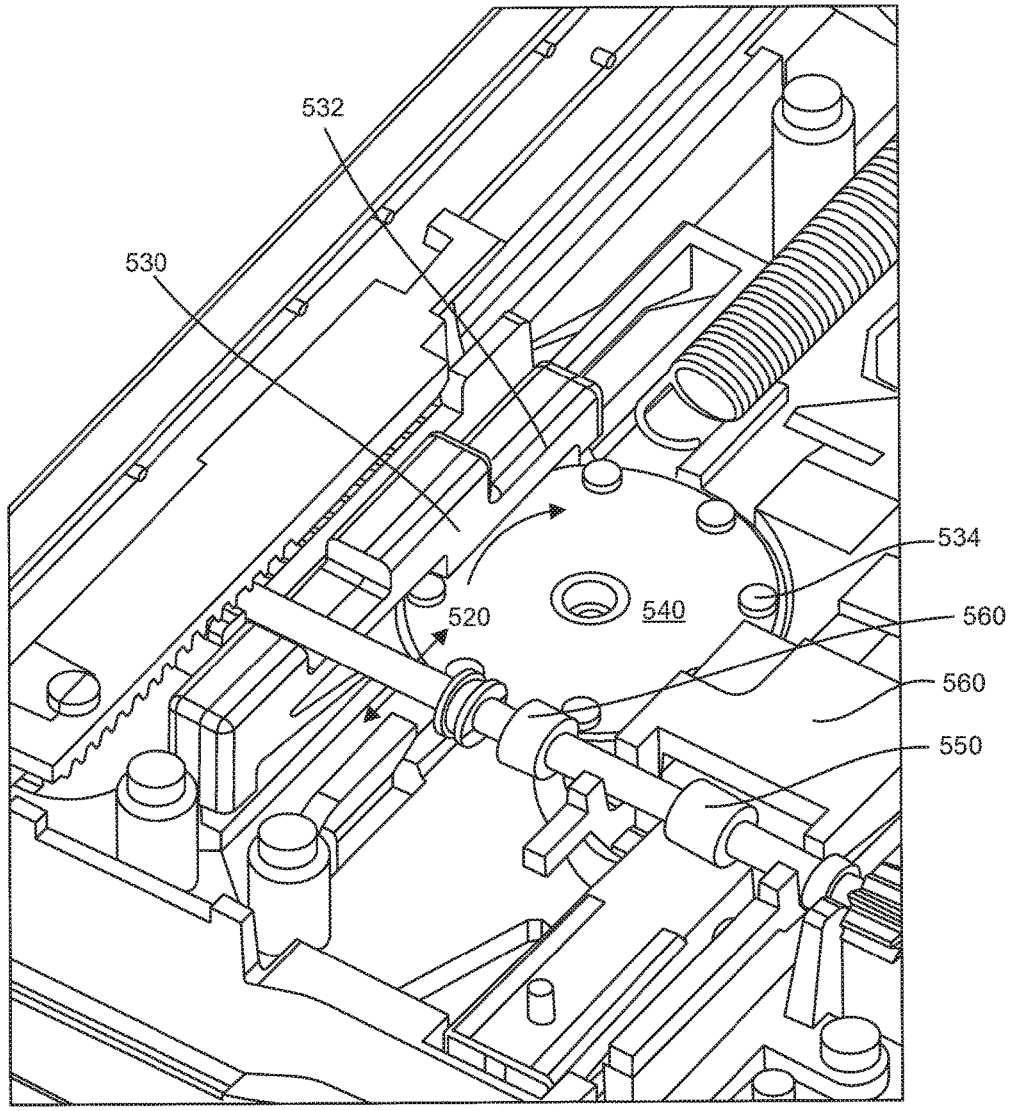
Figure 20:
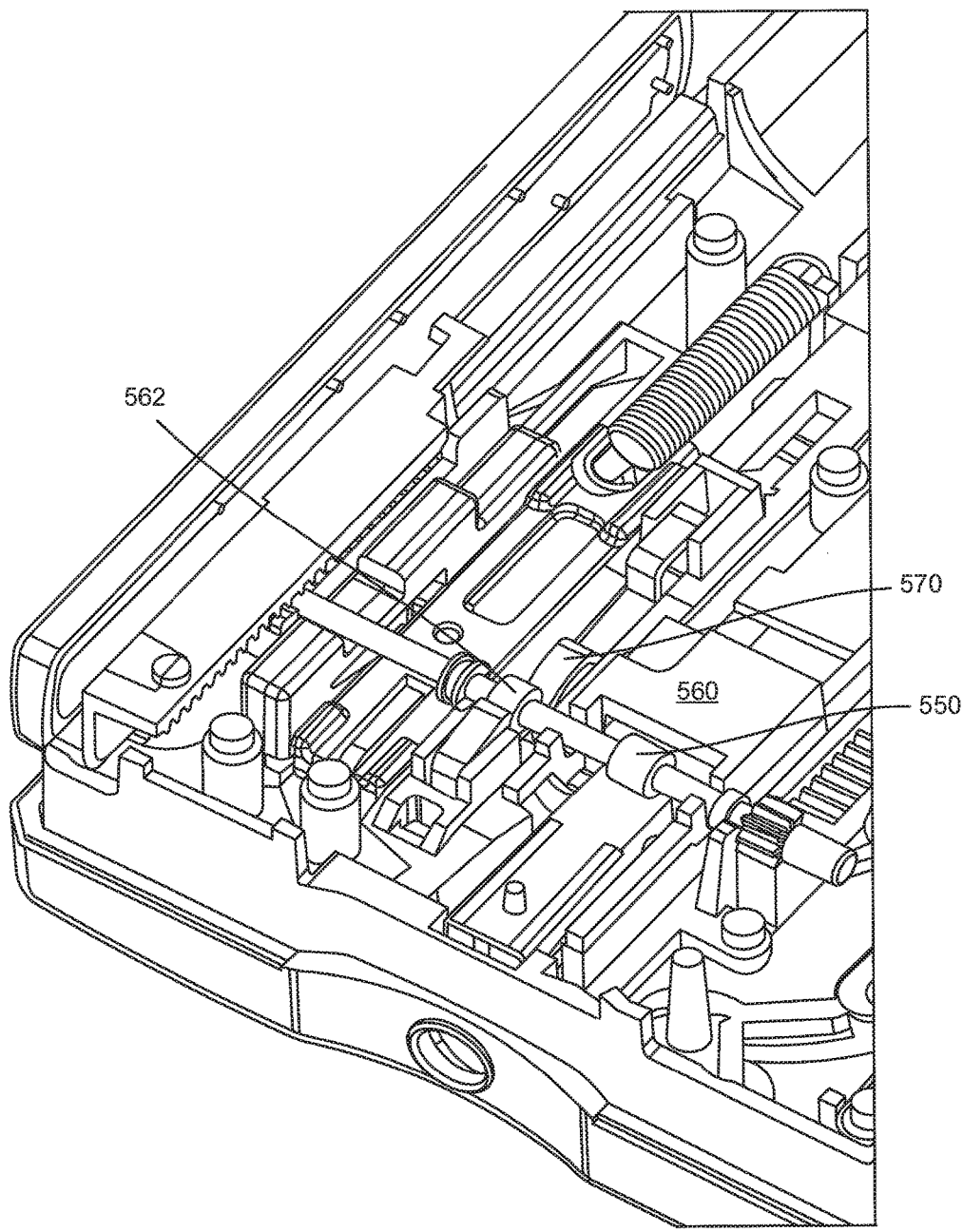

As seen in FIG. 19, the roller 550 also move a slider 560. The rod 520 also includes yet another roller 562. This roller as seen in FIG. 20, follows another cam surface 570. The cam surfaces 552 (FIG. 18) and 570 (FIG. 20) allow for raising and lowering of the punch, shield, gripper, drive assembly, etc. . . . to allow for the cartridge to rotate and a new penetrating member cavity to be opened and a member loaded for firing.

In some embodiments, the various steps that need to happen are similar to those described in commonly assigned copending U.S. patent application. Ser. No. 10/323,623 (38187-2607) filed Dec. 18, 2002.

Figure 21:
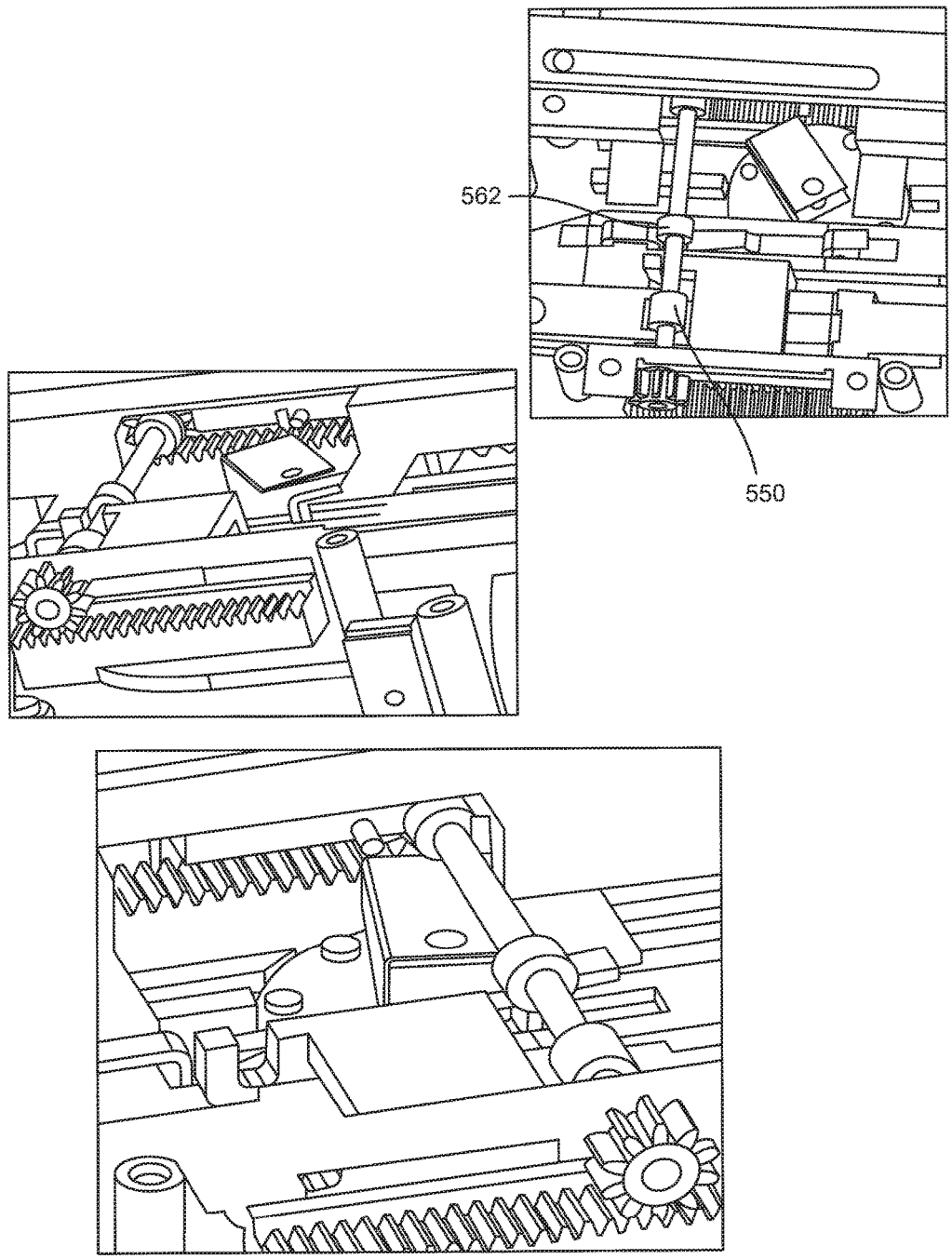

FIG. 21 shows still further embodiments of the present invention. It more clearly shows some of the elements such as roller 562. Embodiments using the linear motion of the slider 510 and linear motion of the rod 520 pushing linear sliders and pushing rollers to follow linear cam surfaces are very robust and will not easily fail. It should be understood that in some embodiments, a motor may be coupled to the slider to advance it instead of relying on user force.

Referring now to still further embodiments of the present invention:

1. C Shaped slug 3.6 mm—increase force outer diameter bigger, flux lines shorter saturates later so more force.

2. Ratchet finger: forces the punch cycle, removes peg pivot and spring mechanism for the one-way action before return cycle is initiated. For D layout flexible finger which is s shaped—the S shape give the spring like action without the need for and extra spring. 6 parts to 2. Delete a coil spring and pins to hold it. It is small but injection moldable, p-ins are molded in.

4. Hinge on the gripper track: Attach the solenoid to the gripper track so that the whole lot moves when the pull the gripper off the lancet. This is pivoted by bending so that the coil moves (and flag) but on the sensor just the flag in the slot.

5. Warping of disc: if the disc is over indexed (error) and rotational error in the gripper track then the shields will not be perfectly aligned. The main pockets are now tapered to take care of this. The walls are now parallel (they were tapered before). Tapering allows the shields to only to touch in the back corner. This is being tested this week and may reduce the forces to push in and pull out (the fact that it is tapered. If the disc isn't flat downswards, the gripper can move down to follow the tract of the resilient to cartridge. Statically determinant eg three legged stool on uneven floor. Takes into account poor manufacture in all parts including the gripper arm as well as the consumable. Consistent friction with any changes that might occur due to manufacturing. This is another advantage f the bearing system.

6. Collapsing cam mechanisms: ADA model—rolling beam slider needs mechanism so that it rolls back it punches but does not already punch the nxt cavity. Ts a ratchet ball point pen mechanism. Slot and wheel of ADA is too thick. New one has metal component which latches in place, pushing punch down, pushes component backwards, so that hump disappears. The is called the return plate. (sliding plate was Dons idea, they added metal)

7. Punch force detection is also in this model

8. Capcitative sensing: 2 embodiments, electrically connected to needle—since we have metal gripper and have an electrical circuit (they have model for needle sensing touching finger. Embodiment 2 pouching is now repeated deals with pouching only.

9. Leak testing: hermetic seal check on each pocket—desiccate, dye. Cavities fill with ink—end up with depression in the foil over the cavity—its this depression they have not observed in combination with the dye test. Foil thickness has not bee determined, 11 or 20 microns are the two candidates. 20 might be too high too punch, it's the same though, pin holes were less. If punch force stays low they will probably go for the twenty micron. Dyye incress can sense 10 um and cmbi test was less that 5 um.

10. Gripper stripper II chunk of plastic runs on track and pulls the gripper off the lancet. Does the same as the old cam but it is in two parts at it is a thinner embodiment.

11. Plastic punches—swallowtail punch shape. Front punch the cutting edge I creating a T shape. Back punch is hourglass shaped. Doing every other one and going around twice. Main punch is wider at front on the back because chambers are now tapered. The edges at the center are the cutting; gabled ends act as shearing guillotine. Saggy roof (swallowtail), minimized the peak force over all the displacement, saggy roof achieves this.

12. This is D layout, cartridge is Saturn 31 aka Rev 5 Disc 08000009-2. Design features added to solve jitter and friction. Jitter spec 50 microns, friction in the armature (moving assembly). Predictable repeatable is better tan none or high friction. Changed the bearing system (armature) slug has carbon rod and sits in tube. The end of the rd has a molding and the gripper. Lancet sits in cartridge and has two bearings, stroke is between the two bearings. The bearings are now V shaped light force makes lancet sits in v, when it hits skin it can ride up the sides of the v when the lancet hits the skin. It moves due to the 3 facet tip. This also allows a wide clearance. Before the result was jitter, the v groove defines the position and clearance in 98 microns. Free flight free flight is zero because it is getting pushed int the v. Can now move left, right or twist and follow the tip into the skin, The clearance at the rear and from are calculated to account for the orientation of the lancet into the skin it is free to move. The gripper is now mounted on a hinge and can rotate with the lancet. Plastic has elastic properties (delryn acetyl) is used for all springy parts in the model. The gripper head is what rotates, not the gripper, so molding is compliant to attach the gripper to the shaft. Slug is now diamond shaped. The damper sits on the rod and pushes down and applies the down wards pressure and damps out oscillation n the rod This takes some juice from the coil. 15 mN frictional force. Jitter plotted against friction force. Its below the 15 micron spec at 15 mN force at which contact point can be measured. Jitter under control by using friction A component sets the friction so that it is reproducible, so control system can compensate. There is some penalty in battery life—this has to be determined. This is the new Bearing system. Gripper then gets locked and then damper doesn't function while in the parked position. The gripper track—the shield are pushed out of the way. They fold the slits out of the way. Shield can maybe be used to keep the foil out of the way.

Figure 22:
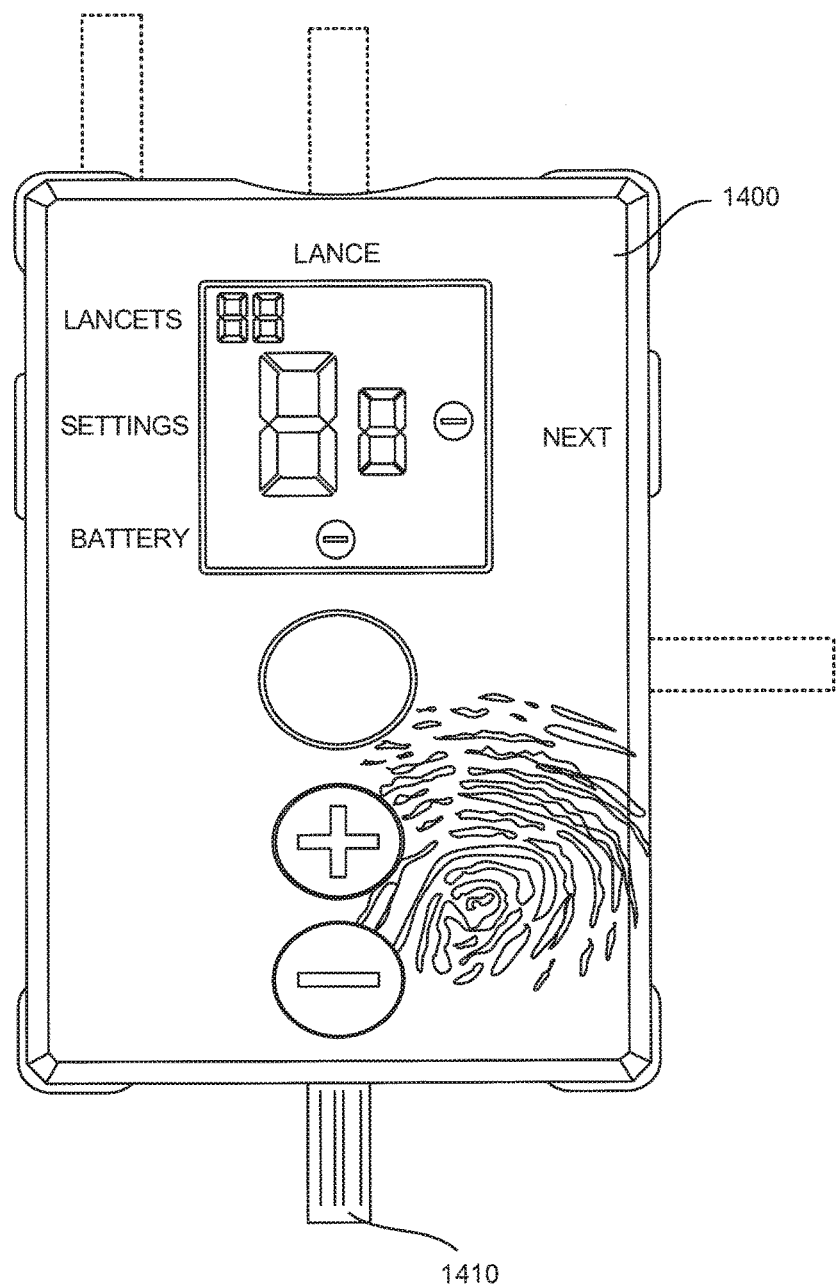
FIGS. 22-23 show embodiments of an analyte testing device for use with a test strip.

Referring now to FIG. 22, another embodiment of the present invention will now be described in greater detail. The device 1400 includes a cartridge similar to that of FIG. 6, except that it only has penetrating members, no analyte sensing. In this embodiment, the device 1400 include a glucose or other analyte meter. A test strip 1410 may be inserted into a slot on the device 1400 to allow for the body fluid on the test strip to be analyzed. As seen in FIG. 22, in different embodiments, the slot for the strip 1410 may be inserted in a variety of locations (as indicated in phantom). In some embodiments, the electronic lancing device 1400 may also dispense the test strips from a cartridge or cassette held within the housing of the device 1400.

The electronic lancing device may use a radial cartridge for housing the penetrating member or a bandolier type design as set forth in commonly assigned, copending U.S. patent application Ser. No. 10/127,395 (38187-2551) or PCT application No. PCT/US03/40095 (38187-2721).

Figure 23:
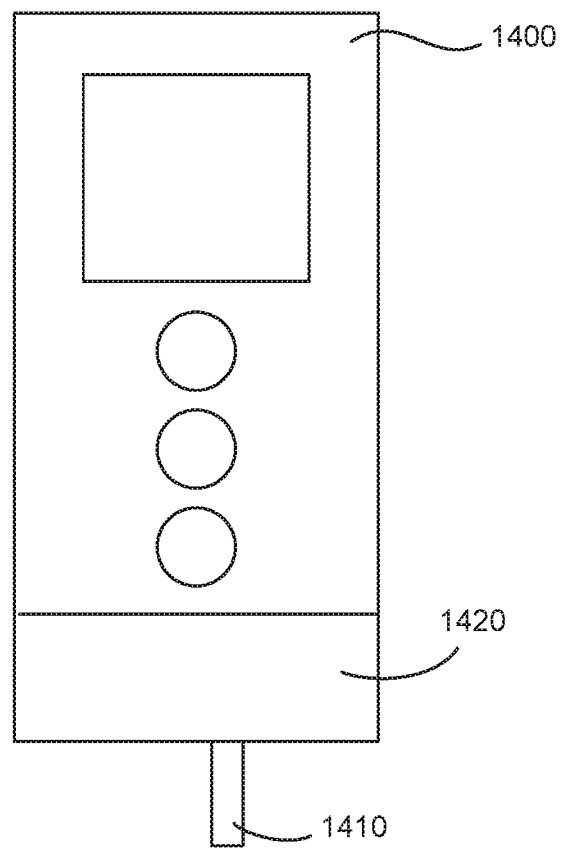

Referring now to FIG. 23, a still further embodiment is shown where an attachment 1420 may be added to an electronic lancing device. This attachment, in one embodiment, contains a plurality of test strips for dispensing. In another embodiment, it may provide the electronics used for functioning as glucose or other analyte meter.

Referring now to FIGS. 24 through 28, these embodiments of the present invention relate to Point of Care lancing, sampling, sensing, and disposable. The present invention provides a single device, suitable for use with multiple users in situations such as POC applications in adults or neonates. In one embodiment, the present invention address the issue by having a removable front end that both functions as a sample acquisition device and a sterility barrier between uses of a single device with multiple users in a professional care environment.

Figure 24:
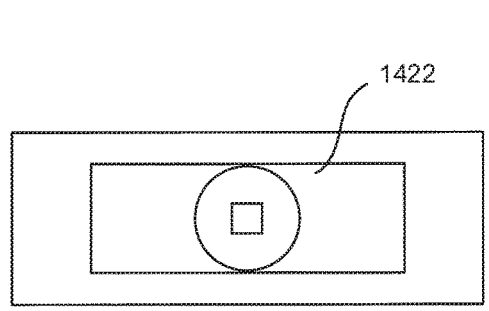
FIGS. 24-28 show various embodiments of a tissue interface.
Figure 25:
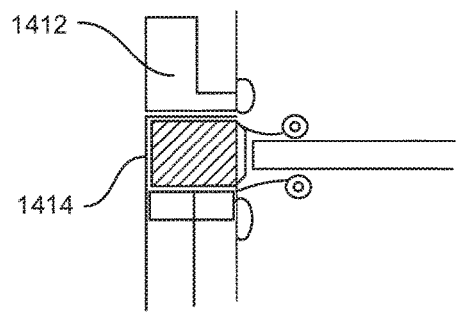

Referring now to FIGS. 24 and 25, sample capture from the surface of the finger may be carried out after the lancing step. A shield or guard may protect the front end from contamination and transfer of biohazard between successive patients. FIG. 24 shows that a portion 1422 may be hydrophobic. FIG. 25 shows that there may be hydrophobic plate 1412 and a hydrophilic mesh 1414.

Figure 26:
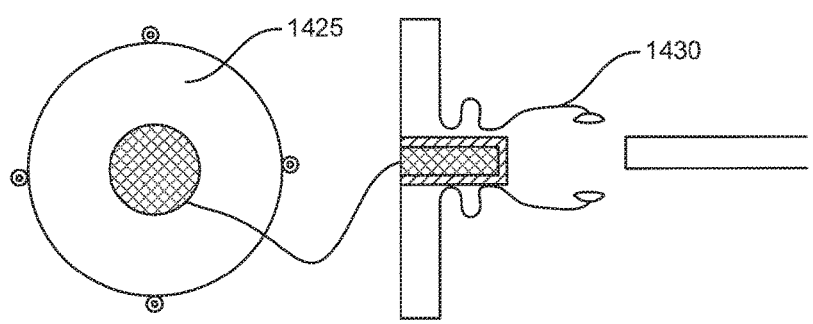
Figure 27:
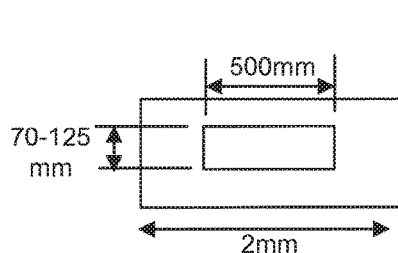
Figure 28:
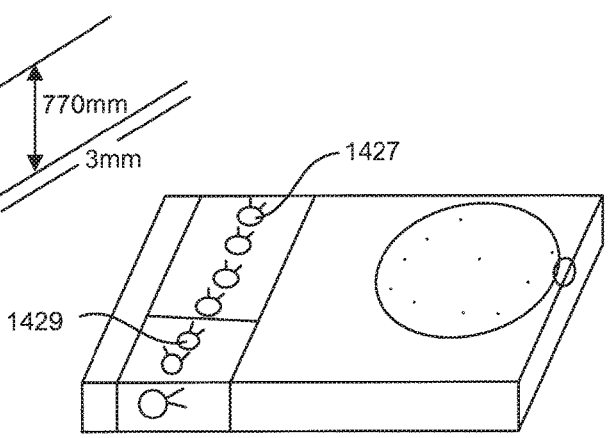

Referring now to FIG. 26, the present invention is a device 1425 that has a plastic molded part with "tentacles" 1430 designed to remove the foil covering of the analyte detecting member at the time the test is taking place. FIG. 27 shows some sizing of opening on the housing. The plug may snap into the aperture of the front end. It protects back plate and front end from blood. Clips also remove packaging. FIG. 28 shows a perspective view of a fluid sampling device having a plurality of front ends 1425 on the device that are ready for use. FIG. 28 shows that old or used front ends 1427 and new front ends 1429 may be placed on the housing. By way of example and not limitation, they may be mounted on band on a back portion of the housing.

Two embodiments of the sampling paradigm are possible.

(1) The lancing is carried out in a separate operation and the surface of the finger is touched to the wicking or sip-in treated front end of the disposable "limpet" 1425. Blood is guided into the analyte detecting member channel and the test is carried out. Post testing the "limpet" front end 1425 is removed and the disk indexed before inserting the next "limpet" for the next diagnostic test. The sample acquisition channel of the limpet can be configured with mesh to guide the sample to the analyte detecting member or hydrophillically treated to guide the blood to the analyte detecting member. Since POC tests require higher amounts of blood volume the dead space for the priming of the channel leading to the not considered limiting. Limpets can be stored on board in the instrument and dispensed as a cassette. They can also be disposed of in the same cassette as used and then the entire cassette thrown way at the end of 25 or 50 patients have been tested.

(2) Embodiment two would allow an fluid device combined with analyte detecting members on a disk. The punch mechanism of the lancing device can open the seal. The function of the limpet would them be to attach and for a sterility barrier on the front end, allow passage of the penetrating member through the center and perhaps contain surface treatment or mesh to guide the sample into the analyte detecting member chamber. The limpet can be configured to prevent contamination in a side-to-side aspect between analyte detecting members by forming a physical barrier between adjacent analyte detecting members. It can be configured to prevent splatter of blood on the back plane (inside of the front end) of the instrument. It may also function as a finger positioning device as it can be contoured and shaped without affecting the front face of the instrument.

Figure 29:
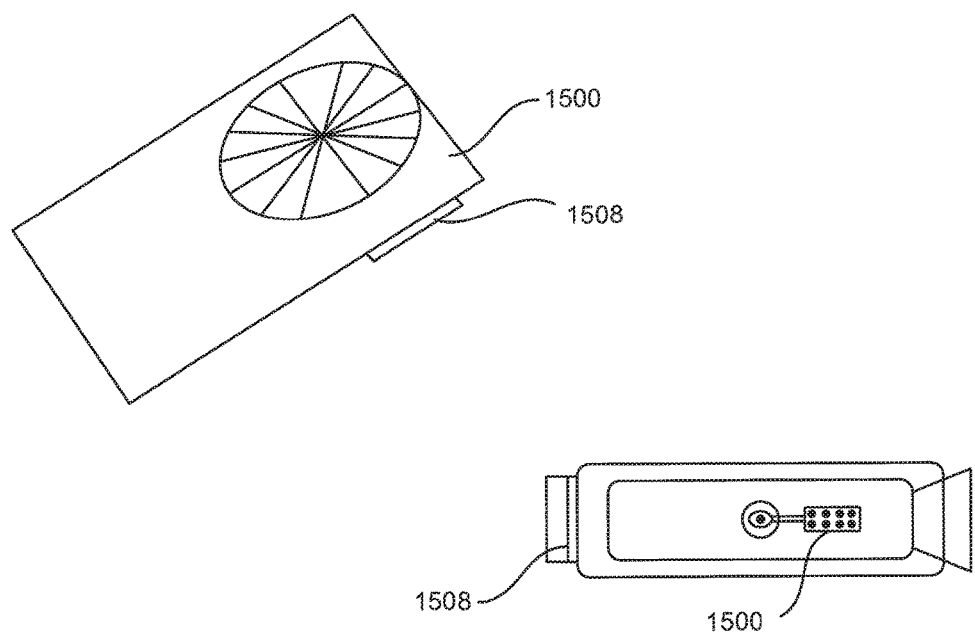
FIG. 29 shows one embodiment analyte testing strip dispenser.

Referring now to FIG. 29, these embodiments of the present invention relate to lancing, sampling, sensing, disposable, and manufacture. In one embodiment, It is an integrated sampling/glucose-sensing system. The present invention may integrate multiple lancings with multiple electrochemical glucose sensing events. It is solved here, in some embodiments, in a very simple way by integrating the functions without integrating the two different activities (lancing and sensing) in the same physical device.

Referring again to FIG. 29, one particular simple integration of the functions of blood sampling and glucose-sensing is shown. In this embodiment, a small package of disposable glucose sensing strips 1500 in a dispenser 1508 is physically adjoined to the lancing device. In order to perform a glucose analysis, a user tears off/peels off a strip from the dispenser, sticks it to the front end of the lancing device (using suitable registration features on both the strip and the front end), and then uses the device to lance and obtain blood. The strip 1500 has many of the blood collection features, notably a woven lollipop structure to guide blood over an electrochemical glucose analyte detecting member which is an integral part of the strip (the strip is very similar in function to any glucose test strip). The front end of the lancing device may have electrode contacts which can either actively or passively make contact with the electrochemical "signal out" pads of the strip. In a particular embodiment of this concept, a hinged door be deployed from the lancing device front end to aid in registering the glucose strip and to make contact with the "signal out" pads. Following use, the disposable glucose strip is removed from the front end of the device and disposed of in the normal way.

A somewhat similar, but more integrated, approach is discussed. Here the glucose-sensing strips are still kept physically separate from the multi-lancing elements, and are only functionally integrated, but in this embodiment, the glucose-sensing strips are integrated into their own multi-strip roll. Using this multi-strip roll (in a cartridge very similar to an old 110 film canister), the indexing of the penetrating member launcher can be used to move forward new, glucose strips. The glucose strips in their roll move across the front end of the fluid sampling device, and perform similarly to the strips in the concept above. The strips have registration features corresponding to registration features on the front end, and they have blood acquisition means, like a woven lollipop structure, to guide blood from the finger-lancing site to the electrochemical analyte detecting members. Contact to the "signal out" pads of the glucose test strips are accomplished by electrode contacts integral to the front end of the fluid sampling device. But in this case, there are no individual strips either to put on the front end of the fluid sampling, or to remove from the front end after use. The strips are deployed from a film canister-type cartridge, and are rolled back up into a similar canister feature on the other side of the fluid sampling after use. It is clear that a multi-strip canister of this sort could be functionally integrated with a multiple penetrating member system of various forms. A multiple-strip canister may be functionally integrated with multiple penetrating members in the form of a penetrating member magazine, or a radial penetrating member cartridge.

Figure 30:
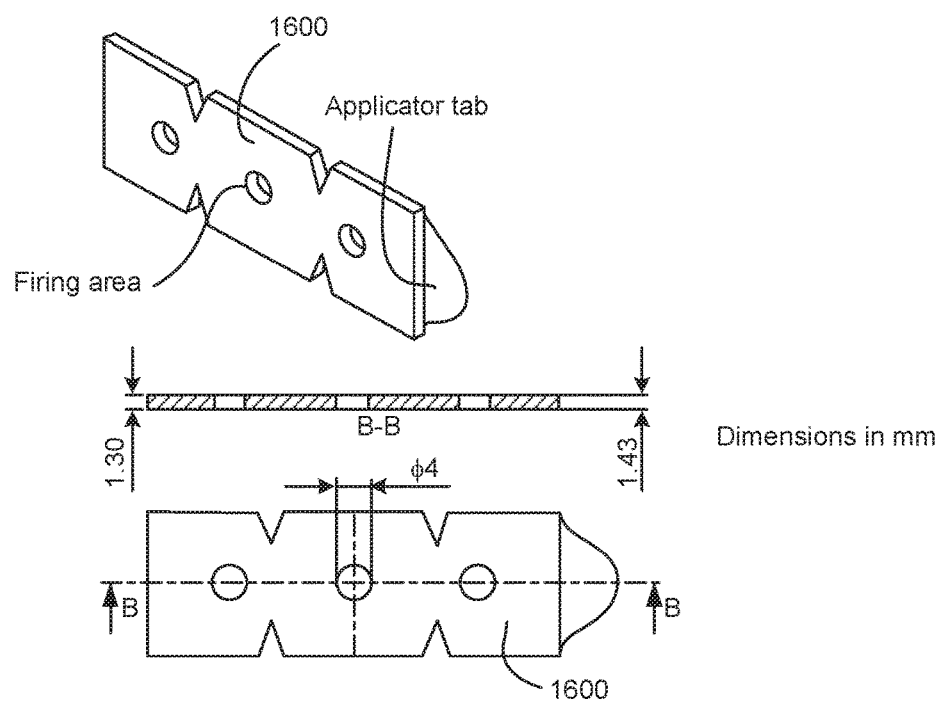
FIG. 30 through 35 shows various views of embodiments of a barrier according to the present invention.

Referring now to FIG. 30, still further embodiments of the present invention will be discussed. The technical field of these inventions relate to lancing, blood acquisition, contamination avoidance, sterile disposable materials. Most systems for gaining access to blood are single-use devices. Systems that are used to gain access to the blood of multiple people have the burden of showing that blood cannot be carried from one user to another. A means for avoiding that "blood carry-over" is the subject of this invention. That means is basically a specific material and design of tape that is used, and then discarded after use, between each patient.

Figure 31:
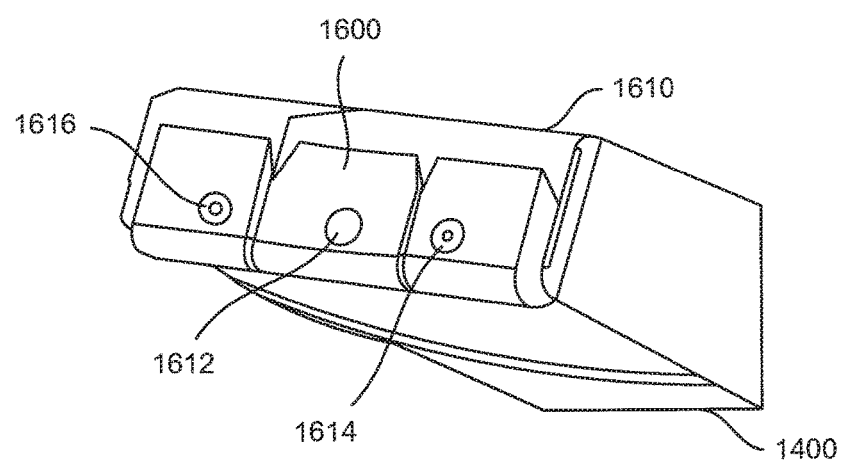

Referring now to FIG. 30, one embodiment of a sterile disposable adhesive blood barrier 1600 is to be placed between the device and the patient. The barrier 1600 may be applied to the exterior surface of the device before use with each patient and disposed of immediately after use. In the present embodiment, the adhesive blood barrier 1600 prevents contamination of any part of the device that may act as a pathway for transmission of pathogens between patients. Illustrations of the design are shown in FIG. 30 shows the barrier by itself. FIG. 31 shows the barrier 1600 attached to a fluid sampling device 1400. The barrier 1600 may have a bend relief 1610, foam offset 1612 and location features 1614 to help position the barrier properly. The port 1616 is where a penetrating member exits to piece tissue.

1.1. Description of Operation

As seen in FIG. 31, the user will apply the sterile adhesive blood barrier 1600 with foam pad to the front of the device and then place the patients' fingertip or other skin surface against the high-density foam offset pad in the firing area. The foam offset pad 1612 serves to maintain a small air gap between the patients' finger and the blood barrier film. The penetrating member then is fired through the sterile adhesive blood barrier 1600 and enters the patient before retracting back into the cartridge. Testing described below has shown that the small hole created by the penetrating member, in combination with the air gap created by the foam, is highly resistant to fluid flow. The blood barrier 1600 acts effectively in preventing transfer of blood to the device despite the presence of such a hole.

In one embodiment, the selected film for the barrier 1600 is manufactured by 3M Medical Tapes and Adhesives under the catalog name "3M™ Tan 5 mil Polyethylene Medical Tape 1523, 63# Liner".

The selected foam is sold by Scapa Medical UK under the catalog name "Medifix 4005/868 Single Coated Medical Pressure Sensitive Polyurethane Foam". The offset pad is made up to the required thickness as a multi-layer laminate.

Figure 32:
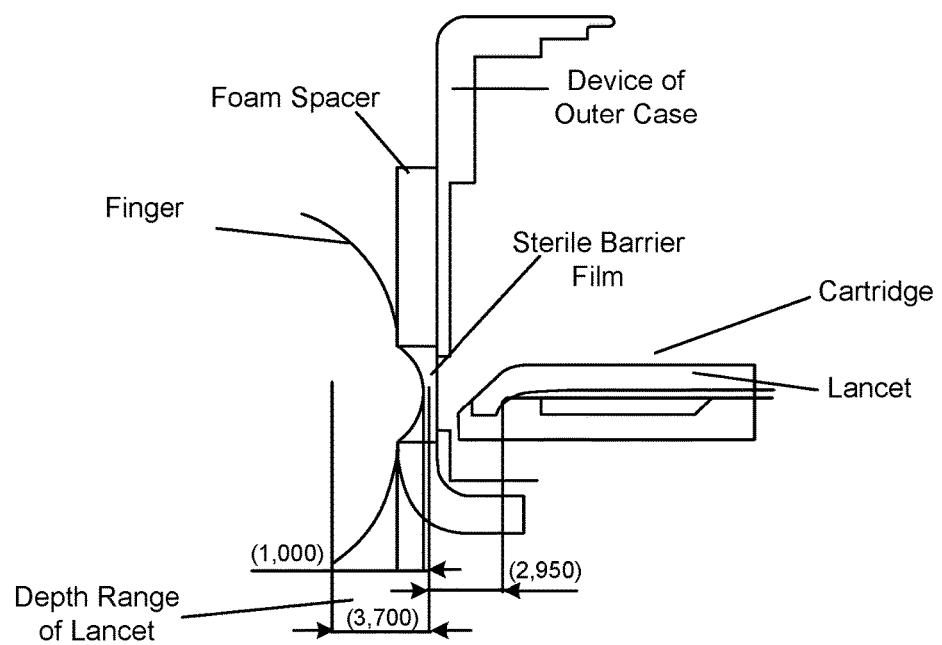

FIG. 32 is a cross-sectional diagram shows the relative dimensions of the proposed system prior to firing.

Figure 33:
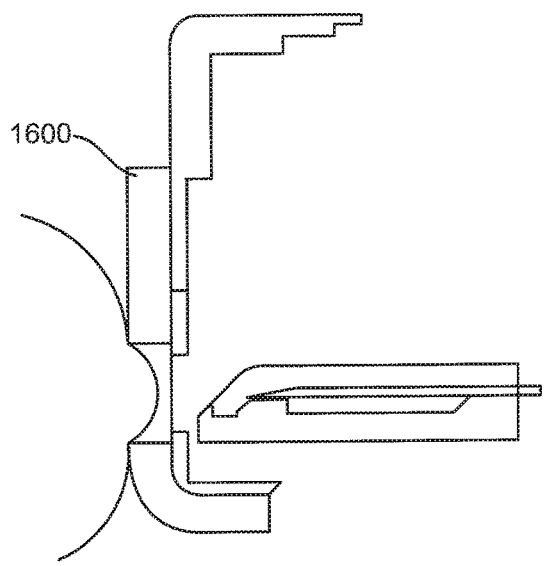
Figure 34:
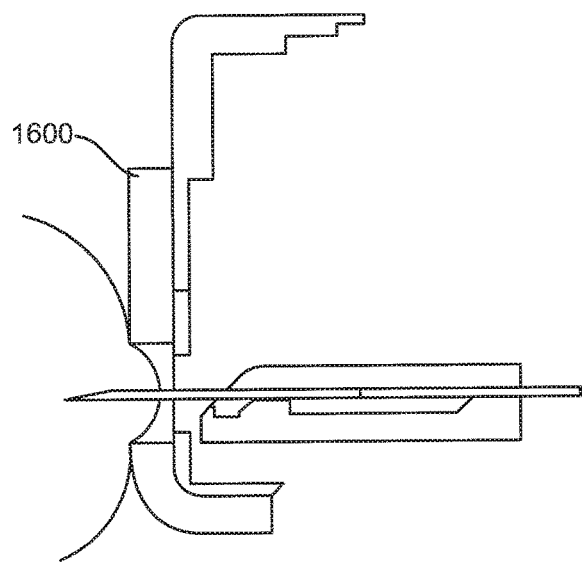
Figure 35:
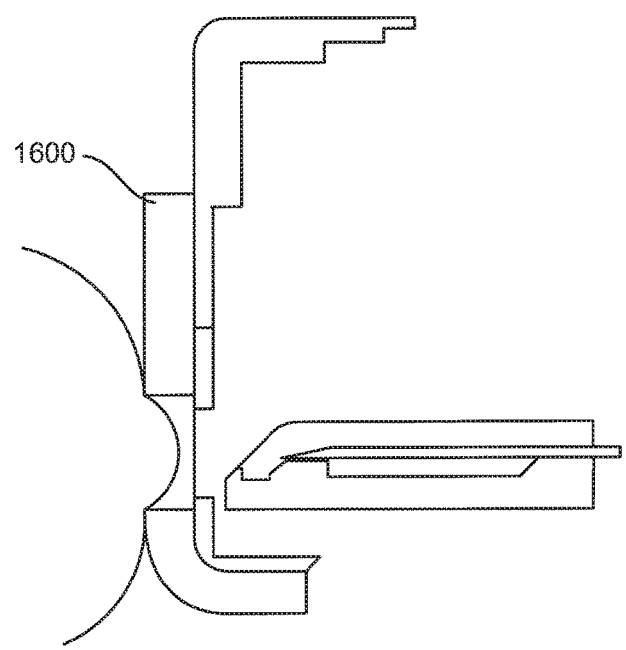

FIGS. 33, 34, and 35 are three diagrams that illustrate each phase of the lancing operation.

1.2. Prevention of Blood Transfer

First and foremost the film and foam prevent blood being left on the casework of the device by being a simple physical barrier. In one embodiment, the blood barrier 1600 will cover nearly the entire front of the device and also wrap underneath the device. User instructions require that the user clean any obvious blood contamination that is spread outside the area of the barrier with a suitable disinfectant method.

The chief risk is that the blood will be transmitted to the device via the hole created in the barrier film by the lancing operation. The success of the design relies on the elasticity of the selected film closing the hole, the surface tension and viscosity of the blood making passage through the small hole difficult, and the air gap providing for an alternative route in which the blood pressure can be released avoiding a pressure difference across the film.

Several experiments were completed to select a film and confirm that it satisfied the requirement of preventing contamination of the device.

1.2.1. Hydrostatic Pressure Test

Objective: To test whether a suitable film and air gap could withstand a blood pressure equal to that in the capillary blood vessels of the patient after being pierced by a penetrating member.

Method: A length of tubing filled with water was capped at one end by a piece of film intended to simulate skin. Offset from this "skin" was a sample of the film being tested. The height of the free surface of water was set to the maximum pressure likely to be transmitted to the film by the capillary bed, approximately 45 cmH20 (see below). A penetrating member was pushed through the test film and the "skin" and then slowly withdrawn whilst backlit and being filmed by a high speed macro video camera. This process was repeated for a variety of films of differing material and thickness.

Results: In the video footage it is obvious which combinations of air gap and film prevent fluid transmission. Results are presented in Table 1 and it is shown that the selected film will prevent fluid transmission for pressures of at least 45 cmH20 when offset from the skin by 0.6 mm.

| Test | Film | Description | Nature of film | Pressure (cmH20) | Air Gap (mm) | Penetration (Yes/No) |
|---|---|---|---|---|---|---|
| 1 | 6016/877 | 40 um PU | Hydrophilic | 9 | 0 | N |
| 2 | | | and elastic | 10 | 0 | N |
| 3 | | | | 12.5 | 0 | Y |
| 4 | | | | 16 | 0 | Y |
| 5 | Bioflex 140 | 25 um PU | Hydrophilic | 10 | 0 | N |
| 6 | | | and elastic | 10.5 | 0 | Y |
| 7 | RX941PLT | 40 um PET | Hydrophobic | 10 | 0.6 | N |
| 8 | | | and inelastic | 16 | 0.6 | Y |
| 9 | 1523 | 130 um PE | Hydrophobic | 20 | 0 | Y |

-continued

| Test | Film | Description | Nature of film | Pressure (cmH20) | Air Gap (mm) | Penetration (Yes/No) |
|---|---|---|---|---|---|---|
| 10 | | | and elastic | 25 | 0.6 | N |
| 11 | | | | 30 | 0.6 | N |
| 12 | | | | 32 | 0.6 | N |
| 13 | | | | 45 | 0.6 | N |
| 14 | | | | 45 | 0.6 | N |

The video footage shows the elastic closure of the hole as the penetrating member is retracted. This closure reduces the area of the hole to a fraction of the penetrating member diameter increasing the resistance to fluid flow tremendously.

The elastic closure also prevents the penetrating member carrying with it large drops of blood to the device side of the barrier which might otherwise be dislodged before the penetrating member is parked safely in the cartridge. As the penetrating member retracts, the film closes around it, wiping off any blood. Very small amounts of blood that may adhere to the surface of the penetrating member and be carried back to the device side of the barrier will be contained within the penetrating member cavity.

1.2.2. Theoretical calculation

Figure 36:
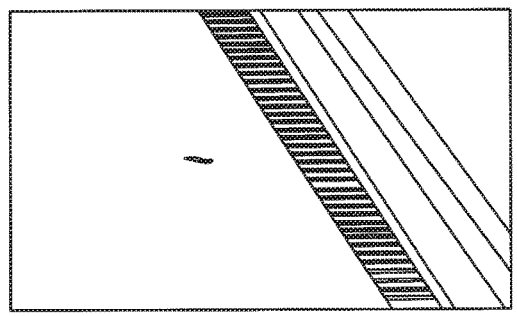
FIGS. 36 through 40 show various close-up views of areas of the barrier.

Theory governing fluid passage through a small hole states that the required driving pressure for liquid to move through a small hole is given by:

$$P = \frac{4a}{d} \quad \text{Equation 1}$$

where: P is the driving pressure in Pa
a is the surface tension of the fluid in N/m
and d is the diameter of the hole in meters The surface tension of blood has been shown to be in the region of $56 \times 10^{-3}$ N/m. The crescent shaped hole left by the penetrating member after elastic closure is approximately $6 \times 10^{-9}$ m$^2$ in area (see "FIG. 36. Puncture hole with 0.317 mm diameter penetrating member for scale"), which is equivalent to hole with a diameter of $4.4 \times 10$-5 m. Equation 1 therefore gives a required driving pressure of 5.10 kPa. Adhesion of the blood to the sharp corners of the hole is likely to make the actual required driving pressure significantly higher than this The blood pressure in the capillary bed drops from a maximum of 30-35 mmHg at the arterial end to 12-15 mmHg at the venous end. A pressure of 30-35 mmHg equates to approximately 4.65 kPa or 45 cm H$_2$0. The actual pressure witnessed by the barrier and hole is likely to be significantly lower than this due to the presence of the air gap and the resistance to flow through the outer epidermis.

Theory therefore predicts that because the actual driving pressure is less than that required, fluid flow will not occur.

1.2.3. In Vivo Test

Objective: To confirm the laboratory experimentation the film selection by in vivo testing using a prototype device and live patient.

Method: The barrier film and foam offset pad were applied to the prototype device. The device was then placed against the finger of the patient and fired. The barrier was inspected on the Mitutoyo after the lancing operation at 96× magnification.

Result: The barrier film showed no transmission of blood. During this testing it was also shown that the blood is not smeared on the blood barrier and that a sufficient sample of blood is left on the patient skin for analytical testing.

Figure 37:
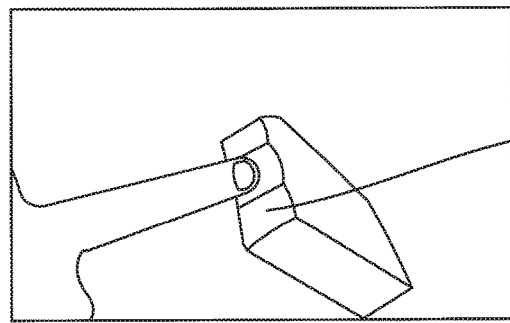
Figure 38:
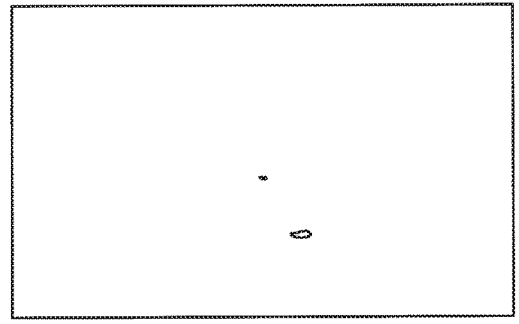
Figure 39:
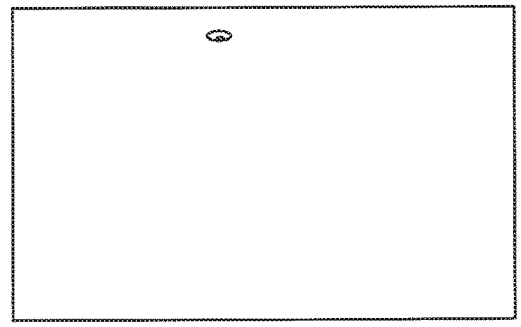
Figure 40:
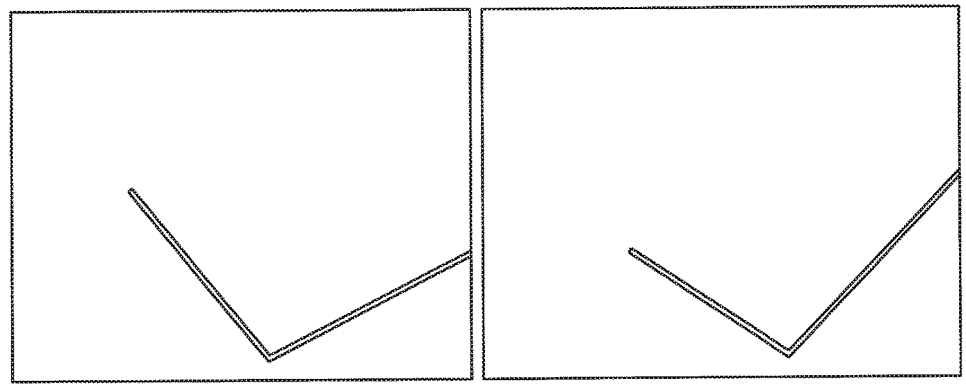

FIG. 37 shows a fluid sampling device with finger; FIG. 38 shows a blood drop on patient side of film (16×); FIG. 39 shows device side of film after firing into finger (96×).

The laboratory tests and theoretical equations support the hypothesis that the design is effective in preventing contamination of the device by blood.

1.3. Foreign Body Implantation

It is desirable that the penetrating member does not carry material from the adhesive blood barrier with it and implant it into the patient. The film is an elastic and ductile material being punctured by a sharpened point and it is therefore highly unlikely that pieces will be separated off and carried with the lubricated penetrating member tip. The following inspections were carried out to confirm this.

Method: A digital photograph of the penetrating member was taken immediately after firing through the adhesive film. This inspection was made along the length of 10 penetrating members after firing through the adhesive film.

The film was inspected after firing through it.

A high frame-rate (2000 frames/second) digital video was taken of the lancing operation from the patient side.

Results: No plastic material or adhesive was seen stuck to the penetrating member.

Inspection of the film using the Mitutoyo after piercing did not suggest that material had been removed (see "FIG. 25. Barrier film after puncture (96× magnification)").

No material removal was seen in the video footage.

Conclusion: Inspection of the penetrating member, the film and the process suggest that material is not removed during the firing process.

1.4. Sterility of the Blood Barrier

In one embodiment, the adhesive blood barrier 1600 will be prepared and packaged in a cleanroom environment and then gamma sterilized. Their respective manufacturers have declared the selected film and foam suitable for gamma sterilization. All manufacturing will be completed by an EN 13485 certified manufacturer and in accordance with that standard.

The barrier film will be presented to the user on a sterilized impermeable carrier and covered by another impermeable protective. The blood barrier film is then only exposed to possible contaminants once it is removed from its packaging in preparation for use. Applicator tabs and location details will be help to reduce handling of the lancing area as much as possible.

1.5. Cross Contamination Between Penetrating Members

Figure 42:
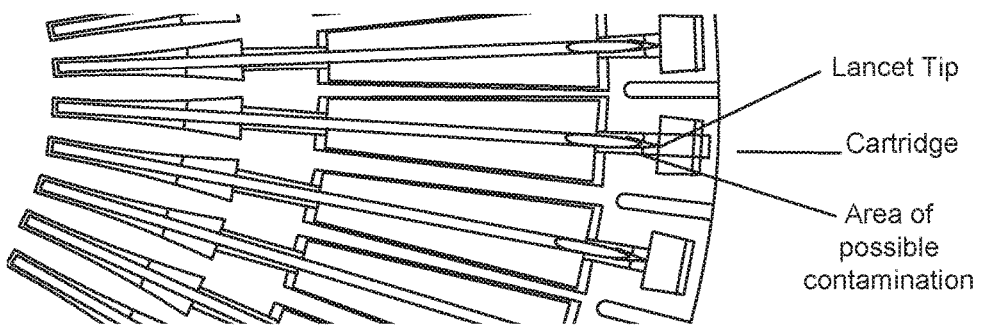
FIG. 42 shows a view of one portion of a cartridge for use with the present invention.

In the current solution very small amounts of blood may adhere to the penetrating member and travel back into the cartridge. Each penetrating member is contained within its own cavity that is separated from adjacent cavities and the mechanism. This separation is sufficient in size and geometry to prevent pathogens spreading. The adjacent unused sterile penetrating member is hermetically sealed up until the time of firing. FIG. 42 Plan view of part of the penetrating member cartridge (protective foil not shown)" below show the layout of the cartridge in which the penetrating members are contained. From these drawings it can be seen that the distance between penetrating members is large enough to prevent pathogens traveling between penetrating members even were they not sealed.

1.6. Penetrating Member Damage

Operation of the device may be impeded and pain levels increased if the penetrating member were to be damaged by the film before it entered the patient skin. To check damage did not occur 5 penetrating members were inspected before and after a lancing operation using the device prototype. The penetrating members showed no visible damage to the sharpened tip during the firing process.

1.7. Application of Barrier

Incorrect application might place the high-density foam offset pad in the trajectory of the penetrating member or reduce the effectiveness of the foam in creating the air gap described above. To prevent such misapplication features are provided on the outer case of the fluid sampling Pro to match the geometry of the barrier film. These features make misapplication obvious and reinforce the user instructions. The features are shown in 2. Appendix I: Instructions for Application of Barrier Referring to the information below, one embodiment of the instructions for users of the fluid sampling Pro Penetrating member Launcher Sterile Blood Barrier will be shown.

This device is for use by healthcare professionals only. It is recommended that the operator wear sterile gloves when using the device.

1. Prepare the skin of the patient in the area to be lanced with a sterile wipe.

2. Remove the protective covering from the packaging exposing a single item of sterile barrier film by pulling on the tab provided. Remove the sterile barrier film from the carrier by pulling on the applicator tab provided. (See illustrations below)

3. Apply the adhesive side to the front area of the device ensuring that both the outer circular holes in the barrier film fit around the matching circular bosses on the front of the device.

4. Press the sterile barrier film to the front and underside of the case taking care not to touch the firing area of the barrier film.

5. Prepare a penetrating member by operating the slider on the side of the device and depressing the fire button once. (See Lancing Device User Instructions)

6. Press the center circular cutout in the foam front of the barrier film against the patients skin in the area to be lanced.

7. Lance the patient by depressing the fire button a second time.

8. Remove the device from the patients skin and take the blood sample from their skin.

9. Carefully remove the barrier film from the front of the device using the tab provided and dispose of it properly.

10. Check that outer case of device has not been contaminated by blood and if necessary clean it with disinfectant.

Figure 41:
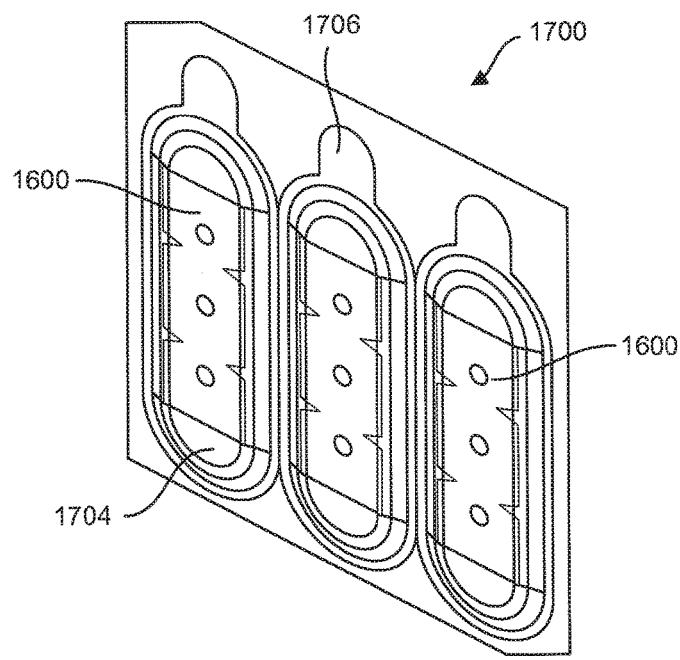
FIG. 41 shows one embodiment of packaging for use with a barrier according to the present invention.

FIG. 41 shows one embodiment of packaging for holding sterile barriers 1600. The packaging 1700 may include a sterile carrier 1702 and a protective cover 1704. Tabs 1706 may be used to facilitate pealing of the protective covers 1704.

FIG. 42 shows the possible areas of contamination and the barrier 1600 is designed to minimize the flow of blood to these areas or to prevent users from coming in to contact with any blood on these areas.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the shield or other punch may be adapted for use with other cartridges disclosed herein or in related applications. With any of the above embodiments, a motor may be directly coupled to rotate the cartridge.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. U.S. Provisional Application No. 60/577,412 and U.S. Provisional Application No. 60/577,376 are fully incorporated herein by reference for all purposes.

Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A fluid sampling device comprising:
a housing;
a cartridge positioned in the housing
a plurality of body fluid sensing strips integrated into a multi-strip roll;
at least one penetrating member positioned in the cartridge;
a gripper engaged to a penetrating member;
a drive assembly coupled to the cartridge;
a member for moving the cartridge to bring an unused penetrating member into position for launch, the member clearing the gripper and drive assembly to lift the gripper and drive assembly clear so that the cartridge can rotate; and
a sterile blood barrier with an offset pad to maintain an air gap between a patients' finger and the sterile blood barrier, wherein the offset pad is a multi-layer laminate, the sterile blood barrier including a bend relief and one or more location features to position the sterile blood barrier.

2. The device of claim 1 wherein a cam surface is aligned parallel to a slider.

3. The device of claim 1 wherein a linear motion of a cam rotates the cartridge and moves a plunger to break the sterility barrier on the cartridge.

4. The device of claim 1 wherein a cam surface comprises a linear strip of maternal with at least two raised portions and two depressed portions.

5. A fluid sampling device comprising;
a housing;
a cartridge defining a plurality of cavities, said cartridge sized to fit within said housing; a plurality of body fluid sensing strips integrated into a multi-strip roll;
a plurality of penetrating members at least partially contained in said cavities of the cartridge wherein each of a penetrating member is slidably movable, to extend outward from said cartridge to penetrate tissue; said cavities each having a lateral opening providing access to an elongate portion of the penetrating member;
a gripper configured to be engaged with each of a penetrating member;
a drive assembly coupled to the cartridge;
a sterile blood barrier with an offset pad to maintain an air gap between a patients' finger and the sterile blood barrier, wherein the offset pad is a multi-layer laminate, the sterile blood barrier including a bend relief and one or more location features to position the sterile blood barrier; and
a member for moving the cartridge to bring an unused penetrating member into position for launch, the member clearing the gripper and drive assembly to lift the gripper and drive assembly clear so that the cartridge can rotate.

6. A device comprising:
a housing;
a penetrating member driver;
a cartridge containing a plurality of penetrating members;
a plurality of body fluid sensing strips integrated into a multi-strip roll;
a display on said cartridge;
a linear slider on the housing, said slider coupled to a rod;
said rod moving with said slider, said rod having at least one roller using a linear motion of the slider to rotate the cartridge, punch open a new cavity and load an unused penetrating member;
a gripper configured to be engaged with each of a penetrating member;
a driver coupled to the cartridge;
a member for moving the cartridge to bring an unused penetrating member into position for launch, the member clearing the gripper and drive assembly to lift the gripper and drive assembly clear so that the cartridge can rotate;
a sterile blood barrier with an offset pad to maintain an air gap between a patients' finger and the sterile blood barrier wherein the offset pad is a multi-layer laminate the sterile blood barrier including a bend relief and one or more location features to position the sterile blood barrier.

7. A device comprising:
a cartridge having a plurality of cavities;
a plurality of body fluid sensing strips integrated into a multi-strip roll;
a plurality of penetrating members at least partially contained in said cavities of the single cartridge wherein the penetrating members are slidably movable to extend outward from lateral openings on said cartridge to penetrate tissue;
a sterile blood barrier with an offset pad to maintain an air gap between a patients' finger and the sterile blood barrier wherein the offset pad is a multi-layer laminate, the sterile blood barrier including a bend relief and one or more location features to position the sterile blood barrier;
a gripper configured to be engaged with each of a penetrating member;
a drive assembly coupled to the gripper; and
a member for moving the cartridge to bring an unused penetrating member into position for launch, the member clearing the gripper and drive assembly to lift the gripper and drive assembly clear so that the cartridge can rotate.

8. A method for obtaining a fluid sample comprising:
removing a protective covering from a packaging exposing a single item of sterile blood barrier;
positioning cartridge that contains a plurality of penetrating members in a position to launch a penetrating member;
using a plurality of body fluid sensing strips in the form of an integrated multi-strip roll;
engaging each of a penetrating member with a gripper;
engaging the cartridge with a drive assembly; and
moving the cartridge to bring an unused penetrating member into position for launch, the member clearing the gripper and drive assembly to lift the gripper and drive assembly clear so that the cartridge can rotate;
providing a sterile blood barrier with an offset pad to maintain an air gap between a patients' finger and the sterile blood barrier, wherein the offset pad is a multi-layer laminate, the sterile blood barrier including a bend relief and one or more location features to position the sterile blood barrier; and
lancing the patient.

9. The method of claim 8, wherein the sterile blood barrier is replaced for each of a new patient.

10. The method of claim 9, wherein the sterile blood barrier is placed between the device and the patient.

11. The method of claim 9, wherein the sterile blood barrier is used to prevent contamination of any part of the device that can be a pathway for transmission of pathogens between patients.

12. The method of claim 8, further comprising: a plurality of analyte sensing members, each of an analyte sensing member associated with a penetrating member.

13. A method of indexing comprising:
providing a fluid sampling device that includes a housing, a plurality of penetrating members positioned in a cartridge that is positioned in the housings and a plurality of analyte sensing members;
providing a plurality of body fluid sensing strips integrated into a multi-strip roll;
using a gripper to engage with each of a plurality of penetrating members;
engaging the cartridge with a drive assembly;
providing a sterile blood barrier with an offset pad to maintain an air gap between a patients' finger and the sterile blood barrier, wherein the offset pad is a multi-layer laminate, the sterile blood barrier including a bend relief and one or more location features to position the sterile blood barrier; and
using a member for moving the cartridge to bring an unused penetrating member into position for launch, the member clearing the gripper and drive assembly to lift the gripper and drive assembly clear so that the cartridge can rotate.

14. The method of claim 13, wherein a new disposable blood barrier is used when a fluid sample is obtained for a different patient to prevent contamination from one patient to another patient.

15. A fluid sampling device comprising:
a housing;
a cartridge positioned in the housing;
a plurality of body fluid sensing strips integrated into a multi-strip roll;
at least one a penetrating member positioned in the cartridge;
a gripper engaged to a penetrating member;
a drive assembly coupled to the gripper;

a sterile blood barrier with an offset pad to maintain an air gap between a patients' finger and the sterile blood barrier, wherein the offset pad is a multi-layer laminate, the sterile blood barrier including a bend relief and one or more location features to position the sterile blood barrier; and a member for moving the cartridge to bring an unused penetrating member into position for launch, the member clearing the gripper and drive assembly to lift the gripper and drive assembly clear so that the cartridge can rotate.

16. A fluid sampling device comprising:

a housing;

a cartridge defining a plurality of cavities, said cartridge sized to fit within said housing;

a plurality of body fluid sensing strips integrated into a multi-strip roll;

a plurality of penetrating members at least partially contained in said cavities of the cartridge wherein each of a penetrating member is slidably movable to extend outward from said cartridge to penetrate tissue, said cavities each having a lateral opening providing access to an elongate portion of the penetrating member;

a gripper configured to be engaged with each of a penetrating member;

a drive assembly coupled to the cartridge;

a sterile blood barrier with an offset pad to maintain an air gap between a patients' finger and the sterile blood barrier, wherein the offset pad is a multi-layer laminate, the sterile blood barrier including a bend relief and one or more location features to position the sterile blood barrier; and a member for moving the cartridge to bring an unused penetrating member into position for launch, the member clearing the gripper and drive assembly to lift the gripper and drive assembly clear so that the cartridge can rotate.

17. A device comprising:

a cartridge having a plurality of cavities;

a plurality of body fluid sensing strips integrated into a multi-strip roll;

a plurality of penetrating members at least partially contained in said cavities of the single cartridge wherein each of the plurality of penetrating members is slidably movable to extend outward from lateral openings on said cartridge to penetrate tissue, each of a lateral opening associated with a penetrating member;

a sterile blood barrier with an offset pad to maintain an air gap between a patients' finger and the sterile blood barrier, wherein the offset pad is a multi-layer laminate, the sterile blood barrier including a bend relief and one or more location features to position the sterile blood barrier;

a gripper configured to be engaged with each of a penetrating member;

a drive assembly coupled to the cartridge; and a member for moving the cartridge to bring an unused penetrating member into position for launch, the member clearing the gripper and drive assembly to lift the gripper and drive assembly clear so that the cartridge can rotate.

* * * * *